United States Patent
Wilde et al.

(10) Patent No.: US 7,902,241 B2
(45) Date of Patent: Mar. 8, 2011

(54) UREIDO SUBSTITUTED BENZOIC ACID COMPOUNDS AND THEIR USE FOR NONSENSE SUPPRESSION AND THE TREATMENT OF DISEASE

(75) Inventors: Richard G. Wilde, Somerville, NJ (US); James J. Takasugi, Lawrenceville, NJ (US); Seongwoo Hwang, Edison, NJ (US); Ellen M. Welch, Califon, NJ (US); Guangming Chen, Bridgewater, NJ (US)

(73) Assignee: PTC Therapeutics, Inc., South Plainfiled, NJ (US)

( * ) Notice: Subject to any disclaimer, the term of this patent is extended or adjusted under 35 U.S.C. 154(b) by 155 days.

(21) Appl. No.: 12/140,641

(22) Filed: Jun. 17, 2008

(65) Prior Publication Data

US 2008/0275233 A1    Nov. 6, 2008

Related U.S. Application Data

(62) Division of application No. 11/048,656, filed on Jan. 21, 2005, now Pat. No. 7,405,233.

(60) Provisional application No. 60/398,333, filed on Jul. 24, 2002.

(51) Int. Cl.
*A61K 31/425* (2006.01)
*C07D 233/00* (2006.01)

(52) U.S. Cl. .................................... 514/386; 548/322.5

(58) Field of Classification Search ............... 548/322.5; 514/386
See application file for complete search history.

(56) References Cited

U.S. PATENT DOCUMENTS

| | | | |
|---|---|---|---|
| 2,680,730 A | 6/1954 | Elmore | |
| 3,799,969 A | 3/1974 | Hoppe | |
| 3,946,033 A | 3/1976 | Iwata et al. | |
| 4,174,398 A | 11/1979 | Regel et al. | |
| 4,402,731 A | 9/1983 | Aya et al. | |
| 6,037,345 A | 3/2000 | Pamukcu et al. | |
| 6,838,476 B1 | 1/2005 | Almansa et al. | |

FOREIGN PATENT DOCUMENTS

| | | |
|---|---|---|
| EP | 1205478 | 5/2002 |
| JP | 04-987668 A | 8/1974 |
| JP | 50-077369 | 6/1975 |
| WO | WO 00/26203 | 5/2000 |
| WO | WO 01/12188 | 2/2001 |
| WO | WO 02/070494 | 9/2002 |
| WO | WO 02/081453 | 10/2002 |

OTHER PUBLICATIONS

Hara et al., 1975, CAS: 83:164831.*
Iwata and Hara, 1978, "Novel Synthesis of Hydantoin Derivatives," *J. of Het. Chem.* 15:1231-1234.
Ouof et al., 1972, A Contribution to the Study of Chemistry of Substituted Urea and Thiourea Derivatives,: *Egypt. J. Pharm. Sci.* 13(2):215-223 (including CAPLUS Abstract STN Database accession No. 1974:552150).
Abstract: Database Beilstein, Beilstein Institute for Organic Chemistry, Frankfurt, Main, DE, Database Accession No. BRN 850669, 847575 (XP 002261772) (1988).
Abstract: Database Beilstein, Beilstein Institute for Organic Chemistry, Frankfurt-Main, DE, Database Accession No. BRN 8288364, 8288635, 8288314 (XP 002261773) (2000).
Abstract: Database Beilstein, Beilstein Institute for Organic Chemistry, Frankfurt-Main, DE; Database Accession No. BRN 3385323 (XP 002261774) (1990).
Abstract: Database Beilstein, Beilstein Institute for Organic Chemistry, Frankfurt-Main, DE; Database Accession No. BRN 2142974, 2153838, 214575 (XP 002261775) (1989).
Barton-Davis et al., "Aminoglycoside antibiotics restore dystrophin function to skeletal muscles of *mdx* mice", *J. Clin. Invest.* 104:375-381 (1999).
Baures, PW, et al., "Synthesis and Evaluation of Inhibitors of Transthyretin Amyloid Formation Based on the Non-Steroidal Anti-Inflammatory Drug, Flufenamic Acid", *Bioorganic and Medical Chemistry*, 7:1339-1347 (1999).
Bedwell et al., *Nat. Med*, "Suppression of a CFTR premature stop mutation in a bronchial epithelial cell line", 3:1280-1284 (1997).
Howard et al., "Aminoglycoside antibiotics restore CFTR function by overcoming premature stop mutations", *Nat. Med.* 2:467-469 (1996).
Nakao K, et al., "Quantitative Structure-Activity Analyses of Novel Hydroxyphenylurea Derivatives as Antioxidants", *Biorganic & Medicinal Chemistry, Elsevier Science Ltd. GB*, 6:6, pp. 849-868 (1998).
Sleat et al., "Aminoglycoside-mediated suppression of nonsense mutations in late infantile neuronal ceroid lipofuscinosis", *Eur. J. Ped. Neurol.* 5:Suppl. A. pp. 57-62 (2001).
Baracu et al., 1977, "Potential Anticancer Agents. XIII—Synthesis of New Aliphatic and Cycloaliphatic N-Nitrosoureas," *Revew Roumaine de Chimie* 22(6):885-898.
Johnston et al., 1966, "The Synthesis of Potential Anticancer Agents. XXXVI. N-Nitrosoureas. II. Haloalkyl Derivatives," *J. Med. Chem.* 9(6):892-910.

* cited by examiner

*Primary Examiner* — Rei-tsang Shiao
(74) *Attorney, Agent, or Firm* — Jones Day

(57) ABSTRACT

The invention encompasses ureido substituted benzoic acid compounds, compositions comprising the compounds and methods for treating or preventing diseases associated with nonsense mutations of mRNA by administering these compounds or compositions.

13 Claims, No Drawings

UREIDO SUBSTITUTED BENZOIC ACID COMPOUNDS AND THEIR USE FOR NONSENSE SUPPRESSION AND THE TREATMENT OF DISEASE

This application is a divisional of U.S. application Ser. No. 11/048,656, filed Jan. 21, 2005, now U.S. Pat. No. 7,405,233 allowed, which claims the benefit of U.S. provisional application No. 60/398,333, filed on Jul. 24, 2002, the disclosures of which are incorporated by reference herein in their entirety.

1. FIELD OF INVENTION

The invention encompasses ureido substituted benzoic acid compounds, compositions comprising the compounds and methods for treating or preventing diseases associated with nonsense mutations of mRNA by administering these compounds or compositions.

2. BACKGROUND OF THE INVENTION

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA. Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed, the completed polypeptide chain is released, and the ribosome subunits are recycled for another round of translation.

Mutations of the DNA sequence in which the number of bases is altered are categorized as insertion or deletion mutations (frameshift mutations) and can result in major disruptions of the genome. Mutations of the DNA that change one base into another are labeled missense mutations and are subdivided into the classes of transitions (one purine to another purine, or one pyrimidine to another pyrimidine) and transversions (a purine to a pyrimidine, or a pyrimidine to a purine).

Insertions, deletions, transition and transversion mutations can all result in a nonsense mutation, or chain termination mutation, in which the base mutation or frameshift mutation changes an amino acid codon into one of the three stop codons. These premature stop codons can produce aberrant proteins in cells as a result of premature translation termination. A nonsense mutation in an essential gene can be lethal and can also result in a number of human diseases, such as, cancers, lysosomal storage disorders, the muscular dystrophies, cystic fibrosis and hemophilia, to name a few.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds known to alter the translation process (for example, cycloheximide or the aminoglycoside antibiotics). The result is that an amino acid will be incorporate into the polypeptide chain, at the site of the nonsense mutation and translation will not prematurely terminate at the nonsense codon. The inserted amino acid will not necessarily be identical to the original amino acid of the wild-type protein, however, many amino acid substitutions do not have a gross effect on protein structure or function. Thus, a protein produced by the suppression of a nonsense mutation would be likely to possess activity close to that of the wild-type protein. This scenario provides an opportunity to treat diseases associated with nonsense mutations by avoiding premature termination of translation through suppression of the nonsense mutation.

The ability of aminoglycoside antibiotics to promote readthrough of eukaryotic stop codons has attracted interest in these drugs as potential therapeutic agents in human diseases caused by nonsense mutations. One disease for which such a therapeutic strategy may be viable is classical late infantile neuronal ceroid lipofuscinosis (LINCL), a fatal childhood neurodegenerative disease with currently no effective treatment. Premature stop codon mutations in the gene CLN2 encoding the lysosomal tripeptidyl-peptidase 1 (TPP-I) are associated with disease in approximately half of children diagnosed with LINCL. The ability of the aminoglycoside gentamicin to restore TPP-I activity in LINCL cell lines has been examined. In one patient-derived cell line that was compound heterozygous for a commonly seen nonsense mutation (Arg208Stop) and a different rare nonsense mutation, approximately 7% of normal levels of TPP-I were maximally restored with gentamicin treatment. These results suggest that pharmacological suppression of nonsense mutations by aminoglycosides or functionally similar pharmaceuticals may have therapeutic potential in LINCL (Sleat et. al., *Eur. J. Ped. Neurol.* 5:Suppl A 57-62 (2001)).

In cultured cells having premature stop codons in the Cystic Fibrosis Transmembrane Conductance Regulator (CFTR) gene, treatment with aminoglycosides led to the production of full length CFTR (Bedwell et. al., *Nat. Med.* 3:1280-1284 (1997); Howard et. al. *Nat. Med.* 2: 467-469 (1996)). In mouse models for Duchenne muscular dystrophy, gentamicin sulfate was observed to suppress translational termination at premature stop codons resulting in full length dystrophin (Barton-Davis et. al., *J. Clin. Invest.* 104:375-381 (1999)). A small increase in the amount of full length dystrophin provided protection against contraction-induced damage in the mdx mice. The amino acid inserted at the site of the nonsense codon was not determined in these studies.

Small molecule therapeutics or prophylactics that suppress premature translation termination by mediating the misreading of the nonsense codon would be useful for the treatment of a number of diseases. The discovery of small molecule drugs, particularly orally bioavailable drugs, can lead to the introduction of a broad spectrum of selective therapeutics or prophylactics to the public which can be used against disease caused by nonsense mutations is just beginning.

Citation of any reference in Section 2 of this application is not an admission that the reference is prior art to the application.

3. SUMMARY OF THE INVENTION

The present invention is based in part on the discovery of small molecules that modulate premature translation termination and nonsense-mediated mRNA decay. The present invention encompasses compounds of formula I, compositions comprising compounds of formula I, and methods of use thereof. Compounds of formula I have the structure:

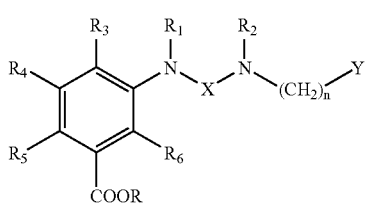

I or a pharmaceutically acceptable salt, hydrate, clathrate, polymorph, prodrug or stereoisomer thereof wherein:

X is C(=O), C(=S), S, S(=O) or S(O)$_2$;

Y is substituted or unsubstituted alkyl, substituted or unsubstituted aryl, substituted or unsubstituted heteroaryl, substituted or unsubstituted cycloalkyl, substituted or unsubstituted heterocyclo;

R is hydrogen, substituted or unsubstituted alkyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl;

n is an integer ranging from 0-4;

$R_1$ and $R_2$ are each independently hydrogen, substituted or unsubstituted alkyl, substituted or unsubstituted alkenyl, substituted or unsubstituted alkynyl, —(CH$_2$)$_m$—W, carboxyalkyl, alkylcarbonyl, alkyloxyalkyl, alkyloxycarbonyl, arylalkyl, sulfonyl, amide or $R_1$ and $R_2$ together with the atoms to which they are attached form an optionally substituted 5-7 membered heterocyclic, an optionally substituted 5-7 membered heteroaryl ring or $R_1$ and $R_2$ together form:

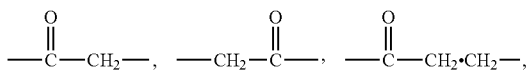

W is at each occurrence independently hydrogen, halogen, hydroxy, alkoxy, carboxy, aldehyde, NH$_2$, NR$^{14}$R$^{14'}$, nitro, cycloalkyl, heteroaryl, heteroarylalkyl;

where (i) each occurrence of R$^{14}$ and R$^{14'}$ is independently selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or CF$_3$; or (ii) R$^{14}$ and R$^{14'}$, together with the nitrogen atom to which they are bonded, join to form an optionally substituted heterocyclic ring containing from 5 to 8 ring atoms of which from 1 to 3 are heteroatoms;

m is an integer ranging from 1-4;

$R_3$—$R_6$ are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl, alkylamino, aminoalkyl, alkoxy, aryloxy, heteroaryloxy, cycloalkoxy, heterocycloalkyloxy, amide, haloalkyl (e.g., CF$_3$), haloalkoxy (e.g., OCF$_3$ or OCHF$_2$), OH, CN, COOH, COOR$^{15}$, SO$_2$R$^{15}$, NO$_2$, NH$_2$, or NR$^{14}$R$^{14'}$ and R$^{15}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl or substituted or unsubstituted heteroaryl or CF$_3$.

The invention further encompasses compounds of formula I, wherein Y is hydrogen, alkyl, amino, nitro or selected from the group:

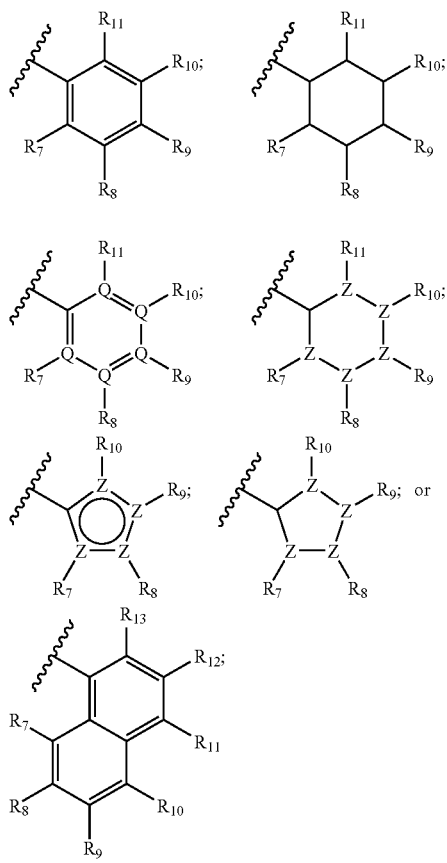

or a pharmaceutically acceptable salt, hydrate, solvate, clathrate, racemate or stereoisomer thereof, wherein:

Q is at each occurrence independently C or N, optionally substituted with $R_7$-$R_{11}$ where appropriate;

Z is at each occurrence independently C, N, O or S, optionally substituted with $R_7$—$R_{11}$ where appropriate;

$R_7$—$R_{13}$ are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl, alkylamino, aminoalkyl, alkoxy, aryloxy, heteroaryloxy, cycloalkoxy, heterocycloalkyloxy, amide, haloalkyl (e.g., $CF_3$), haloalkoxy (e.g., $OCF_3$ or $OCHF_2$), OH, CN, COOH, $COOR^{15}$, $SO_2R^{15}$, $NO_2$, $NH_2$, or $NR^{14}R^{14'}$ wherein $R^{14}$, $R^{14'}$ and $R^{15}$ are as describe above.

The invention encompasses methods for modulating premature translation termination and/or nonsense-mediated mRNA decay. The invention further encompasses a method for suppressing premature translation termination and/or nonsense-mediated mRNA decay in a cell comprising contacting a cell exhibiting premature translation termination and/or nonsense-mediated mRNA decay with an effective amount of a compound of the invention, e.g., formula I. The invention further encompasses a method for inducing nonsense suppression in a cell comprising contacting a cell exhibiting a nonsense mutation with an effective amount of a compound of the invention, e.g., formula I. A nonsense codon can be present in the DNA or RNA of any type of cell and can arise naturally or result from mutagenesis. Accordingly, cells encompassed by the present methods include animal cells, mammalian cells, bacterial cells, plant cells and virally infected cells. In one embodiment, the nonsense codon was present in the progenitor DNA. In another embodiment, the nonsense codon resulted from mutagenesis.

Without being limited by any theory, the ability of the compounds of the invention to promote readthrough of stop codons makes them useful in the treatment or prevention of any disease which is caused in whole or in part by a nonsense mutation. Such diseases can occur due to the decreased amount of active protein produced as a result of premature termination of translation. Without being limited by any theory, the compounds of the invention allow the translation of mRNA to continue past the nonsense mutation resulting in the production of full length protein. A powerful aspect of the invention is that the therapeutic activity of compounds of the invention are not necessarily disease specific, instead are effective at treating of preventing any disease associated with a nonsense mutation. Further, these methods may be patient specific, that is a patient can be screened to determine if their disease is associated with a non-sense mutation. If so, they can then be treated with a compound of the invention.

The compounds of the invention are useful for treating or preventing a number of diseases, such as genetic diseases and non-genetic diseases. Diseases that can be treated or prevented by compounds of the invention include, but are not limited to, cancer, an autoimmune disease, a blood disease, a collagen disease, diabetes, a neurodegenerative disease, a cardiovascular disease, a pulmonary disease, an inflammatory disease, lysosomal storage disease, tuberous sclerosis or central nervous system disease.

3.1 Definitions

As used herein, "premature translation termination" refers to the result of a mutation that changes a codon corresponding to an amino acid to a stop codon.

As used herein, "nonsense-mediated mRNA decay" refers to any mechanism that mediates the decay of mRNAs containing a premature translation termination codon.

As used herein, a "premature termination codon" or "premature stop codon" refers to the occurrence of a stop codon wherein a codon corresponding to an amino acid should be.

As used herein, a "nonsense mutation" is a point mutation changing a codon corresponding to an amino acid to a stop codon.

As used herein, "nonsense suppression" refers to the inhibition or suppression of premature translation and/or nonsense-mediated mRNA decay.

As used herein, "modulation of premature translation termination and/or nonsense-mediated mRNA decay" refers to the regulation of gene expression by altering the level of nonsense suppression. For example, if it is desirable to increase production of a defective protein encoded by a gene with a premature stop codon, i.e., to permit readthrough of the premature stop codon of the disease gene so translation of the gene can occur, then modulation of premature translation termination and/or nonsense-mediated mRNA decay entails up-regulation of nonsense suppression. Conversely, if it is desirable to promote the degradation of an mRNA with a premature stop codon, then modulation of premature translation termination and/or nonsense-mediated mRNA decays entails down-regulation of nonsense suppression.

As used herein, the term "disease" means a condition in the patient.

As used herein, the term "patient" means an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is an infant, child, adolescent or adult. In one embodiment, it has been determined through pre-screening that the patient possesses a non-sense mutation. In another embodiment, it has been determined through pre-screening which non-sense mutation the patient has (i.e., UAA, UGA, or UAG). In another embodiment, the patient is infected with bacterial cells (e.g., *Pseudomonas aeruginosa*). In another embodiment, the cells of the patient are virally infected.

As used herein, unless otherwise specified, the term "substituted" means a group substituted by one to four or more substituents, such as, alkyl, alkenyl, alkynyl, cycloalkyl, aroyl, halo, haloalkyl (e.g., trifluoromethyl), haloalkoxy (e.g., trifluoromethoxy), hydroxy, alkoxy, cycloalkyloxy, heterocylooxy, oxo, alkanoyl, aryl, arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino (in which the two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido (e.g., $SO_2NH_2$), substituted sulfonamido, nitro, cyano, carboxy, carbamyl (e.g., $CONH_2$), substituted carbamyl (e.g., CONH-alkyl, CONH-aryl, CONH-arylalkyl or instances where there are two substituents on the nitrogen selected from alkyl or arylalkyl), alkoxycarbonyl, aryl, substituted aryl, guanidino, substituted or unsubstituted heterocycloalkyl, substituted or unsubstituted heteroaryl (such as, indolyl, imidazolyl, furyl, thienyl, thiazolyl, pyrrolidyl, pyridyl, pyrimidyl and the like). In one embodiment, the substituent is —O-alkyl-C(=O)-heterocyclo (substituted or unsubstituted), wherein alkyl and heterocyclo are defined above. Wherein, as noted above, the substituents themselves are further substituted, such further substituents are selected from the group consisting of halogen, alkyl, alkoxy, aryl, heteroaryl, heterocyclo, cycloalkyl, and arylalkyl.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-dimethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, unless otherwise specified the term "alkenyl group" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched $(C_2-C_{10})$alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, unless otherwise specified the term "alkynyl group" means a straight chain or branched non-cyclic hydrocarbon having from 2 to 20 carbon atoms, more preferably 2-10 carbon atoms, most preferably 2-6 carbon atoms, and including at lease one carbon-carbon triple bond. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, unless otherwise specified the term "halogen" or "halo" means fluorine, chlorine, bromine, or iodine.

As used herein, unless otherwise specified the term "haloalkyl" means -alkyl substituted with one or more halogens, wherein alkyl and halogen are defined as above, including —$CF_3$, —$CHF_2$, —$CH_2F$, —$CCl_3$, —$CHCl_2$, —$CBr_3$, —$CHBr_2$, —$CH_2CF_3$, —$CH_2CHF_2$, —$CH_2CH_2F$, and the like.

As used herein, unless otherwise specified the term "alkyl sulfonyl" means —$SO_2$-alkyl, wherein alkyl is defined as above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

As used herein, unless otherwise specified the term "sulfonyl alkyl" means -alkyl-$SO_3H$, wherein alkyl is defined as above, including —$CH_3$—$SO_3H$, —$CH_2CH_2$—$SO_3H$, —$(CH_2)_3$—$SO_3H$, —$(CH_2)_4$—$SO_3H$, and the like.

As used herein, unless otherwise specified the term "carboxyl" and "carboxy" mean —COOH or a salt thereof (e.g., —$COO^-Na^+$).

As used herein, unless otherwise specified the term "alkoxy" means —O-(alkyl), wherein alkyl is defined above, including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

As used herein, unless otherwise specified the term "haloalkoxy" means -alkoxy substituted with one or more halogens, wherein alkoxy and halogen are defined as above, including —$OCF_3$, —$OCHF_2$, —$OCH_2F$, —$OCCl_3$, —$OCHCl_2$, —$OCBr_3$, —$OCHBr_2$, —$OCH_2CF_3$, —$OCH_2CHF_2$, —$OCH_2CH_2F$, and the like.

As used herein, unless otherwise specified the term "alkoxycarbonyl" means —C(=O)O-(alkyl), wherein alkyl is defined above, including —C(=O)O—$CH_3$, —C(=O)O—$CH_2CH_3$, —C(=O)O—$(CH_2)_2CH_3$, —C(=O)O—$(CH_2)_3CH_3$, —C(=O)O—$(CH_2)_4CH_3$, —C(=O)O—$(CH_2)_5CH_3$, and the like. In a preferred embodiment, the esters are biohydrolyzable (i.e., the ester is hydrolyzed to a carboxylic acid in vitro or in vivo).

As used herein, unless otherwise specified the term "alkylcarbonyl" means —C(=O)=(alkyl), wherein alkyl is defined above, including —C(=O)—$CH_3$, —C(=O)—$CH_2CH_3$, —C(=O)—$(CH_2)_2CH_3$, —C(=O)—$(CH_2)_3CH_3$, —C(=O)—$(CH_2)_4CH_3$, —C(=O)—$(CH_2)_5CH_3$, and the like.

As used herein, unless otherwise specified the term "carboxyalkyl" means -(alkyl)-carboxy, wherein alkyl and carboxy are defined above, including —$CH_2$—COOH, —$(CH_2)_2$—COOH, —$(CH_2)_3$—COOH, —$(CH_2)_4$—COOH, and the like.

As used herein, unless otherwise specified the term "alkoxyalkyl" means -(alkyl)-O-(alkyl), wherein each "alkyl" is independently an alkyl group as defined above, including —$CH_2OCH_3$, —$CH_2OCH_2CH_3$, —$(CH_2)_2OCH_2CH_3$, —$(CH_2)_2O(CH_2)_2CH_3$, and the like.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricylcic compounds as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocyclic moities. Representative heteroaryls are triazolyl, tetrazolyl, oxadiazolyl, pyridyl, furyl, benzofuranyl, thiophenyl, thiazolyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl, oxazolyl, benzo[1,3]dioxole and 2,3-dihydrobenzo[1,4]dioxine. A group can be unsubstituted or substituted.

As used herein, unless otherwise specified the term "aryloxy" means —O-aryl group, wherein aryl is as defined above, including, but not limited to —O-phenyl, —O-tolyl, —O-anthracenyl, —O-fluorenyl, —O-indenyl, —O-azulenyl, —O-phenanthrenyl and —O-naphthyl. An aryloxy group can be unsubstituted or substituted.

As used herein, unless otherwise specified the term "arylalkyl" means -(alkyl)-(aryl), wherein alkyl and aryl are defined above, including, but not limited to —$(CH_2)$phenyl, —$(CH_2)_2$phenyl, —$(CH_2)_3$phenyl, —CH(phenyl)$_2$, —CH(phenyl)$_3$, —$(CH_2)$tolyl, —$(CH_2)$anthracenyl, —$(CH_2)$fluorenyl, —$(CH_2)$indenyl, —$(CH_2)$azulenyl, —$(CH_2)$naphthyl, and the like.

As used herein, unless otherwise specified the term "alkylaryl" means -(aryl)-(alkyl), wherein aryl and aryl are defined above, including, but not limited to -phenyl-$(CH_3)_5$, phenyl-$(CH_3)_4$, phenyl-$(CH_3)_3$, phenyl-$(CH_3)_2$, phenyl-$(CH_3)$, -phenyl-$(CH_2CH_3)_5$, phenyl-$(CH_2CH_3)_4$, phenyl-$(CH_2CH_3)_3$, phenyl-$(CH_2CH_3)_2$, phenyl-$(CH_2CH_3)$, 2-methyl-phenyl, 3-methyl-phenyl, 4-methyl-phenyl, 5-methyl-phenyl, 2,3-dimethylphenyl, 2,4-dimethyl-phenyl, 2,5-dimethylphenyl, 3,4-dimethyl-phenyl, 3,5-dimethyl-phenyl, 2-ethyl-phenyl, 3-ethyl-phenyl, 4-ethyl-phenyl, 5-ethyl-phenyl, 2-isopropyl-phenyl, 3-isopropyl-phenyl, 4-isopropyl-phenyl, 5-isopropyl-phenyl, 4-isopropyl-3-methyl-phenyl, 3-isopropyl-5-methyl-phenyl and the like, where each alkyl group can be further substituted.

As used herein, unless otherwise specified the term "heteroarylalkyl" means -(alkyl)-(heteroaryl), wherein alkyl and heteroaryl are defined above, including, but not limited to, —$(CH_2)$pyridyl, —$(CH_2)_2$ pyridyl, —$(CH_2)_3$ pyridyl, —CH(pyridyl)$_2$, —C(pyridyl)$_3$, —$(CH_2)$triazolyl, —$(CH_2)$thiazolyl, —$(CH_2)$tetrazolyl, —$(CH_2)$oxadiazolyl, —$(CH_2)$furyl, —$(CH_2)$benzofuranyl, —$(CH_2)$thiophenyl, —$(CH_2)$benzothiophenyl, and the like.

As used herein, unless otherwise specified the term "alkylheteroaryl" means -(heteroaryl)-(alkyl), wherein heteroaryl and alkyl are defined above, including, but not limited to, -pyridyl-$(CH_3)$, -triazolyl-$(CH_3)$, -thiazolyl-$(CH_3)$, -tetrazolyl-$(CH_3)$, -oxadiazolyl-$(CH_3)$, -furyl-$(CH_3)$, -benzofuranyl-$(CH_3)$, -thiophenyl-$(CH_3)$, -benzothiophenyl-$(CH_3)$, and the like wherein each alkyl group can be further substituted.

As used herein, unless otherwise specified the term "arylalkyloxy" means —O-(alkyl)-(aryl), wherein alkyl and aryl are defined above, including, but not limited to —O—$(CH_2)_2$phenyl, —O—$(CH_2)_3$phenyl, —O—CH(phenyl)$_2$, —O—CH(phenyl)$_3$, —O—$(CH_2)$tolyl, —O—$(CH_2)$anthracenyl, —O—$(CH_2)$fluorenyl, —O—$(CH_2)$indenyl, —O—$(CH_2)$azulenyl, —O—$(CH_2)$naphthyl, and the like.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Examples of cycloalkyl groups include, but are not limited to, $(C_3-C_7)$cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified the terms "heterocyclyl" and "heterocyclo" mean a monocyclic or polycyclic ring comprising carbon and hydrogen atoms, optionally having 1 or 2 multiple bonds, and the ring atoms contain at least one heteroatom, preferably 1 to 3 heteroatoms, independently selected from nitrogen, oxygen, and sulfur. Heterocyclyl ring structures include, but are not limited to compounds having one or more ring structures such as mono-, bi-, or trycylic compounds. Preferably, the heterocyclyl group is a monocyclic ring or bicyclic ring. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. A heterocyclyl ring can be unsubstituted or substituted.

As used herein, unless otherwise specified the term "cycloalkyloxy" means —O-(cycloalkyl), wherein cycloalkyl is defined above, including —O-cyclopropyl, —O-cyclobutyl, —O-cyclopentyl, —O-cyclohexyl, —O-cycloheptyl and the like.

As used herein, unless otherwise specified the term "cycloalkylalkyl" means -(alkyl)-(cycloalkyl), wherein cycloalkyl and alkyl are defined above, including, but not limited to —$CH_2$-cyclopropyl, —$CH_2$-cyclobutyl, —$CH_2$-cyclopentyl, —$(CH_2)_2$-cyclohexyl, —$(CH_2)_3$-cyclohexyl, —$(CH_2)_4$-cyclohexyl, —$CH_2$-cycloheptyl and the like.

As used herein, unless otherwise specified the term "heterocycloalkyl" means -(alkyl)-(heterocyclo), wherein heterocyclo and alkyl are defined above, including, but not limited to —$CH_2$-morpholinyl, —$CH_2$-pyrrolidinonyl, —$CH_2$-pyrrolidinyl, —$(CH_2)_2$-piperidinyl, —$(CH_2)_3$-piperidinyl, —$(CH_2)_4$-piperidinyl, —$CH_2$-hydantoinyl and the like.

As used herein, unless otherwise specified the term "cycloalkylalkyloxy" means —O-(alkyl)-(cycloalkyl), wherein cycloalkyl and alkyl are defined above, including, but not limited to —O—$CH_2$-cyclopropyl, —O—$CH_2$-cyclobutyl, —O—$CH_2$-cyclopentyl, —O—$(CH_2)_2$-cyclohexyl, —O—$(CH_2)_3$-cyclohexyl, —O—$(CH_2)_4$-cyclohexyl, —O—$CH_2$-cycloheptyl and the like.

As used herein, unless otherwise specified the term "heterocycloalkyloxy" means —O-(alkyl)-(heterocyclo), wherein heterocyclo and alkyl are defined above, including, but not limited to —O—$CH_2$-morpholinyl, —O—$CH_2$-pyrrolidinonyl, —O—$CH_2$-pyrrolidinyl, —O—$(CH_2)_2$-piperidinyl, —O—$(CH_2)_3$-piperidinyl, —O—$(CH_2)_4$-piperidinyl, —O—$CH_2$-hydantoinyl and the like.

As used herein, unless otherwise specified the term "aminoalkoxy" means —O-(alkyl)-$NH_2$, wherein alkyl is defined above, including, but not limited to —O—$CH_2$—$NH_2$, —O—$(CH_2)_2$—$NH_2$, —O—$(CH_2)_3$—$NH_2$, —O—$(CH_2)_4$—$NH_2$, —O—$(CH_2)_5$—$NH_2$, and the like.

As used herein, unless otherwise specified the term "alkylamino" means —NH(alkyl) or —N(alkyl)(alkyl), wherein alkyl is defined above, including, but not limited to $NHCH_3$, —$NHCH_2CH_3$, —$NH(CH_2)_2CH_3$, —$NH(CH_2)_3CH_3$, —$NH(CH_2)_4CH_3$, —$NH(CH_2)_5CH_3$, —$N(CH_3)_2$, —$N(CH_2CH_3)_2$, —$N((CH_2)_2CH_3)_2$, —$N(CH_3)(CH_2CH_3)$, and the like.

As used herein, unless otherwise specified the term "arylamino" means —NH(aryl), wherein aryl is defined above, including, but not limited to —NH(phenyl), —NH(tolyl), —NH(anthracenyl), —NH(fluorenyl), —NH(indenyl), —NH(azulenyl), —NH(pyridinyl), —NH(naphthyl), and the like.

As used herein, unless otherwise specified the term "arylalkylamino" means —NH-(alkyl)-(aryl), wherein alkyl and aryl are defined above, including, but not limited to —NH—

CH$_2$-(phenyl), —NH—CH$_2$-(tolyl), —NH—CH$_2$-(anthracenyl), —NH—CH$_2$-(fluorenyl), —NH—CH$_2$-(indenyl), —NH—CH$_2$-(azulenyl), —NH—CH$_2$-(pyridinyl), —NH—CH$_2$-(naphthyl), —NH—(CH$_2$)$_2$-(phenyl) and the like.

As used herein, unless otherwise specified the term "cycloalkylamino" means —NH-(cycloalkyl), wherein cycloalkyl is defined above, including, but not limited to —NH-cyclopropyl, —NH-cyclobutyl, —NH-cyclopentyl, —NH-cyclohexyl, —NH-cycloheptyl, and the like.

As used herein, unless otherwise specified the term "aminoalkyl" means -(alkyl)-NH$_2$, wherein alkyl is defined above, including, but not limited to —CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$ and the like.

As used herein, unless otherwise specified the term "alkylaminoalkyl" means -(alkyl)-NH(alkyl) or -(alkyl)-N(alkyl)(alkyl), wherein each "alkyl" is independently an alkyl group defined above, including, but not limited to —CH$_2$—NH—CH$_3$, —CH$_2$—NHCH$_2$CH$_3$, —CH$_2$—NH(CH$_2$)$_2$CH$_3$, —CH$_2$—NH(CH$_2$)$_3$CH$_3$, —CH$_2$—NH(CH$_2$)$_4$CH$_3$, —CH$_2$—NH(CH$_2$)$_5$CH$_3$, —(CH$_2$)$_2$—NH—CH$_3$, —CH$_2$—N(CH$_3$)$_2$, —CH$_2$—N(CH$_2$CH$_3$)$_2$, —CH$_2$—N((CH$_2$)$_2$CH$_3$)$_2$, —CH$_2$—N(CH$_3$)(CH$_2$CH$_3$), —(CH$_2$)$_2$—N(CH$_3$)$_2$, and the like.

As used herein, a "therapeutically effective amount" refers to that amount of the compound of the invention or other active ingredient sufficient to provide a therapeutic benefit in the treatment or management of the disease or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, a "prophylactically effective amount" refers to that amount of a compound of the invention or other active ingredient sufficient to result in the prevention, recurrence or spread of the disease. A prophylactically effective amount may refer to the amount sufficient to prevent initial disease, the recurrence or spread of the disease or the occurrence of the disease in a patient, including but not limited to those predisposed to the disease. A prophylactically effective amount may also refer to the amount that provides a prophylactic benefit in the prevention of the disease. Further, a prophylactically effective amount with respect to a compound of the invention means that amount alone, or in combination with other agents, that provides a prophylactic benefit in the prevention of the disease. Used in connection with an amount of a compound of the invention, the term can encompass an amount that improves overall prophylaxis or enhances the prophylactic efficacy of or synergies with another prophylactic agent.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens.

As used herein, "in combination" refers to the use of more than one prophylactic and/or therapeutic agents.

As used herein, the terms "manage", "managing" and "management" refer to the beneficial effects that a subject derives from a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the onset, recurrence or spread of the disease in a subject resulting from the administration of a prophylactic or therapeutic agent.

As used herein, the terms "treat", "treating" and "treatment" refer to the eradication or amelioration of the disease or symptoms associated with the disease. In certain embodiments, such terms refer to minimizing the spread or worsening of the disease resulting from the administration of one or more prophylactic or therapeutic agents to a subject with such a disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "polymorph" refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the terms "biohydrolyzable amide," "biohydrolyzable ester," "biohydrolyzable carbamate," "biohydrolyzable carbonate," "biohydrolyzable ureido," "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "optically pure" or "stereomerically pure" means one stereoisomer of a compound is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

4. DETAILED DESCRIPTION OF THE INVENTION

4.1 Compounds of the Invention

As stated above, the present invention encompasses compounds of formula I below, compositions comprising compounds of formula I, and methods of using these compounds and compositions.

Compounds of formula I have the structure:

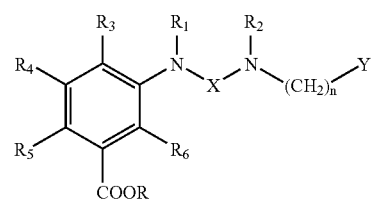

I or a pharmaceutically acceptable salt, hydrate, clathrate, polymorph, prodrug or stereoisomer thereof wherein:

X is C(=O), C(=S), S, S(=O) or S(O)$_2$;

Y is substituted or unsubstituted alkyl, substituted or unsubstituted aryl, substituted or unsubstituted heteroaryl, substituted or unsubstituted cycloalkyl, substituted or unsubstituted heterocyclo;

R is hydrogen, substituted or unsubstituted alkyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl;

n is an integer ranging from 0-4;

R$_1$ and R$_2$ are each independently hydrogen, substituted or unsubstituted alkyl, substituted or unsubstituted alkenyl, substituted or unsubstituted alkynyl, —(CH$_2$)$_m$—W, carboxyalkyl, alkylcarbonyl, alkyloxyalkyl, alkyloxycarbonyl, arylalkyl, sulfonyl, amide or R$_1$ and R$_2$ together with the atoms to which they are attached form an optionally substituted 5-7 membered heterocyclic, an optionally substituted 5-7 membered heteroaryl ring or R$_1$ and R$_2$ together form:

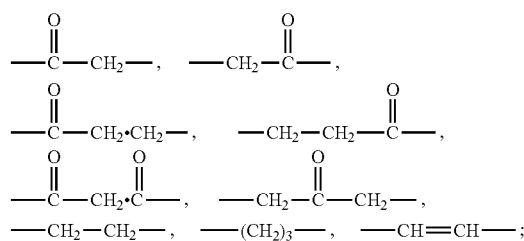

W is at each occurrence independently hydrogen, halogen, hydroxy, alkoxy, carboxy, aldehyde, $NH_2$, $NR^{14}R^{14'}$, nitro, cycloalkyl, heteroaryl, heteroarylalkyl;

where (i) each occurrence of $R^{14}$ and $R^{14'}$ is independently selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or $CF_3$; or (ii) $R^{14}$ and $R^{14'}$, together with the nitrogen atom to which they are bonded, join to form an optionally substituted heterocyclic ring containing from 5 to 8 ring atoms of which from 1 to 3 are heteroatoms;

m is an integer ranging from 1-4;

$R_3$—$R_6$ are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl, alkylamino, aminoalkyl, alkoxy, aryloxy, heteroaryloxy, cycloalkoxy, heterocycloalkyloxy, amide, haloalkyl (e.g., $CF_3$), haloalkoxy (e.g., $OCF_3$ or $OCHF_2$), OH, CN, COOH, $COOR^{15}$, $SO_2R^{15}$, $NO_2$, $NH_2$, or $NR^{14}R^{14'}$ and $R^{15}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or $CF_3$.

In a preferred embodiment, R is group that is biohydrolyzable. In a more preferred embodiment R is H.

In another preferred embodiment, $R_1$ and $R_2$ together form:

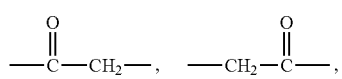

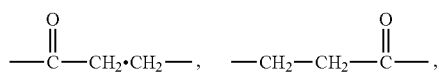

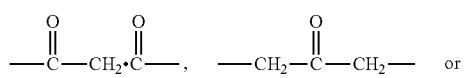

In another preferred embodiment, $R_1$ and $R_2$ together form —$CH_2$—$CH_2$—.

In another preferred embodiment, $R_1$ and $R_2$ together with the atoms to which they are attached form a substituted 5-membered heterocyclic ring, wherein the heterocyclic ring is substituted with a gem dimethyl group.

In another preferred embodiment, $R_1$ and $R_2$ together with the atoms to which they are attached form a 6-membered heterocyclic ring.

The invention further encompasses compounds of formula I, wherein Y is hydrogen, alkyl, amino, nitro or selected from the group:

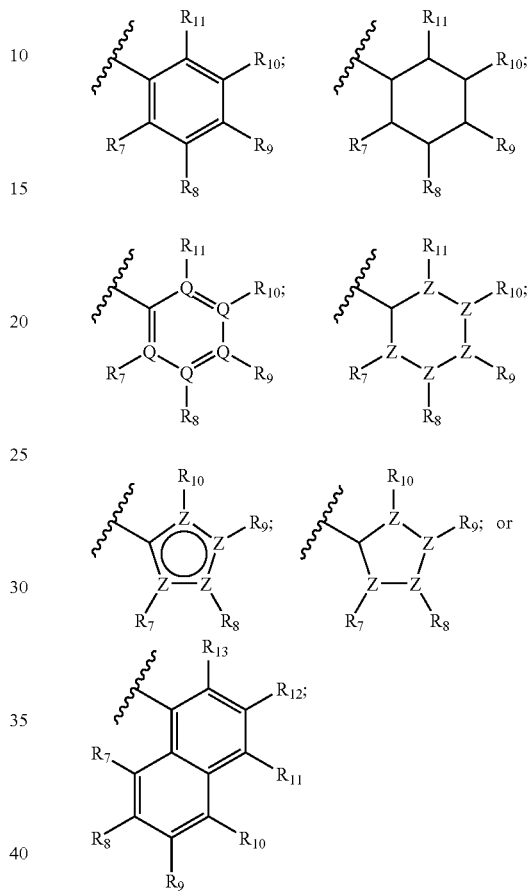

or a pharmaceutically acceptable salt, hydrate, clathrate, polymorph, prodrug or stereoisomer thereof wherein:

Q is at each occurrence independently C or N, optionally substituted with $R_7$-$R_{11}$ where appropriate;

Z is at each occurrence independently C, N, O or S, optionally substituted with $R_7$—$R_{11}$ where appropriate;

$R_7$—$R_{13}$ are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl, alkylamino, aminoalkyl, alkoxy, aryloxy, heteroaryloxy, cycloalkoxy, heterocycloalkyloxy, amide, haloalkyl (e.g., $CF_3$), haloalkoxy (e.g., $OCF_3$ or $OCHF_2$), OH, CN, COOH, $COOR^{15}$, $SO_2R^{15}$, $NO_2$, $NH_2$, or $NR^{14}R^{14'}$ wherein $R^{14}$, $R^{14'}$ and $R^{15}$ are as described above.

In a preferred embodiment, 1 to 3 of Q are N and the rest are C. In another preferred embodiment, 1 to 3 of Z are N, O or S and the rest are C.

In another preferred embodiment, $R_9$ is alkyl, preferably substituted alkyl and most preferably isopropyl.

The invention further encompasses compounds of formula I, wherein Y is selected from the group:

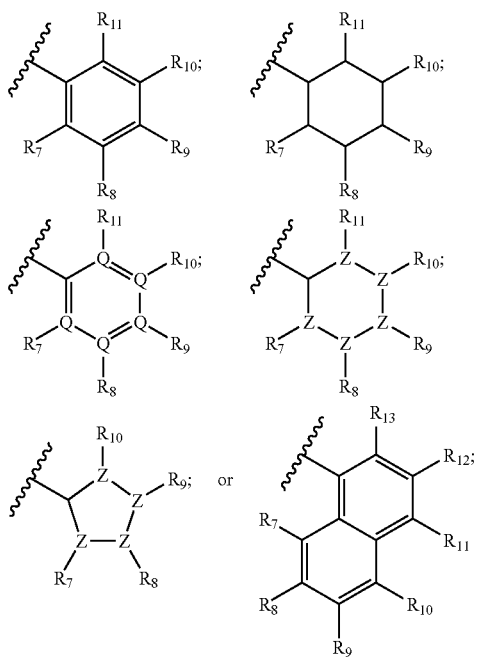

or a pharmaceutically acceptable salt, hydrate, clathrate, polymorph, prodrug or stereoisomer thereof wherein:

Q is at each occurrence independently C or N, optionally substituted with $R_7$-$R_{11}$ where appropriate;

Z is at each occurrence independently C, N, O or S, optionally substituted with $R_7$—$R_{11}$ where appropriate;

In a preferred embodiment, $R_9$ is alkyl, preferably substituted alkyl and most preferably isopropyl.

In one embodiment, Y is

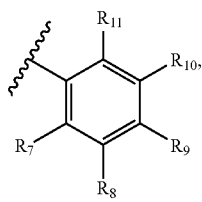

wherein $R_7$ and $R_{11}$ are hydrogen and $R_8$—$R_{10}$ are independently hydrogen, substituted or unsubstituted alkyl, substituted or unsubstituted alkenyl, substituted or unsubstituted alkynyl; substituted or unsubstituted cycloalkyl, substituted or unsubstituted heterocyclo, substituted or unsubstituted cycloalkylalkyl, substituted or unsubstituted heterocycloalkyl, substituted or unsubstituted aryl, substituted or unsubstituted heteroaryl, alkoxy, aryloxy, heteroaryloxy, cycloalkoxy, heterocycloalkyloxy, amide, halogen, $CF_3$, $OCF_3$, $OCHF_2$, OH, CN, COOH, $COOR^{15}$, $SO_2R^{15}$, $NO_2$, $NH_2$, or $NR^{14}R^{14'}$ where $R^{14}$, $R^{14'}$ and $R^{15}$ are as described above; or $R_9$ and $R_{10}$ taken together form an optionally substituted saturated or unsaturated heterocyclic ring containing from 5 to 8 ring atoms of which from 1 to 3 are heteroatoms. In a particular embodiment, $R_9$ and $R_{10}$ taken together form a substituted or unsubstituted dioxolane or dioxane ring fused to benzene.

In a preferred embodiment, only one of $R_7$—$R_{11}$ is other than hydrogen, preferably the substituent other than hydrogen is a meta or para substituent, more preferably halogen, most preferably fluorine. In another preferred embodiment, two of $R_7$—$R_{11}$ are other than hydrogen, wherein both are meta substituted, or one is meta substituted and the other is para substituted. Preferably, $R_8$—$R_{10}$ are independently hydrogen, halogen, substituted or unsubstituted alkyl, substituted or unsubstituted alkoxy, wherein $R_8$—$R_{10}$ are preferably substituted with halogen, more preferably substituted with fluorine.

In another embodiment, the compounds of formula I include compounds of the formula:

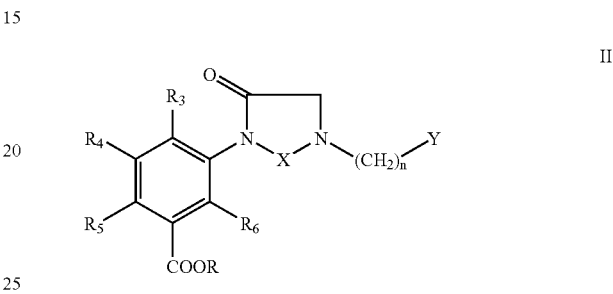

II wherein Y is preferably substituted or unsubstituted aryl, substituted or unsubstituted heteroaryl, substituted or unsubstituted heterocyclo or substituted or unsubstituted cyclohexyl. In yet another preferred embodiment wherein the compounds is one of formula II, R is H.

In another preferred embodiment, the compound of formula II is that wherein $R_3$—$R_8$, $R_{10}$ and $R_{11}$ are H and $R_9$ is substituted or unsubstituted alkyl, substituted or unsubstituted aryl, aryloxy, cycloalkyl, alkoxy, halogen, haloalkoxy or alkoxycarbonyl.

In another preferred embodiment, the compound of formula II is that wherein $R_3$—$R_6$ and $R_8$—$R_{10}$ are H and one of $R_7$ or $R_{11}$ is halogen and the other is H.

In another preferred embodiment, the compound of formula II is that wherein $R_3$—$R_7$, $R_9$ and $R_{11}$ are H and one of $R_8$ or $R_{10}$ is halogen or haloalkyl and the other is H.

In another preferred embodiment, the compound of formula II is that wherein $R_3$—$R_7$ and $R_{11}$ are H, $R_9$ is alkoxy and one of $R_8$ or $R_{10}$ is alkoxy and the other is H.

In another embodiment, the compounds of formula I include compounds of the formula:

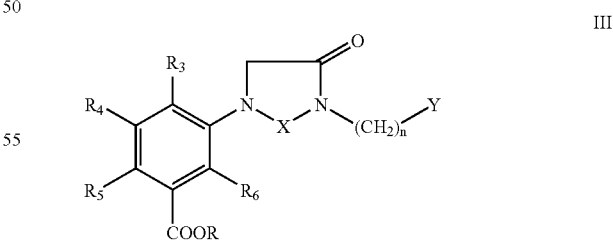

III wherein Y is preferably substituted or unsubstituted aryl or substituted or unsubstituted heteroaryl. In yet another preferred embodiment wherein the compounds is one of formula III, R is H.

In another preferred embodiment, the compound of formula III is that wherein $R_3$—$R_8$, $R_{10}$ and $R_{11}$ are H and $R_9$ is alkyl, aryloxy or alkoxycarbonyl.

In another preferred embodiment, the compound of formula III is that wherein $R_3$—$R_6$ and $R_8$—$R_{10}$ are H and one of $R_7$ or $R_{11}$ is halogen and the other is H.

In another preferred embodiment, the compound of formula III is that wherein $R_3$—$R_7$, $R_9$ and $R_{11}$ are H and one of $R_8$ or $R_{10}$ is alkoxy and the other is H.

In another preferred embodiment, the compound of formula III is that wherein $R_3$—$R_9$ are H and $R_{10}$ and $R_{11}$ are halogen.

In another preferred embodiment, the compound of formula III is that wherein $R_3$—$R_6$ and $R_9$—$R_{11}$ are H and $R_7$ and $R_8$ are halogen.

In another embodiment, the compounds of formula I include compounds of the formula:

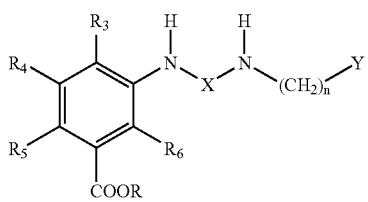

IV wherein Y is preferably substituted or unsubstituted aryl or substituted or unsubstituted heteroaryl. In yet another preferred embodiment wherein the compounds is one of formula IV, R is H.

In another preferred embodiment, the compound of formula IV is that wherein $R_3$—$R_8$, $R_{10}$ and $R_{11}$ are H and $R_9$ is alkyl or halogen.

In another preferred embodiment, the compound of formula IV is that wherein $R_3$—$R_6$, $R_8$ and $R_{10}$ are H, $R_9$ is halogen, and one of $R_7$ or $R_{11}$ is halogen and the other is H.

In another embodiment, the compounds of formula I include compounds of the formula:

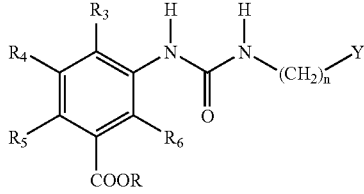

V wherein Y is preferably substituted or unsubstituted aryl or substituted or unsubstituted heteroaryl. In yet another preferred embodiment wherein the compounds is one of formula V, R is H.

In another preferred embodiment, the compound of formula V is that wherein $R_3$—$R_8$, $R_{10}$ and $R_{11}$ are H and $R_9$ is alkyl or halogen.

In another preferred embodiment, the compound of formula V is that wherein $R_3$—$R_6$, $R_8$ and $R_{10}$ are H, $R_9$ is halogen, and one of $R_7$ or $R_{11}$ is halogen and the other is H.

In another embodiment, the compounds of formula I include compounds of the formula:

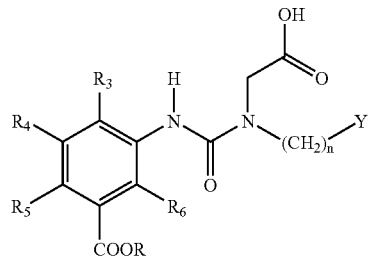

VI wherein Y is preferably substituted or unsubstituted aryl or substituted or unsubstituted heteroaryl. In yet another preferred embodiment wherein the compounds is one of formula VI, R is H.

In another preferred embodiment, the compound of formula VI is that wherein $R_3$—$R_8$, $R_{10}$ and $R_{11}$ are H and $R_9$ is alkyl.

In another preferred embodiment, the compound of formula VI is a pharmaceutically acceptable salt, e.g., a monosodium salt or disodium salt when R is H.

In another embodiment, the compounds of formula I include compounds of the formula:

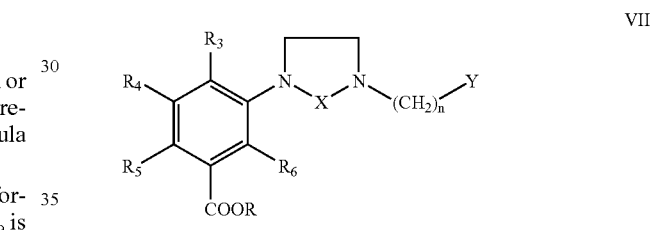

VII wherein X is C(=O), C(=S) or S(O)$_2$ and Y is preferably substituted or unsubstituted aryl, substituted or unsubstituted heteroaryl, substituted or unsubstituted heterocyclo and $R_7$—$R_{11}$ are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted heterocyclo, substituted or unsubstituted aryl, substituted or unsubstituted heteroaryl, alkylamino, aminoalkyl, alkoxy, aryloxy, heteroaryloxy, cycloalkoxy, heterocycloalkyloxy, amide, haloalkyl (e.g., CF$_3$), haloalkoxy (e.g., OCF$_3$ or OCHF$_2$), OH, CN, COOH, COOR$^{15}$, SO$_2$R$^{15}$, NO$_2$, NH$_2$, or NR$^{14}$R$^{14'}$ where R$^{14}$, R$^{14'}$ and R$^{15}$ are described above.

In preferred embodiment, the compound of formula VII is that wherein R is H.

In another preferred embodiment, the compound of formula VII is that wherein only one of $R_7$—$R_{11}$ is other than hydrogen and preferably is a meta or para substituent. In another preferred embodiment, the compound of formula VII is that wherein two of $R_7$—$R_{11}$ are other than hydrogen and preferably are both meta substituents or meta and para substituents.

In another preferred embodiment, the compound of formula VII is that wherein $R_3$—$R_8$, $R_{10}$ and $R_{11}$ are H and $R_9$ is substituted or unsubstituted alkyl (e.g., methyl, ethyl, propyl, isopropyl, butyl, isobutyl or t-butyl), halogen, haloalkyl (e.g., fluoro substituted alkyl), alkoxy, haloalkoxy (e.g., fluoro substituted alkoxy), substituted or unsubstituted heterocyclo (e.g., pyrrolidine or piperidine), substituted or unsubstituted heteroaryl (e.g., pyrrole), alkylamino (e.g., dimethylamino) or —O-alkyl-C(=O)-heterocyclo (substituted or unsubstituted).

In another preferred embodiment, the compound of formula VII is that wherein $R_3$—$R_7$, $R_9$ and $R_{11}$ are H and $R_8$ and $R_{10}$ are halogen.

In another preferred embodiment, the compound of formula VII is that wherein $R_3$—$R_6$, $R_8$, $R_9$ and $R_{11}$ are H and $R_7$ and $R_{10}$ are halogen.

In another preferred embodiment, the compound of formula VII is that wherein $R_3$—$R_6$ and $R_8$—$R_{10}$ are H and one of $R_7$ or $R_{11}$ is halogen and the other is H.

In another preferred embodiment, the compound of formula VII is that wherein $R_3$—$R_7$, $R_9$ and $R_{11}$ are H and one of $R_8$ or $R_{10}$ is alkyl or halogen and the other is H.

In another preferred embodiment, the compound of formula VII is that wherein $R_3$—$R_7$ and $R_{11}$ are H, $R_9$ is halogen, one of $R_8$ or $R_{10}$ is halogen, haloalkyl or haloalkoxy and the other is H.

In another preferred embodiment, the compound of formula VII is that wherein $R_3$—$R_7$ and $R_{11}$ are H, $R_9$ is alkyl, one of $R_8$ or $R_{10}$ is halogen and the other is H.

In another preferred embodiment, the compound of formula VII is that wherein $R_3$—$R_6$, $R_8$ and $R_{10}$ are H, $R_9$ is halogen, one of $R_7$ or $R_{11}$ is halogen and the other is H.

In another preferred embodiment, the compound of formula VII is that wherein $R_3$ is alkyl, alkoxy or halogen.

In another preferred embodiment, the compound of formula VII is that wherein $R_5$ is alkoxy or halogen.

In another preferred embodiment, the compound of formula VII is that wherein $R_6$ is halogen.

In another preferred embodiment, the compound of formula VII is that wherein $R_9$ and $R_{10}$ form a substituted or unsubstituted dioxole or dioxine ring.

In another preferred embodiment, the compound of formula VII is that wherein R is H.

In another embodiment, the compounds of formula I include compounds of the formula:

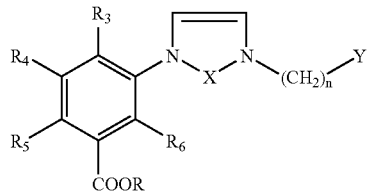

VIII wherein Y is preferably substituted or unsubstituted aryl or substituted or unsubstituted heteroaryl. In yet another preferred embodiment wherein the compounds is one of formula VIII, R is H.

In another preferred embodiment, the compound of formula VIII is that wherein $R_3$—$R_8$, $R_{10}$ and $R_{11}$ are H and $R_9$ is alkyl.

The invention further encompasses compounds of formula I-IV, VII and VIII wherein X is S, S(=O) or S(O)$_2$.

The invention further encompasses compounds of formula I-VIII wherein n is 0 or 1.

The invention further encompasses compounds of formula I-VIII wherein at least one of $R_3$—$R_6$ is hydrogen.

The invention further encompasses compounds of formula I-VIII wherein at least two of $R_3$—$R_6$ are hydrogen.

The invention further encompasses compounds of formula I-VIII wherein at least three of $R_3$—$R_6$ are hydrogen.

The invention further encompasses compounds of formula I-VIII wherein $R_3$—$R_6$ are hydrogen.

The invention is also directed to compounds having the structure:

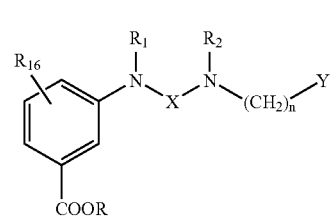

IX or a pharmaceutically acceptable salt, hydrate, clathrate, polymorph, prodrug or stereoisomer thereof wherein:

X is C(=O), C(=S), S, S(=O) or S(O)$_2$;

Y is:

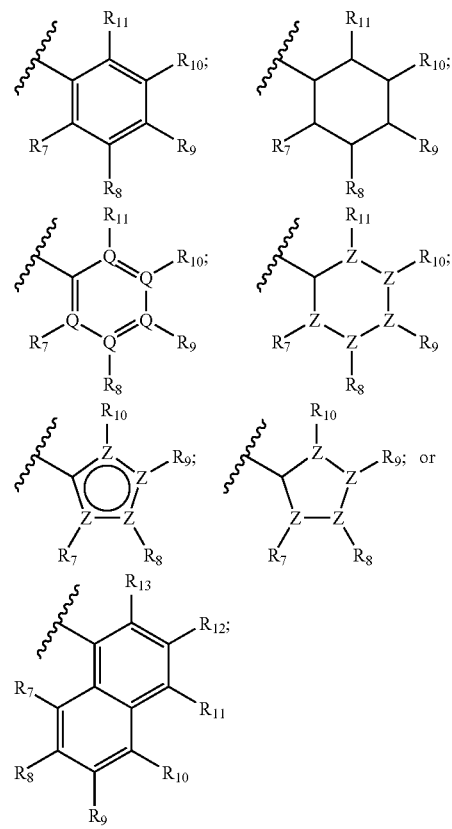

Q is at each occurrence independently C or N, optionally substituted with $R_7$-$R_{11}$ where appropriate;

Z is at each occurrence independently C, N, O or S, optionally substituted with $R_7$—$R_{11}$ where appropriate;

R is hydrogen, substituted or unsubstituted alkyl, substituted or unsubstituted cycloalkyl, substituted or unsubstituted heterocyclo, substituted or unsubstituted aryl, substituted or unsubstituted heteroaryl;

n is an integer ranging from 0-4;

$R_1$ and $R_2$ are each independently hydrogen, substituted or unsubstituted alkyl, substituted or unsubstituted alkenyl, substituted or unsubstituted alkynyl, —(CH$_2$)$_m$—W, carboxyalkyl, alkylcarbonyl, alkyloxyalkyl, alkyloxycarbonyl, arylalkyl, or $R_1$ and $R_2$ together with the atoms to which they are attached form an optionally substituted 5-7 membered heterocyclic, or heteroaryl ring or $R_1$ and $R_2$ together form:

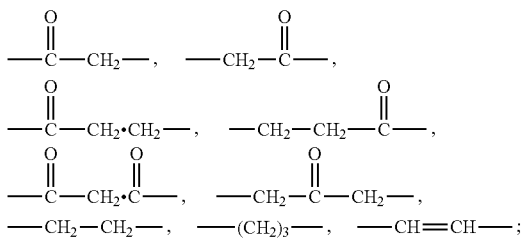

W is at each occurrence independently hydrogen, halogen, hydroxy, alkoxy, carboxy, aldehyde, $NH_2$, $NR^{14}R^{14'}$, nitro, cycloalkyl, heteroaryl, heteroarylalkyl;

where (i) each occurrence of $R^{14}$ and $R^{14'}$ is independently selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or $CF_3$; or (ii) $R^{14}$ and $R^{14'}$, together with the nitrogen atom to which they are bonded, join to form an optionally substituted heterocyclic ring containing from 5 to 8 ring atoms of which from 1 to 3 are heteroatoms;

m is an integer ranging from 1-4;

$R_7$ is hydrogen, halogen, substituted or unsubstituted alkyl, substituted or unsubstituted alkenyl, substituted or unsubstituted alkynyl, substituted or unsubstituted cycloalkyl, carbonyl, alkylcarbonyl, substituted or unsubstituted aryl, alkylaryl, substituted or unsubstituted heterocyclo, substituted or unsubstituted heteroaryl, cyano, nitro, haloalkoxy, alkylamino, alkoxycarbonyl, aryloxy, arylalkyloxy, arylalkyl, cycloalkylalkyloxy, cycloalkyloxy, alkoxyalkyl, alkoxyalkoxy, or aminoalkoxy;

$R_8$ is hydrogen, hydroxy, substituted or unsubstituted alkyl, substituted or unsubstituted alkenyl, substituted or unsubstituted alkynyl, substituted or unsubstituted cycloalkyl, alkylcarboxy, carbonyl, alkylcarbonyl, substituted or unsubstituted aryl, alkylaryl, substituted or unsubstituted heterocyclo, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy;

$R_9$ is hydrogen, hydroxy, substituted or unsubstituted alkyl, substituted or unsubstituted alkenyl, substituted or unsubstituted alkynyl, substituted or unsubstituted cycloalkyl, carboxy, alkylcarboxy, carbonyl, alkylcarbonyl, substituted or unsubstituted aryl, alkylaryl, substituted or unsubstituted heterocyclo, substituted or unsubstituted heteroaryl, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy;

$R_{10}$ is hydrogen, hydroxy, substituted or unsubstituted alkyl, substituted or unsubstituted alkenyl, substituted or unsubstituted alkynyl, substituted or unsubstituted cycloalkyl, alkylcarboxy, carbonyl, alkylcarbonyl, substituted or unsubstituted aryl, alkylaryl, substituted or unsubstituted heterocyclo, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy;

$R_{11}$ is hydrogen, halogen, substituted or unsubstituted alkyl, substituted or unsubstituted alkenyl, substituted or unsubstituted alkynyl, substituted or unsubstituted cycloalkyl, carbonyl, alkylcarbonyl, substituted or unsubstituted aryl, alkylaryl, substituted or unsubstituted heterocyclo, substituted or unsubstituted heteroaryl, cyano, nitro, haloalkoxy, alkylamino, alkoxycarbonyl, aryloxy, arylalkyloxy, arylalkyl, cycloalkylalkyloxy, cycloalkyloxy, alkoxyalkyl, alkoxyalkoxy, or aminoalkoxy;

$R_{12}$, $R_{13}$ and $R_{16}$ are independently hydrogen, halogen, hydroxy, substituted or unsubstituted alkyl, substituted or unsubstituted alkenyl, substituted or unsubstituted alkynyl, substituted or unsubstituted cycloalkyl, carboxy, alkylcarboxy, carbonyl, alkylcarbonyl, substituted or unsubstituted aryl, alkylaryl, substituted or unsubstituted heterocyclo, substituted or unsubstituted heteroaryl, cyano, nitro, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy; with the proviso that when Y is phenyl and $R_1$ and $R_2$ are both H, at least one of $R_7$—$R_{11}$ is not hydrogen.

In one embodiment, the compounds of formula IX, when R is H:

$R_8$ is hydrogen, hydroxy, substituted or unsubstituted alkyl, substituted or unsubstituted alkenyl, substituted or unsubstituted alkynyl, substituted or unsubstituted cycloalkyl, alkylcarboxy, carbonyl, alkylcarbonyl, substituted or unsubstituted aryl, alkylaryl, substituted or unsubstituted heterocyclo, substituted or unsubstituted heteroaryl, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy; and $R_{10}$ is hydrogen, hydroxy, substituted or unsubstituted alkyl, substituted or unsubstituted alkenyl, substituted or unsubstituted alkynyl, substituted or unsubstituted cycloalkyl, alkylcarboxy, carbonyl, alkylcarbonyl, substituted or unsubstituted aryl, alkylaryl, substituted or unsubstituted heterocyclo, substituted or unsubstituted heteroaryl, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy.

In a preferred embodiment, R is H.

In another preferred embodiment, $R_1$ and $R_2$ together form:

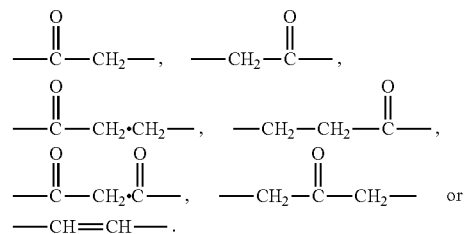

In another preferred embodiment, $R_1$ and $R_2$ together form —$CH_2$—$CH_2$— and only one of $R_7$—$R_{11}$ is other than hydrogen and preferably is a para or meta substituent. In another preferred embodiment, $R_1$ and $R_2$ together form —$CH_2$—$CH_2$— and only two of $R_7$—$R_{11}$ is other than hydrogen and are preferably both meta substituents or meta and para substituents.

In another preferred embodiment, the compounds of formula IX include compounds of the formula:

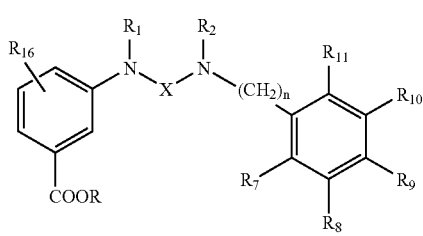

X

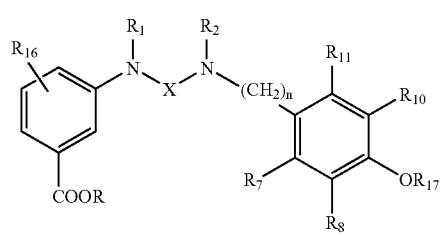

XI

In a preferred embodiment, R is H. In another preferred embodiment, $R_1$ and $R_2$ are hydrogen and X is C(=O). In another preferred embodiment, $R_1$ and $R_2$ taken together are —C(=O)—CH— and X is C(=O). In another preferred embodiment, $R_1$ and $R_2$ together form —$CH_2$—$CH_2$— and only one of $R_7$—$R_{11}$ is other than hydrogen and preferably is a para or meta substituent. In another preferred embodiment, $R_1$ and $R_2$ together form —$CH_2$—$CH_2$— and only two of $R_7$—$R_{11}$ is other than hydrogen and are preferably both meta substituents or meta and para substituents.

In another embodiment, the compounds of formula IX include compounds of the formula:

wherein $R_{17}$ is substituted or unsubstituted alkyl, substituted or unsubstituted cycloalkyl, substituted or unsubstituted aryl, substituted or unsubstituted heterocyclo, substituted or unsubstituted heteroaryl, alkylcarbonyl, alkylamino, alkylthio, alkylcarboxy or arylalkyl. In a preferred embodiment, R is H. In another preferred embodiment, $R_7$ and $R_{11}$ are hydrogen. In another preferred embodiment, $R_7$, $R_8$, $R_{10}$ and $R_{11}$ are hydrogen. In another preferred embodiment, $R_{16}$ is substituted or substituted alkyl, preferably halo substituted alkyl, more preferably tri- or di-fluoro substituted alkyl, most preferably tri- or di-fluoro substituted methyl.

Exemplary compounds of the present invention include those listed below in Table 1:

TABLE 1

| Compound | Compound Name | Melting Point (° C.) or [M + H]$^+$ | Activity[1] |
|---|---|---|---|
| 1 | 3-[3-(4-isopropyl-phenyl)-2,5-dioxo-imidazolidin-1-yl]-benzoic acid | 224-226° C. | *** |
| 2 | 3-(3-biphenyl-4-yl)-2,5-dioxo-imidazolidin-1-yl)-benzoic acid | >300° C. | *** |
| 3 | 3-[2,5-dioxo-3-(4-phenoxy-phenyl)-imidazolidin-1-yl]-benzoic acid | 254-257° C. | ** |

TABLE 1-continued

| Compound | Compound Name | Melting Point (° C.) or [M + H]+ | Activity[1] |
|---|---|---|---|
| 4 | 3-[3-carboxymethyl-3-(4-isopropyl-phenyl)-ureido]-benzoic acid disodium salt | >350° C. | *** |
| 5 | 3-[3-(2-chloro-benzyl)-2,5-dioxo-imidazolidin-1-yl]-benzoic acid | 170-171° C. | *** |
| 6 | 3-(3-cyclohexylmethyl-2,5-dioxo-imidazolidin-1-yl)-benzoic acid | [M + H]+ = 317.4 | * |
| 7 | 3-[6-(4-isopropyl-phenyl)-1,1-dioxo-1l6-[1,2,6]-thiadiazinan-2-yl]-benzoic acid | 200-202° C. | * |
| 8 | 3-[3-(4-isopropyl-phenyl)-ureido]-benzoic acid | 295° C. | *** |
| 9 | 3-[3-(4-isopropyl-phenyl)-2,4-dioxo-imidazolidin-1-yl]-benzoic acid | 249-252° C. | ** |

TABLE 1-continued

| Compound | Compound Name | Melting Point (° C.) or [M + H]+ | Activity[1] |
|---|---|---|---|
| 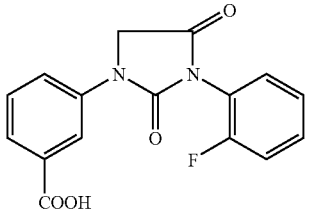 10 | 3-[3-(2-fluoro-phenyl)-2,4-dioxo-imidazolidin-1-yl]-benzoic acid | [M + H]+ = 315.3 | * |
| 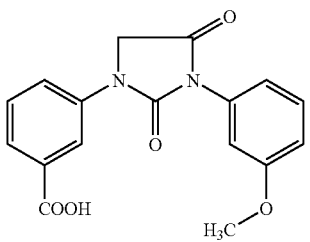 11 | 3-[3-(3-methoxy-phenyl)-2,4-dioxo-imidazolidin-1-yl]-benzoic acid | [M + H]+ = 327.4 | * |
| 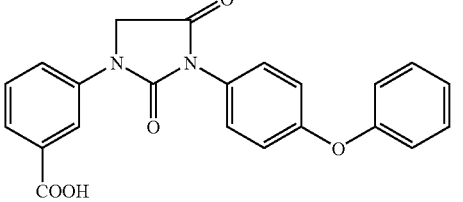 12 | 3-[2,4-dioxo-3-(4-phenoxy-phenyl)-imidazolidin-1-yl]-benzoic acid | [M + H]+ = 389.4 | * |
| 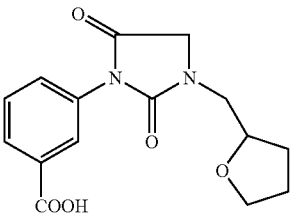 13 | 3-[2,5-dioxo-3-(tetrahydro-furan-2-ylmethyl)-imidazolidin-1-yl]-benzoic acid | [M + H]+ = 305.3 | * |
| 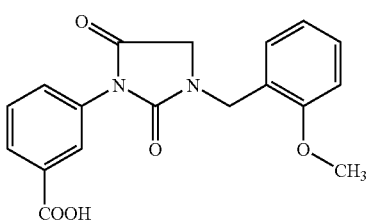 14 | 3-[3-(2-methoxy-benzyl)-2,5-dioxo-imidazolidin-1-yl]-benzoic acid | [M + H]+ = 341.3 | * |
| 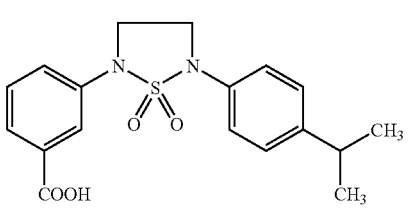 15 | 3-[5-(4-isopropyl-phenyl)-1,1-dioxo-1l6-[1,2,5]-thiadiazolidin-2-yl]-benzoic acid | 253-255° C. | ** |

TABLE 1-continued

| Compound | Compound Name | Melting Point (° C.) or [M + H]+ | Activity[1] |
|---|---|---|---|
| 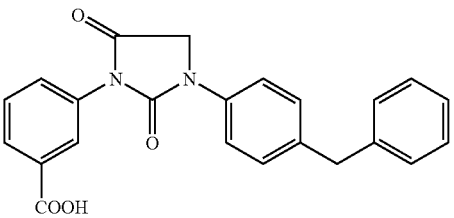 16 | 3-[3-(4-benzyl-phenyl)-2,5-dioxo-imidazolidin-1-yl]-benzoic acid | 232-234° C. | * |
| 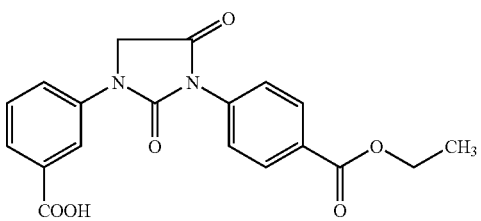 17 | 3-[3-(4-formyl-ethylester-phenyl)-2,4-dioxo-imidazolidin-1-yl]-benzoic acid | [M + H]+ = 369.4 | * |
| 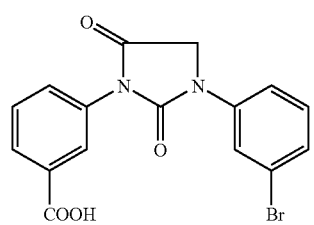 18 | 3-[3-(3-bromo-phenyl)-2,5-dioxo-imidazolidin-1-yl]benzoic acid | 268-270° C. | * |
| 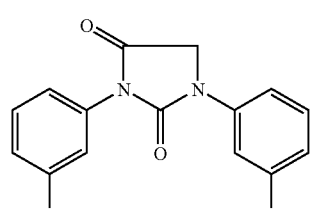 19 | 3-[2,5-dioxo-3-(4-trifluoromethyl-phenyl)-imidazolidin-1-yl]-benzoic acid | 185-187° C. | * |
| 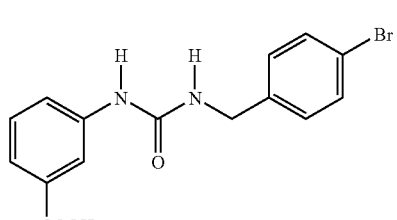 20 | 3-[3-(4-bromo-benzyl)-ureido]-benzoic acid | 250-252° C. | * |
| 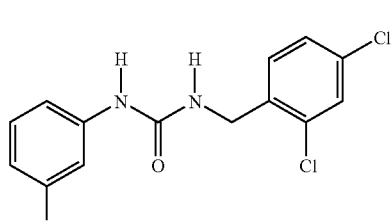 21 | 3-[3-(2,4-dichloro-benzyl)-ureido]-benzoic acid | 250-252° C. | * |

TABLE 1-continued

| Compound | Compound Name | Melting Point (° C.) or [M + H]+ | Activity[1] |
|---|---|---|---|
| 22 | 3-[3-(4-bromo-phenyl)-ureido]-benzoic acid | 290-295° C. | * |
| 23 | 3-[3-(4-iodo-phenyl)-2,5-dioxo-imidazolidin-1-yl]-benzoic acid | 250-253° C. | *** |
| 24 | 3-[3-(2,3-dichloro-phenyl)-2,4-dioxo-imidazolidin-1yl]-benzoic acid | [M + H]+ = 366.2 | * |
| 25 | 3-[3-(4-methoxycarbonylphenyl)-2,5-dioxomidazolidin-1-yl]-benzoic acid | 274-276° C. | * |
| 26 | 3-(2,5-Dioxo-3-p-tolylimidazolidin-1-yl)-benzoic acid | 249-251° C. | * |
| 27 | 3-[3-(4-Ethoxy-phenyl)-2,5-dioxo-imidazolidin-1-yl]-benzoic acid | 253-256° C. | * |

TABLE 1-continued

| Compound | Compound Name | Melting Point (° C.) or [M + H]+ | Activity[1] |
|---|---|---|---|
| 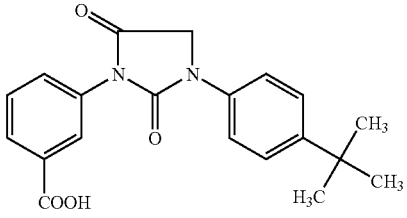 28 | 3-[3-(4-tert-Butylphenyl)-2,5-dioxoimidazolidin-1-yl]-benzoic acid | 256-258° C. | ** |
| 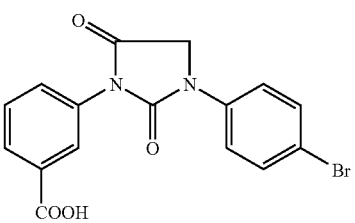 29 | 3-[3-(4-Bromo-phenyl)-2,5-dioxo-imidazolidin-1-yl]-benzoic acid | 293-296° C. | * |
| 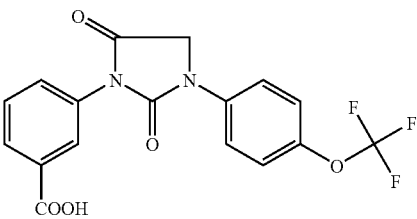 30 | 3-[2,5-Dioxo-3-(4-trifluoromethoxy-phenyl)-imidazolidin-1-yl]-benzoic acid | 254-256° C. | * |
| 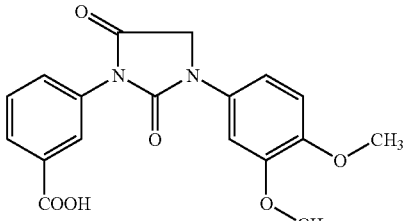 31 | 3-[3-(2,3-Dimethoxybenzyl)-2,5-dioxoimidazolidin-1-yl]-benzoic acid | 151-152° C. | * |
| 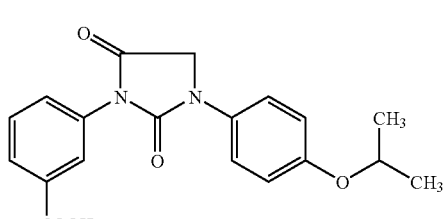 32 | 3-[3-(4-Isopropoxyphenyl)-2,5-dioxoimidazolidin-1-yl]-benzoic acid | 337-339° C. | * |
| 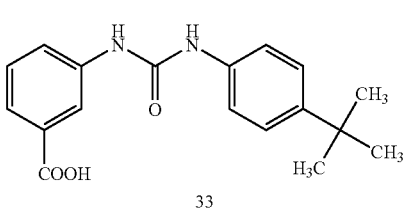 33 | 3-[3-(4-tert-Butylphenyl)-ureido]-benzoic acid | 147-149° C. | ** |

TABLE 1-continued

| Compound | Compound Name | Melting Point (° C.) or [M + H]+ | Activity[1] |
|---|---|---|---|
| 34 | 3-[3-(4-Isopropyl-phenyl)-2-oxo-imidazolidin-1-yl]-benzoic acid | 238-240° C. | ***** |
| 35 | 3-[3-(4-Isopropyl-phenyl)-2-oxo-2,3-dihydro-imidazol-1-yl]-benzoic acid | 283-285° C. (decomp.) | *** |
| 36 | 3-[3-(3-Isopropyl-phenyl)-2-oxo-imidazolidin-1-yl]-benzoic acid | 189-190° C. | **** |
| 37 | 3-[3-(4-Isopropyl-phenyl)-2-thioxo-2,3-dihydro-imidazol-1-yl]-benzoic acid | 226-227° C. | * |
| 38 | 3-[2-Oxo-3-(4-trifluoromethoxy-phenyl)-imidazolidin-1-yl]-benzoic acid | 221-222° C. | ***** |
| 39 | 3-[3-(4-Difluoromethoxy-phenyl)-2-oxo-imidizolidin-1-yl]-benzoic acid | 223-224° C. | ***** |
| 40 | 3-[3-(4-Isopropoxy-phenyl)-2-oxo-imidazolidin-1-yl]-benzoic acid | 253-255° C. | ***** |

TABLE 1-continued

| Compound | Compound Name | Melting Point (° C.) or [M + H]+ | Activity[1] |
|---|---|---|---|
| 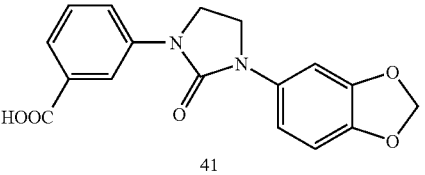 41 | 3-(3-Benzo[1,3]dioxol-5-yl-2-oxo-imidazolidin-1-yl)-benzoic acid | 282-283° C. | ***** |
| 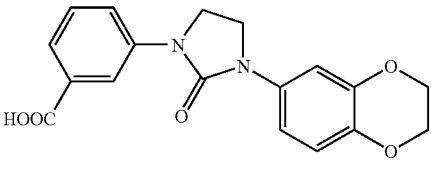 42 | 3-[3-(2,3-Dihydro-benzo[1,4]dioxin-6-yl)-2-oxo-imidazolidin-1-yl]-benzoic acid | 271-272° C. | ***** |
| 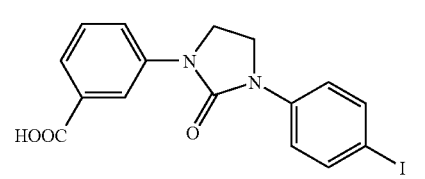 43 | 3-[3-(4-Iodo-phenyl)-2-oxo-imidazolidin-1-yl]-benzoic acid | 270-271° C. | ***** |
| 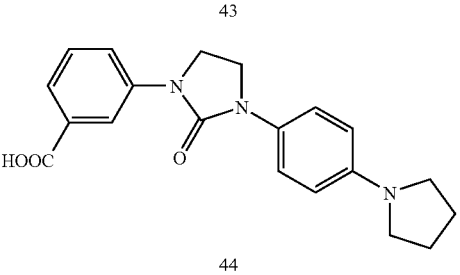 44 | 3-[2-Oxo-3-(4-pyrrolidin-1-yl-phenyl)-imidazolidin-1-yl]-benzoic acid | 276-278° C. (decomp.) | **** |
| 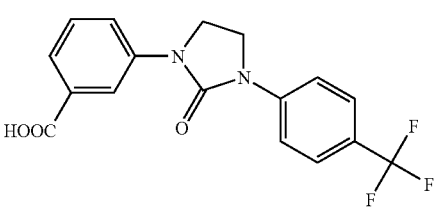 45 | 3-[2-Oxo-3-(4-trifluoromethyl-phenyl)-imidazolidin-1-yl]-benzoic acid | 254-255° C. | ***** |
| 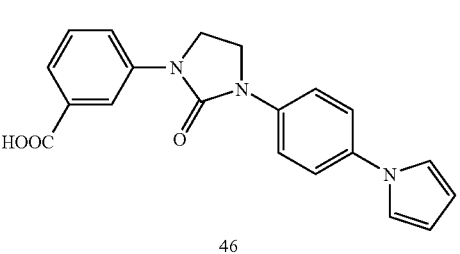 46 | 3-[2-Oxo-3-(4-pyrrol-1-yl-phenyl)-imidazolidin-1-yl]-benzoic acid | 273-274° C. (decomp.) | ***** |
| 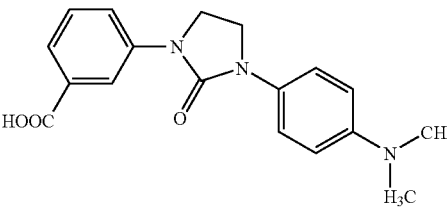 47 | 3-[3-(4-Dimethylamino-phenyl)-2-oxo-imidazolidin-1-yl]-benzoic acid | 279-280° C. | ***** |

TABLE 1-continued

| Compound | Compound Name | Melting Point (° C.) or [M + H]+ | Activity[1] |
|---|---|---|---|
| 48 | 3-(2-Oxo-3-p-tolyl-imidazolidin-1-yl)-benzoic acid | 263-265° C. | ***** |
| 49 | 3-[3-(4-Methoxy-phenyl)-2-oxo-imidazolidin-1-yl]-benzoic acid | 244-245° C. | **** |
| 50 | 3-[3-(2,2-Difluoro-benzo[1,3]dioxol-5-yl)-2-oxo-imidazolidin-1-yl]-benzoic acid | 259-260° C. (decomp.) | **** |
| 51 | 3-[2-Oxo-3-(2,2,3,3-tetrafluoro-2,3-dihydro-benzo[1,4]dioxin-6-yl)-imidazolidin-1-yl]-benzoic acid | 238-239° C. | ***** |
| 52 | 4-Methoxy-3-[2-oxo-3-(4-trifluoromethyl-phenyl)-imidazolidin-1-yl]-benzoic acid | 271-274° C. | * |
| 53 | 2-Fluoro-5-[2-oxo-3-(4-trifluoromethyl-phenyl)-imidazolidin-1-yl]-benzoic acid | 241-242° C. | **** |
| 54 | 2-Chloro-5-[2-oxo-3-(4-trifluoromethyl-phenyl)-imidazolidin-1-yl]-benzoic acid | 214-215° C. | **** |

TABLE 1-continued

| Compound | Compound Name | Melting Point (° C.) or [M + H]+ | Activity[1] |
|---|---|---|---|
| 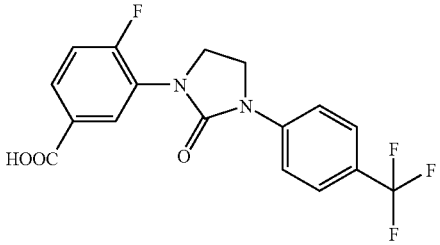 55 | 4-Fluoro-3-[2-oxo-3-(4-trifluoromethyl-phenyl)-imidazolidin-1-yl]-benzoic acid | 256-257° C. | * |
| 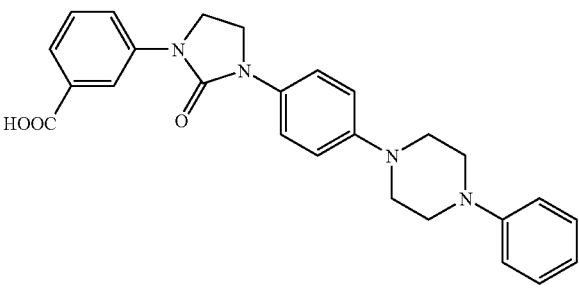 56 | 3-{2-Oxo-3-[4-(4-phenyl-piperazin-1-yl)-phenyl]-imidazolidin-1-yl}-benzoic acid | 293° C. (decomp.) | * |
| 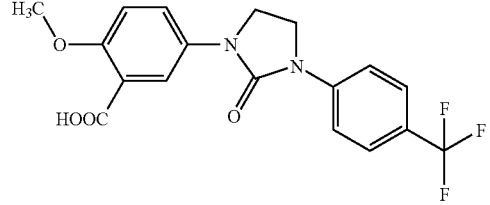 57 | 2-Methoxy-5-[2-oxo-3-(4-trifluoromethyl-phenyl)-imidazolidin-1-yl]-benzoic acid | 209-210° C. | * |
| 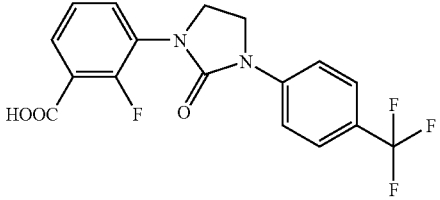 58 | 2-Fluoro-3-[2-oxo-3-(4-rifluoromethyl-phenyl)-imidazolidin-1-yl]-benzoic acid | 246-247° C. | ** |
| 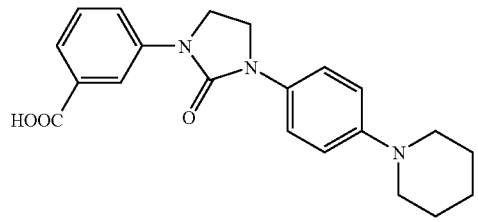 59 | 3-[2-Oxo-3-(4-piperidin-1-yl-phenyl)-imidazolidin-1-yl]-benzoic acid | 284-286° C. | **** |
| 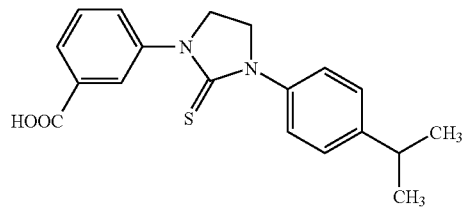 60 | 3-[3-(4-Isopropyl-phenyl)-2-thioxo-imidazolidin-1-yl]-benzoic acid | 248-249° C. | **** |

TABLE 1-continued

| Compound | Compound Name | Melting Point (° C.) or [M + H]+ | Activity[1] |
|---|---|---|---|
| 60 | 3-(2-Oxo-3-{4-[2-oxo-2-(4-phenyl-piperazin-1-yl)-ethoxy]-phenyl}-imidazolidin-1-yl)-benzoic acid | 228-230° C. | * |
| 61 | 3-[5,5-Dimethyl-2-oxo-3-(4-trifluoromethoxy-phenyl)-imidazolidin-1-yl]-benzoic acid | 178-181° C. | * |
| 62 | 3-[3-(4-Fluoro-3-trifluoromethyl-phenyl)-2-oxo-imidazolidin-1-yl]-benzoic acid | 263-265° C. | **** |
| 63 | 3-[2-Oxo-3-(3-trifluoromethoxy-phenyl)-imidazolidin-1-yl]-benzoic acid | 210-213° C. | **** |
| 64 | 3-[3-(3,4-Difluoro-phenyl)-2-oxo-imidazolidin-1-yl]-benzoic acid | 258-262° C. | ***** |
| 65 | 3-[3-(3,5-Difluoro-phenyl)-2-oxo-imidazolidin-1-yl]-benzoic acid | 283-287° C. | ***** |
| 66 | 3-[3-(2,5-Difluoro-phenyl)-2-oxo-imidazolidin-1-yl]-benzoic acid | 236-239° C. | ** |
| 67 | | | |

TABLE 1-continued

| Compound | Compound Name | Melting Point (° C.) or [M + H]+ | Activity[1] |
|---|---|---|---|
| 68 | 3-[3-(2-Fluoro-phenyl)-2-oxo-imidazolidin-1-yl]-benzoic acid | 228-230° C. | *** |
| 69 | 3-[3-(3-Fluoro-phenyl)-2-oxo-imidazolidin-1-yl]-benzoic acid | 260-263° C. | ***** |
| 70 | 3-[3-(4-Fluoro-phenyl)-2-oxo-imidazolidin-1-yl]-benzoic acid | 275-277° C. | ***** |
| 71 | 3-[3-(3-Fluoro-4-methyl-phenyl)-2-oxo-imidazolidin-1-yl]-benzoic acid | 267-269° C. | ***** |
| 72 | 3-[2-Oxo-3-(5-trifluoromethyl-pyridin-2-yl)-imidazolidin-1-yl]-benzoic acid | 291-293° C. | **** |
| 73 | 3-(2-Oxo-3-thiophen-2-yl-imidazolidin-1-yl)-benzoic acid | 273-275° C. | **** |
| 74 | 3-(2-Oxo-3-thiophen-3-yl-imidazolidin-1-yl)-benzoic acid | 251-253° C. | **** |
| 75 | 3-[3-(2,4-Difluoro-phenyl)-2-oxo-imidazolidin-1-yl]-benzoic acid | 262-264° C. | * |

TABLE 1-continued

| Compound | Compound Name | Melting Point (° C.) or [M + H]+ | Activity[1] |
|---|---|---|---|
| 76 | 3-{3-[4-(4-Methyl-piperazin-1-yl)-phenyl]-2-oxo-imidazolidin-1-yl}-benzoic acid | 301° C. (decomp.) | * |
| 77 | 3-{3-[4-(2-Morpholin-4-yl-2-oxo-ethoxy)-phenyl]-2-oxo-imidazolidin-1-yl}-benzoic acid | 278-280° C. | * |
| 78 | 3-(3-{4-[2-(4-Methyl-piperazin-1-yl)-2-oxo-ethoxy]-phenyl}-2-oxo-imidazolidin-1-yl)-benzoic acid | 271-274° C. | * |
| 79 | 3-[3-(6-Fluoro-pyridin-3-yl)-2-oxo-imidazolidin-1-yl]-benzoic acid | 265-266° C. (decomp.) | * |
| 80 | 4-Methyl-3-[2-oxo-3-(4-trifluoromethyl-phenyl)-imidazolidin-1-yl]-benzoic acid | 257-258° C. | * |
| 81 | 3-[3-(4-[1,4']Bipiperidinyl-1'-yl-phenyl)-2-oxo-imidazolidin-1-yl]-benzoic acid | 284-286° C. (decomp.) | * |

TABLE 1-continued

| Compound | Compound Name | Melting Point (° C.) or [M + H]+ | Activity[1] |
|---|---|---|---|
| 82 | 3-[4,4-Dimethyl-2-oxo-3-(4-trifluoromethoxy-phenyl)-imidazolidin-1-yl]-benzoic acid | 194-197° C. | * |

Melting points were obtained on an Electrothermal Melt-Temp™ apparatus and are uncorrected. Alternatively, for those compounds without melting point data, the results from mass spec analysis using a Micro Mass (Beverly, Mass.) ESI-MS (electrospray ionization-mass spectrometer) are given as [M+H]+.

Activity measurements in Table I were performed in a cell-based luciferase reporter assay (as described in Section 4.2) comprising a luciferase reporter construct containing a UGA premature termination codon that was stably transfected in 293T Human Embryonic Kidney cells. A small molecule (3-[3-(4-Isopropyl-phenyl)-2,5-dioxoimidazolidin-1-yl]-benzoic acid) known to allow readthrough of premature termination codons, was used as an internal standard. Activity measurements are based on the qualitative relation between the minimum concentration of compound required to produce a given protein in a cell (potency) and the maximum amount of protein produced by the cell (efficacy). Potency and efficacy activities are ranked as either extremely high, very high or significant. The combination of these activities is used to determine the activity ranking. Compounds which were found to have both extremely high potency and extremely high efficacy of protein synthesis are classified as "***". Compounds which were found to have extremely high potency of protein synthesis and very high efficacy were classified as "". Compounds which were found to have very high potency of protein synthesis and extremely high efficacy were classified as "". Compounds which were found to have both very high potency and very high efficacy of protein synthesis are classified as "*". Compounds which were found to have very high potency of protein synthesis and significant efficacy were classified as "". Compounds which were found to have significant potency of protein synthesis and very high efficacy were classified as "". Similarly, compounds which were found to have significant potency and efficacy of protein synthesis were classified as "*" (see table below).

| Potency | Efficacy | Ranking |
|---|---|---|
| Extremely high | Extremely high | ***** |
| Extremely high | Very high | **** |
| Very high | Extremely high | **** |
| Very high | Very high | *** |
| Very high | Significant | ** |
| Significant | Very high | ** |
| Significant | Significant | * |

The present invention encompasses the in vitro or in vivo use of a compound of the invention, and the incorporation of a compound of the invention into pharmaceutical compositions and single unit dosage forms useful in the treatment and prevention of a variety of diseases and disorders. Specific diseases and disorders include those ameliorated by the suppression of a nonsense mutation in messenger RNA.

Pharmaceutical compositions including dosage forms of the invention, which comprise a compound of the invention or a pharmaceutically acceptable polymorph, prodrug, salt, clathrate, solvate or hydrate thereof, can be used in the methods of the invention.

Without being limited by theory, it is believed that a compound of the invention can modulate premature translation termination and/or nonsense-mediated mRNA decay. Consequently, a first embodiment of the invention relates to a method of modulating premature translation termination and/or nonsense-mediated mRNA decay comprising contacting a cell exhibiting a nonsense mutation with an effective amount of a compound of the invention, or a pharmaceutically acceptable prodrug, metabolite, polymorph, salt, solvate, hydrate, or clathrate thereof. In a particular embodiment, the invention relates to a method of inducing nonsense suppression comprising contacting a cell exhibiting a nonsense mutation with an effective amount of a compound of the invention, or a pharmaceutically acceptable prodrug, metabolite, polymorph, salt, solvate, hydrate, or clathrate thereof.

4.2 Biological Assays and Animal Studies

The test compounds identified in the nonsense suppression assay (for convenience referred to herein as a "lead" compound) can be tested for biological activity using host cells containing or engineered to contain the target RNA element coupled to a functional readout system. For example, the lead compound can be tested in a host cell engineered to contain the RNA with the premature translation termination codon controlling the expression of a reporter gene. In this example, the lead compounds are assayed in the presence or absence of the RNA with the premature translation termination codon. Compounds that modulate premature translation termination and/or nonsense-mediated mRNA decay in vivo will result in increased expression of the full-length gene, i.e., past the premature termination codon. Alternatively, a phenotypic or physiological readout can be used to assess activity of the target RNA with the premature translation termination codon in the presence and absence of the lead compound. Both the in vitro and in vivo nonsense suppression assays used herein and as described in International Patent Publication WO 01/44516, which is incorporated by reference in its entirety, can be used to identify lead compounds can also be used to determine an $EC_{50}$ for the lead compounds.

Animal model systems can also be used to demonstrate the safety and efficacy of compounds of formula I. The compounds of formula I can be tested for biological activity using animal models for a disease, condition, or syndrome of interest. These include animals engineered to contain the target RNA element coupled to a functional readout system, such as a transgenic mouse.

Examples of animal models for cystic fibrosis include, but are not limited to, cftr(−/−) mice (see, e.g., Freedman et al., 2001, Gastroenterology 121(4):950-7), cftr(tm1HGU/tm1HGU) mice (see, e.g., Bernhard et al., 2001, Exp Lung Res 27(4):349-66), CFTR-deficient mice with defective cAMP-mediated Cl(−) conductance (see, e.g., Stotland et al., 2000, Pediatr Pulmonol 30(5):413-24), and C57BL/6-Cftr (m1UNC)/Cftr(m1UNC) knockout mice (see, e.g., Stotland et al., 2000, Pediatr Pulmonol 30(5):413-24).

Examples of animal models for muscular dystrophy include, but are not limited to, mouse, hamster, cat, dog, and *C. elegans*. Examples of mouse models for muscular dystrophy include, but are not limited to, the dy−/− mouse (see, e.g., Connolly et al., 2002, J Neuroimmunol 127(1-2):80-7), a muscular dystrophy with myositis (mdm) mouse mutation (see, e.g., Garvey et al., 2002, Genomics 79(2):146-9), the mdx mouse (see, e.g., Nakamura et al., 2001, Neuromuscul Disord 11(3):251-9), the utrophin-dystrophin knockout (dko) mouse (see, e.g., Nakamura et al., 2001, Neuromuscul Disord 11(3):251-9), the dy/dy mouse (see, e.g., Dubowitz et al., 2000, Neuromuscul Disord 10(4-5):292-8), the mdx(Cv3) mouse model (see, e.g., Pillers et al., 1999, Laryngoscope 109(8):1310-2), and the myotonic ADR-MDX mutant mice (see, e.g., Kramer et al., 1998, Neuromuscul Disord 8(8):542-50). Examples of hamster models for muscular dystrophy include, but are not limited to, sarcoglycan-deficient hamsters (see, e.g., Nakamura et al., 2001, Am J Physiol Cell Physiol 281(2):C690-9) and the BIO 14.6 dystrophic hamster (see, e.g., Schlenker & Burbach, 1991, J Appl Physiol 71(5):1655-62). An example of a feline model for muscular dystrophy includes, but is not limited to, the hypertrophic feline muscular dystrophy model (see, e.g., Gaschen & Burgunder, 2001, Acta Neuropathol (Berl) 101(6):591-600). Canine models for muscular dystrophy include, but are not limited to, golden retriever muscular dystrophy (see, e.g., Fletcher et al., 2001, Neuromuscul Disord 11(3):239-43) and canine X-linked muscular dystrophy (see, e.g., Valentine et al., 1992, Am J Med Genet 42(3):352-6). Examples of *C. elegans* models for muscular dystrophy are described in Chamberlain & Benian, 2000, Curr Biol 10(21):R795-7 and Culette & Sattelle, 2000, Hum Mol Genet 9(6):869-77.

Examples of animal models for familial hypercholesterolemia include, but are not limited to, mice lacking functional LDL receptor genes (see, e.g., Aji et al., 1997, Circulation 95(2):430-7), Yoshida rats (see, e.g., Fantappie et al., 1992, Life Sci 50(24):1913-24), the JCR:LA-cp rat (see, e.g., Richardson et al., 1998, Atherosclerosis 138(1):135-46), swine (see, e.g., Hasler-Rapacz et al., 1998, Am J Med Genet 76(5): 379-86), and the Watanabe heritable hyperlipidaemic rabbit (see, e.g., Tsutsumi et al., 2000, Arzneimittelforschung 50(2): 118-21; Harsch et al., 1998, Br J Pharmacol 124(2):227-82; and Tanaka et al., 1995, Atherosclerosis 114(1):73-82).

An example of an animal model for human cancer in general includes, but is not limited to, spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Ape mouse models (see, e.g., Fodde & Smits, 2001, Trends Mol Med 7(8):369-73 and Kuraguchi et al., 2000, Oncogene 19(50):5755-63). An example of an animal model for neurofibromatosis includes, but is not limited to, mutant NF1 mice (see, e.g., Cichowski et al., 1996, Semin Cancer Biol 7(5):291-8). Examples of animal models for retinoblastoma include, but are not limited to, transgenic mice that expression the simian virus 40 T antigen in the retina (see, e.g., Howes et al., 1994, Invest Ophthalmol Vis Sci 35(2):342-51 and Windle et al, 1990, Nature 343 (6259):665-9) and inbred rats (see, e.g., Nishida et al., 1981, Curr Eye Res 1(1):53-5 and Kobayashi et al., 1982, Acta Neuropathol (Berl) 57(2-3):203-8). Examples of animal models for Wilm's tumor include, but are not limited to, a WT1 knockout mice (see, e.g., Scharnhorst et al., 1997, Cell Growth Differ 8(2):133-43), a rat subline with a high incidence of neuphroblastoma (see, e.g., Mesfin & Breech, 1996, Lab Anim Sci 46(3):321-6), and a Wistar/Furth rat with Wilms' tumor (see, e.g., Murphy et al., 1987, Anticancer Res 7(4B):717-9).

Examples of animal models for retinitis pigmentosa include, but are not limited to, the Royal College of Surgeons ("RCS") rat (see, e.g., Vollrath et al., 2001, Proc Natl Acad Sci USA 98(22);12584-9 and Hanitzsch et al., 1998, Acta Anat (Basel) 162(2-3):119-26), a rhodopsin knockout mouse (see, e.g., Jaissle et al., 2001, Invest Ophthalmol Vis Sci 42(2):506-13), and Wag/Rij rats (see, e.g., Lai et al., 1980, Am J Pathol 98(1):281-4).

Examples of animal models for cirrhosis include, but are not limited to, $CCl_4$-exposed rats (see, e.g., Kloehn et al., 2001, Horm Metab Res 33(7):394-401) and rodent models instigated by bacterial cell components or colitis (see, e.g., Vierling, 2001, Best Pract Res Clin Gastroenterol 15(4):591-610).

Examples of animal models for hemophilia include, but are not limited to, rodent models for hemophilia A (see, e.g., Reipert et al., 2000, Thromb Haemost 84(5):826-32; Jarvis et al., 1996, Thromb Haemost 75(2):318-25; and Bi et al., 1995, Nat Genet 10(1):119-21), canine models for hemophilia A (see, e.g., Gallo-Penn et al., 1999, Hum Gene Ther 10(11): 1791-802 and Connelly et al, 1998, Blood 91(9);3273-81), murine models for hemophilia B (see, e.g., Snyder et al., 1999, Nat Med 5(1):64-70; Wang et al., 1997, Proc Natl Acad Sci USA 94(21):11563-6; and Fang et al., 1996, Gene Ther 3(3):217-22), canine models for hemophilia B (see, e.g., Mount et al., 2002, Blood 99(8):2670-6; Snyder et al., 1999, Nat Med 5(1):64-70; Fang et al., 1996, Gene Ther 3(3):217-22); and Kay et al., 1994, Proc Natl Acad Sci USA 91(6):2353-7), and a rhesus macaque model for hemophilia B (see, e.g., Lozier et al., 1999, Blood 93(6):1875-81).

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, Lab Invest 59(4):443-52), and porcine models for von Willebrand disease (see, e.g., Nichols et al., 1995, Proc Natl Acad Sci USA 92(7):2455-9; Johnson & Bowie, 1992, J Lab Clin Med 120(4):553-8; and Brinkhous et al., 1991, Mayo Clin Proc 66(7):733-42).

Examples of animal models for b-thalassemia include, but are not limited to, murine models with mutations in globin genes (see, e.g., Lewis et al., 1998, Blood 91(6):2152-6; Raja et al., 1994, Br J Haematol 86(1):156-62; Popp et al., 1985, 445:432-44; and Skow et al., 1983, Cell 34(3):1043-52).

Examples of animal models for kidney stones include, but are not limited to, genetic hypercalciuric rats (see, e.g., Bushinsky et al., 1999, Kidney Int 55(1):234-43 and Bushinsky et al., 1995, Kidney Int 48(6):1705-13), chemically treated rats (see, e.g., Grases et al., 1998, Scand J Urol Nephrol 32(4):261-5; Burgess et al., 1995, Urol Res 23(4):239-42; Kumar et al., 1991, J Urol 146(5):1384-9; Okada et al., 1985, Hinyokika Kiyo 31(4):565-77; and Bluestone et al., 1975, Lab Invest 33(3):273-9), hyperoxaluric rats (see, e.g., Jones et al., 1991, J Urol 145(4):868-74), pigs with unilateral retrograde flexible nephroscopy (see, e.g., Seifmah et al., 2001, 57(4):832-6), and rabbits with an obstructed upper urinary tract (see, e.g., Itatani et al., 1979, Invest Urol 17(3):234-40).

Examples of animal models for ataxia-telangiectasia include, but are not limited to, murine models of ataxia-telangiectasia (see, e.g., Barlow et al., 1999, Proc Natl Acad Sci USA 96(17):9915-9 and Inoue et al., 1986, Cancer Res 46(8):3979-82).

Examples of animal models for lysosomal storage diseases include, but are not limited to, mouse models for muco-polysaccharidosis type VII (see, e.g., Brooks et al., 2002, Proc Natl Acad Sci USA. 99(9):6216-21; Monroy et al., 2002, Bone 30(2):352-9; Vogler et al., 2001, Pediatr Dev Pathol. 4(5):421-33; Vogler et al., 2001, Pediatr Res. 49(3):342-8; and Wolfe et al., 2000, Mol Ther. 2(6):552-6), a mouse model for metachromatic leukodystrophy (see, e.g., Matzner et al., 2002, Gene Ther. 9(1):53-63), a mouse model of Sandhoff disease (see, e.g., Sango et al., 2002, Neuropathol Appl Neurobiol. 28(1):23-34), mouse models for mucopolysaccharidosis type III A (see, e.g., Bhattacharyya et al., 2001, Glycobiology 11(1):99-10 and Bhaumik et al., 1999, Glycobiology 9(12):1389-96.), arylsulfatase A (ASA)-deficient mice (see, e.g., D'Hooge et al., 1999, Brain Res. 847(2):352-6 and D'Hooge et al, 1999, Neurosci Lett. 273(2):93-6); mice with an aspartylglucosaminuria mutation (see, e.g., Jalanko et al., 1998, Hum Mol Genet. 7(2):265-72); feline models of mucopolysaccharidosis type VI (see, e.g., Crawley et al., 1998, J Clin Invest. 101(1):109-19 and Norrdin et al., 1995, Bone 17(5):485-9); a feline model of Niemann-Pick disease type C (see, e.g., March et al., 1997, Acta Neuropathol (Berl). 94(2):164-72); acid sphingomyelinase-deficient mice (see, e.g., Otterbach & Stoffel, 1995, Cell 81(7):1053-6), and bovine mannosidosis (see, e.g., Jolly et al., 1975, Birth Defects Orig Arctic Ser. 11(6):273-8).

Examples of animal models for tuberous sclerosis ("TSC") include, but are not limited to, a mouse model of TSC1 (see, e.g., Kwiatkowski et al., 2002, Hum Mol Genet. 11(5):525-34), a Tsc1 (TSC1 homologue) knockout mouse (see, e.g., Kobayashi et al., 2001, Proc Natl Acad Sci USA. Jul. 17, 2001; 98(15):8762-7), a TSC2 gene mutant(Eker) rat model (see, e.g., Hino 2000, Nippon Rinsho 58(6):1255-61; Mizuguchi et al., 2000, J Neuropathol Exp Neurol. 59(3):188-9; and Hino et al., 1999, Prog Exp Tumor Res. 35:95-108); and Tsc2(±) mice (see, e.g., Onda et al., 1999, J Clin Invest. 104(6):687-95).

4.3 Synthesis and Preparation

The compounds of the invention can be obtained via standard, well-known synthetic methodology, see e.g. March, J. *Advanced Organic Chemistry; Reactions Mechanisms, and Structure*, 4$^{th}$ ed., 1992. A convenient method is illustrated in Scheme A. Starting materials useful for preparing the compounds of the invention and intermediates therefore, are commercially available or can be prepared from commercially available materials using known synthetic methods and reagents.

Compounds of formula I can be synthesized using the synthesis depicted in Scheme A below:

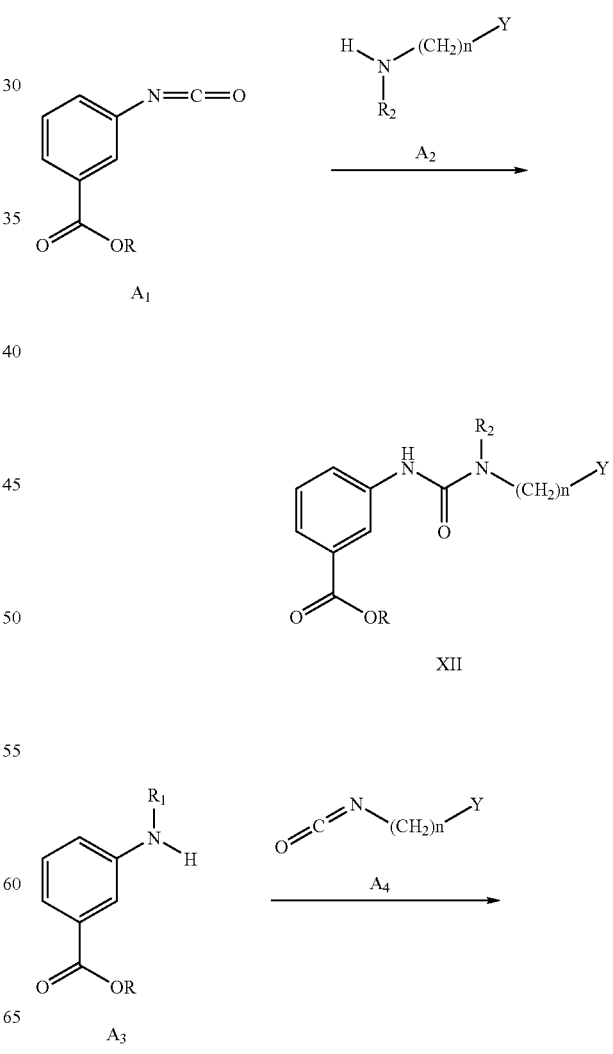

-continued

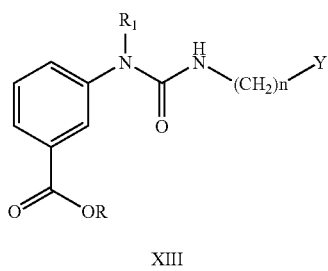

XIII

Isocyanates corresponding to either half of the urea product may be synthesized and isolated according to methods well established in the art of organic chemistry. Such methods may be found in Sandier and Karo, *Organic Functional Group Preparations*, vol. I, pp. 364-369, 1983, Academic Press, Inc., San Diego, Calif., and include, but are not limited to, the following methods. An amine compound may be treated with phosgene (or a phosgene equivalent) in non-reactive solvents and with the presence of basic reagents as catalysts to afford the isocyanates. Alkyl halides may be treated with a cyanate salt (e.g., silver cyanate). Acyl azide compounds are known to rearrange thermally (the Curtius reaction) to generate isocyanates. Another useful method involves in-situ ureidification, which involves the treatment of an amine compound with a reagent capable of transferring an aminocarbonyl group, usually under thermal conditions in inert solvents including, but not limited to, mono- or dinitrophenylcarbamates and p-toluenesulfonylureas.

Compounds of formula I represented by structure XIV can be prepared by the methodology depicted in Scheme B, below. An amine compound B1 is alkylated with a reagent B2, wherein the group L represents some leaving group (e.g., chloro, bromo, iodo, trifluoromethanesulfonyl). The reaction is usually performed in the presence of a base reagent, such as sodium acetate, potassium carbonate or triethylamine, in a solvent such as methanol, tert-butanol or dimethylformamide, and at temperatures ranging from ambient to the reflux temperature of the chosen solvent. The aminoester compound B3 can then be treated with an isocyanate reagent B4 to afford the urea compound B5. Isocyanates are often available commercially, but can be prepared by methods familiar to one skilled in the art of organic chemistry, including, but not limited to, treatment of the corresponding aniline compound with phosgene (or a phosgene substitute) or Curtius rearrangement of a suitably substituted benzoyl azide compound. The coupling of compounds B3 and B4 can be performed in a suitably unreactive solvent, such as toluene, xylene, or dichloromethane, or even a mixture of such solvents (to effect maximum solubilization). The presence of a tertiary amine reagent (such as diisopropylethylamine or triethylamine) will often favorably catalyze the coupling reaction. Temperatures of the reaction range from ambient to reflux of the solvent. Ring-closure of urea compound B5 can be effected by the treatment of a base reagent such as sodium methoxide, potassium tert-butoxide or pyridine, typically in alcoholic solvents. Ring-closure can also be accomplished under acidic conditions (e.g., conc. hydrochloric acid). An alternative method involves a one-pot condensation reaction of amine B3 with aniline compound B6 and reagent B7. Here, L' represents a group activated for displacement at higher temperatures (e.g., phenoxy, imidazolyl, triazolyl). This reaction is typically performed in a high-boiling solvent (e.g., cresol, diphenyl ether), and is particularly successful using a suitably substituted aminobenzoic acid (i.e., R is H).

Scheme B

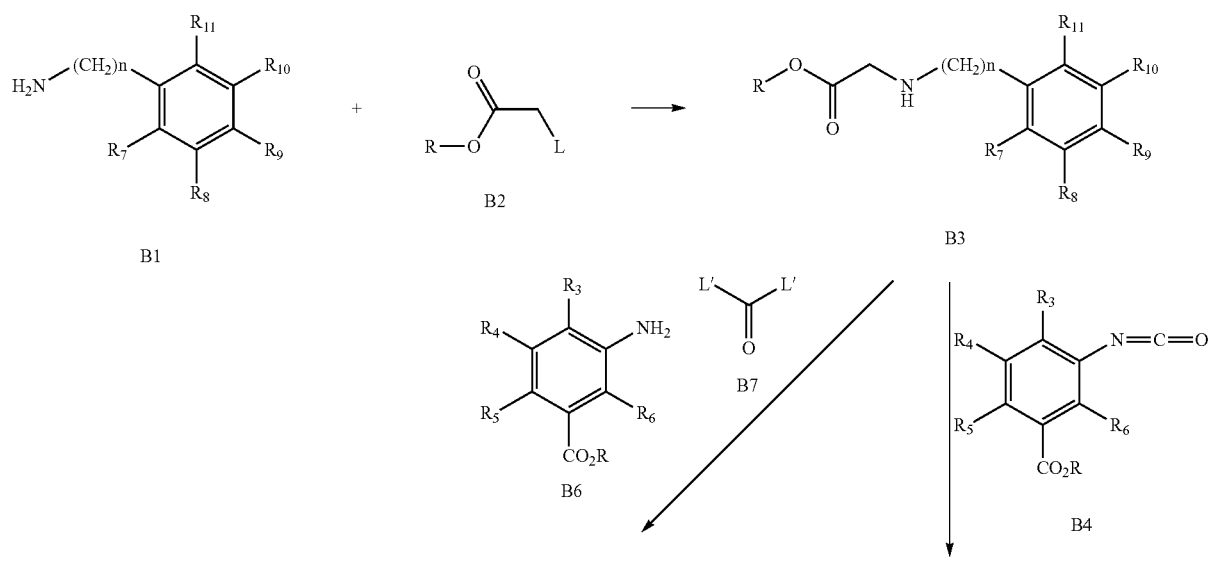

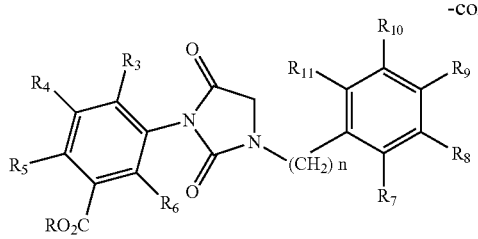
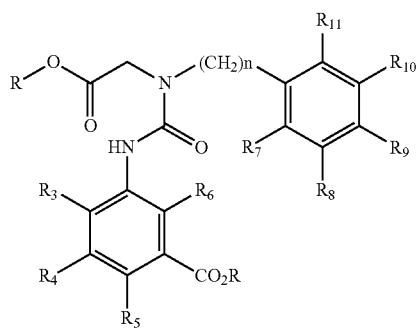

XIV

B5

Compounds of structure XV, can be prepared by one skilled in the art with methodology of Scheme B by using reagents of the reversed substitution pattern of that of Scheme B but the same general types of reactions as illustrated in Scheme C, below.

formation can include alkali reagents (e.g., sodium hydroxide, potassium hydroxide) or carbonate salts in solvents such as methanol, ethanol or tetrahydrofuran. Slight warming may be needed to accelerate the reaction. Alternatively, the intermediate ester compound Scheme C

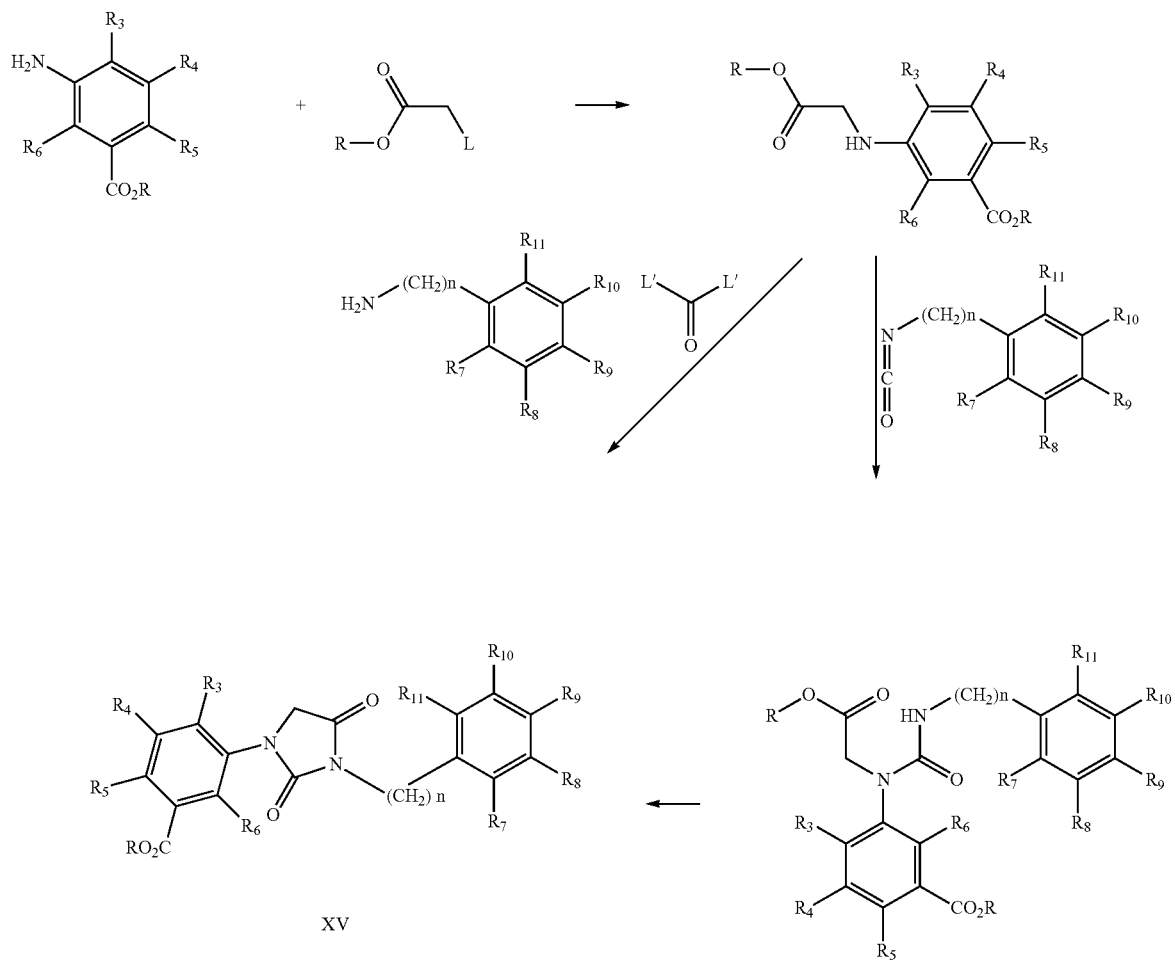

XV

Compounds of formula I under the invention embodiment represented by structures XVI can be prepared by hydrolysis of the hydantoin XIV (Scheme D). Conditions for this trans- (B5, Scheme B) may be directly hydrolyzed using similar conditions to afford the substituted glycine compound directly.

Scheme D

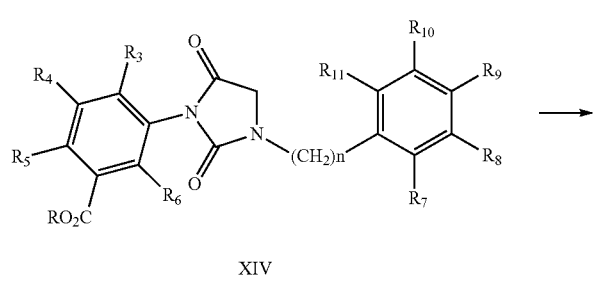

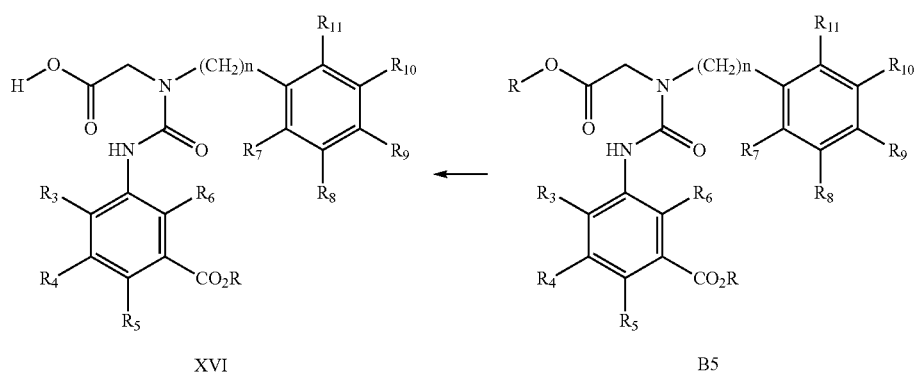

Methodology involving solid-phase-based combinatorial synthesis of the compounds of this invention can also be employed. In general, the methods used in solid phase organic synthesis involve immobilizing the substrate to be modified on a resin or other solid support such as pins, gel, beads, and lanterns. The solid phase chemistry has the advantage over solution phase chemistry in that purification of the modified substrates is greatly simplified. During the syntheses, the resin may be washed free of any byproducts or excess reagents before proceeding to the next reaction. Production of library compounds can be achieved by using this solid phase chemistry to produce a plurality of compounds in accord with any desired solid phase organic synthesis protocol. Combinatorial chemistry protocols can involve the use of multiple resins or other solid support, diversity reagents and modification of the substrates in diverse manners using various reagents.

Compounds of formula I can be prepared according to the solid phase-mediated routes depicted in Schemes E and F, below.

Scheme E

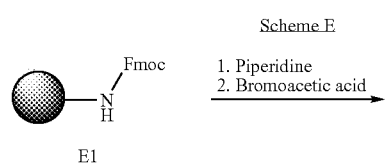

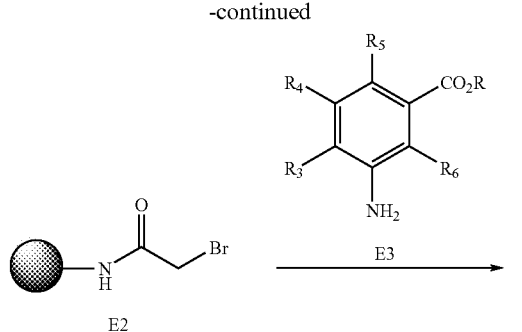

-continued

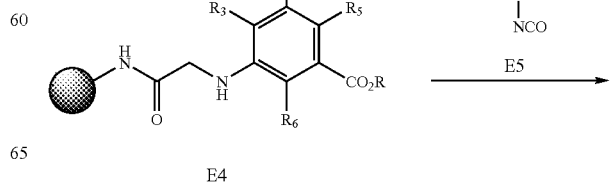

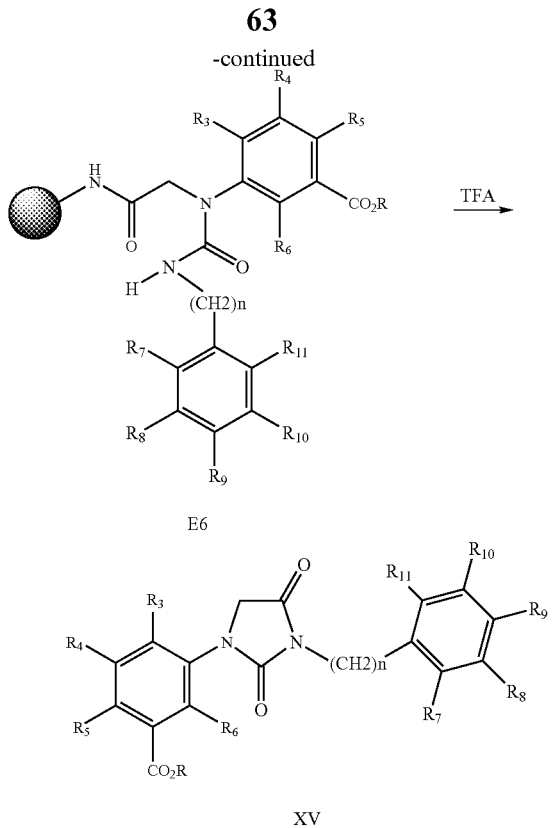

Commercially available, 4-(2',4'-dimethyoxyphenyl-Fmoc-aminomethyl)-phenoxy resin E1 can be used in this synthesis. Selective removal of the Fmoc-group can be achieved with basic cleavage with 20% piperidine in dimethyl-formamide. The amide formation between the primary amine and bromoacetic acid can be performed under usual amide formation reaction conditions using diisopropylcarbo-diimide or equivalents such as benzotriazole-1-yl-oxy-tris-pyrrolidino-phosphonium hexa-fluorophosphate, bromo-tris-pyrrolidino-phosphonium hexafluorophosphate, 1-ethyl-3-(3-dimethylaminopropyl)carbodiimide hydrochloride with or without diisopropyl-ethylamine in dimethylformamide. The bromoacetylated resin E2 can be used as a common linker for the synthesis of hydantoin library compounds with variation of the rest of the compound of structure XV as shown in Scheme E. The combinatorial chemistry method may use multi-reaction vessels, wherein a different combination of reagents can be used in each vessel to provide library compounds of interest. The resin-bound bromoacetylated intermediate was alkylated with a reagent E3 in the presence of a base reagent, such as diisopropylethylamine or diazobi-cycloundecene, in dimethylformamide. The reaction is usually performed at temperatures ranging from about ambient to the reflux temperature of the chosen solvent. The alkylated resin E4 can then be treated with an isocyanate reagent E5 to afford the urea derivative E6. The reaction is usually carried out in a solvent such as dichloromethane, dimethylformamide and at ambient temperature. The resin-bound urea intermediate can be cleaved and cyclized under acidic conditions such as 2M trifluoroacetic acid in dichloromethane, or 3M acetic acid in dichloromethane, to afford compounds of structure XV.

Compounds of structure XIV can also be prepared as shown in Scheme F, starting from commercially available halogenated resin F2 such as trityl chloride resin, bromom-ethyl resin or Merrifield resin. Y represents a halogenated group, e.g., chloro, bromo, flouro or iodo. The intermediate F3 can be obtained by esterification of F1 with halogenated resin in the presence of a base such as N-methylmorpholine, triethylamine, or diisopropylethylamine in an inert solvent such as dichloromethane, tetrahydrofuran and dimethylformamide or mixtures. Selective removal of the Fmoc protecting group can be achieved by basic cleavage with 25% piperidine in dimethylformamide. The amide formation between the deprotected aniline F4 and bromoacetic acid can be conveniently carried out under common amide formation reactions using diisopropylcarbodiimide or equivalents such as 1-ethyl-3-(3-dimethylaminopropyl)carbodiimide hydrochloride, benzotriazole-1-yl-oxy-tris-pyrrolidino-phosphonium hexafluorophosphate, bromo-tris-pyrrolidino-phosphonium hexafluorophosphate with or without diisopropylethylamine. The intermediate F5 can be used as a common intermediate for the synthesis of hydantoin analogs with variation of the rest of the molecule of structure XIV. The combinatorial chemistry method can use multi-reaction vessels, where a different combination of reagents used in each vessel to provide library compounds of interest. The resin-bound intermediate F7 can be obtained by N-alkylation of F5 with the primary amine F6 in an inert solvent such as dichloromethane, tetrahydrofuran and dimethylformamide or mixtures with or without diisopropylethylamine. The cyclic urea formation can be performed by using phosgene or equivalents such as carbonyldiimidazole, disuccinimidyl carbonate, or p-nitrohenyl chloroformate. The reaction involves reacting the alkylated substrate F7 with the phosgene or equivalents F8 in the presence of a base such as N-methylmorpholine, triethylamine, or diisopropylethylamine in an inert solvent such as dichloromethane, tetrahydrofuran and dimethylformamide or mixtures. Here, L' represents a group activated for displacement, such as imidazolyl, succinimidyl or phenoxy. The resin-bound intermediate F9 can be cleaved under acidic conditions such as 2M trifluoroacetic acid in dichloromethane, or 1M aqueous hydrochloric acid, to afford a compound of structure XIV.

Scheme F

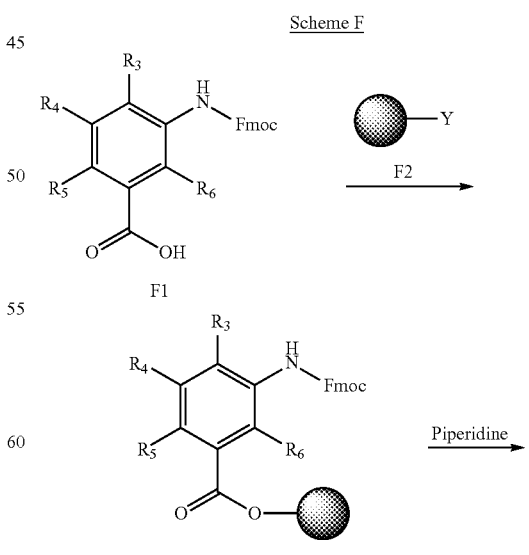

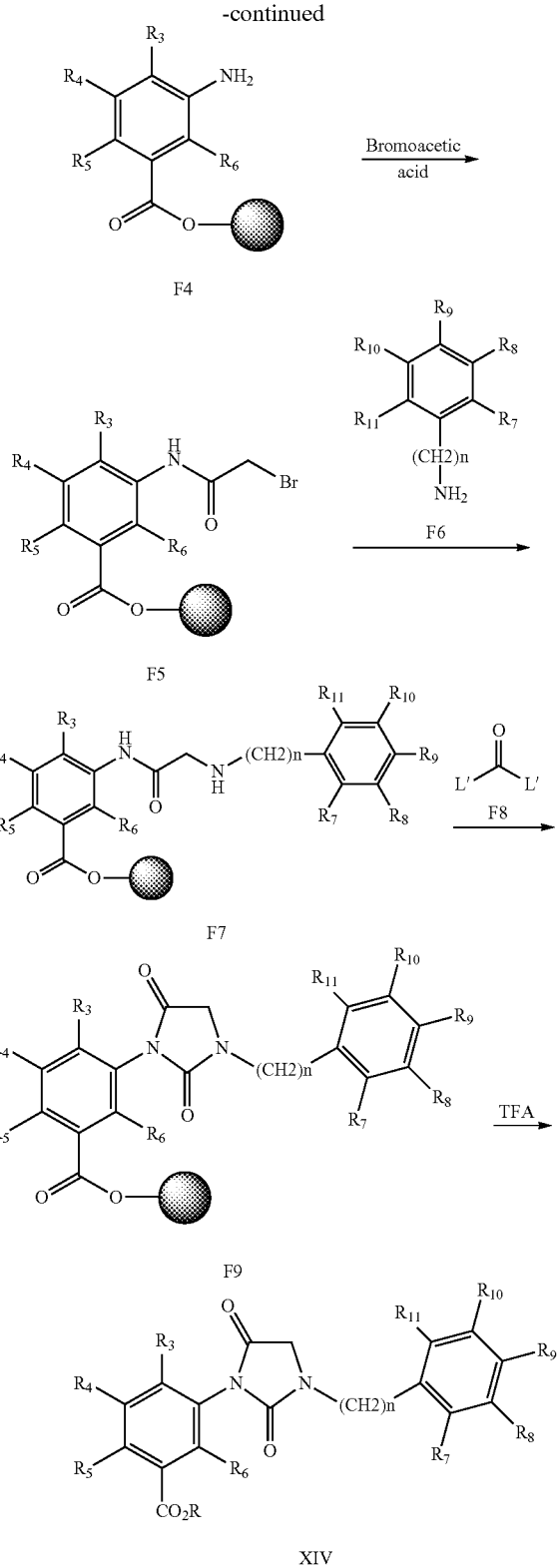

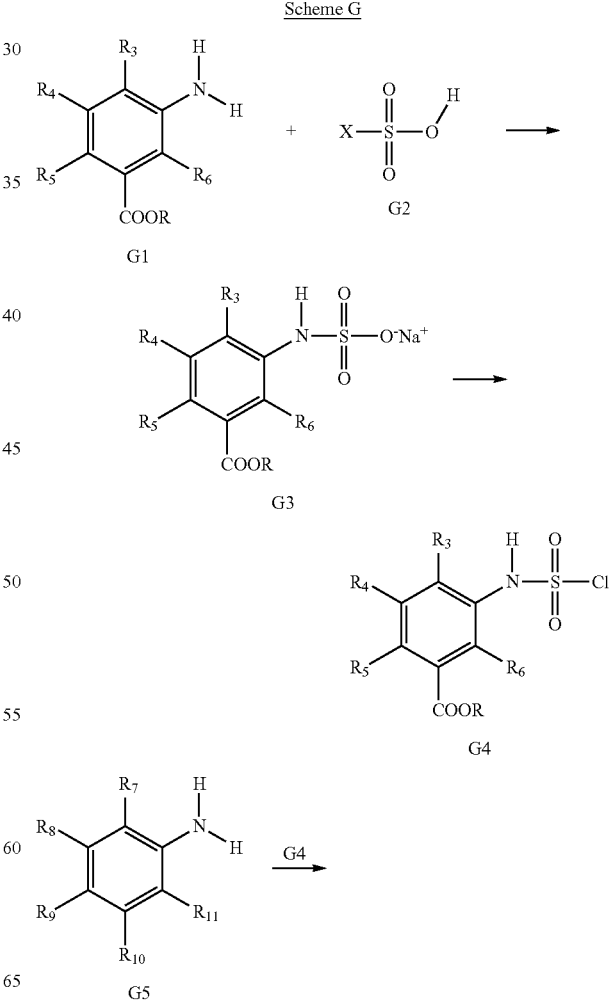

form or 1,2-dichloroethane, and at temperatures ranging from about 0° C. to about ambient temperature. The product is isolated as the sulfamic acid salt by extraction with an aqueous base such as sodium carbonate or sodium hydroxide. The sulfamic acid salt compound G3 is treated with a halogenating agent such as phosphorous oxychloride or phosphorous pentachloride in an unreactive solvent such as toluene or methylene chloride at temperatures ranging from ambient to reflux of the chosen solvent to afford the sulfamoyl chloride compound G4. The sulfamoyl chloride is then coupled with an amine compound G5. The coupling of compounds G4 and G5 to give sulfamide G6 can be performed in a suitably unreactive solvent, such as toluene, xylene, or dichloromethane, or even a mixture of such solvents (to effect maximum solubilization). The presence of a tertiary amine reagent (such as diisopropylethylamine or triethylamine) will often favorably catalyze the coupling reaction. Temperatures of the reaction range from about ambient to reflux of the chosen solvent. A ring-closure reaction on sulfamide compound G6 can be effected by the treatment with a difunctional alkylating agent such as 1,2-dibromoethane or 1,3-diiodopropane and a suitable base reagent such potassium carbonate in an unreactive solvent such as acetonitrile or dimethylformamide to give compounds of structure XVII.

Compounds of structure XVII can be prepared by the methodology depicted in Scheme G, below. An amine compound G1 is sulfonylated with a reagent G2, wherein the group L represents some leaving group, e.g., chloro, bromo, iodo or trifluoromethoxy. The reaction is usually performed in a halogenated solvent such as methylene chloride, chloro-

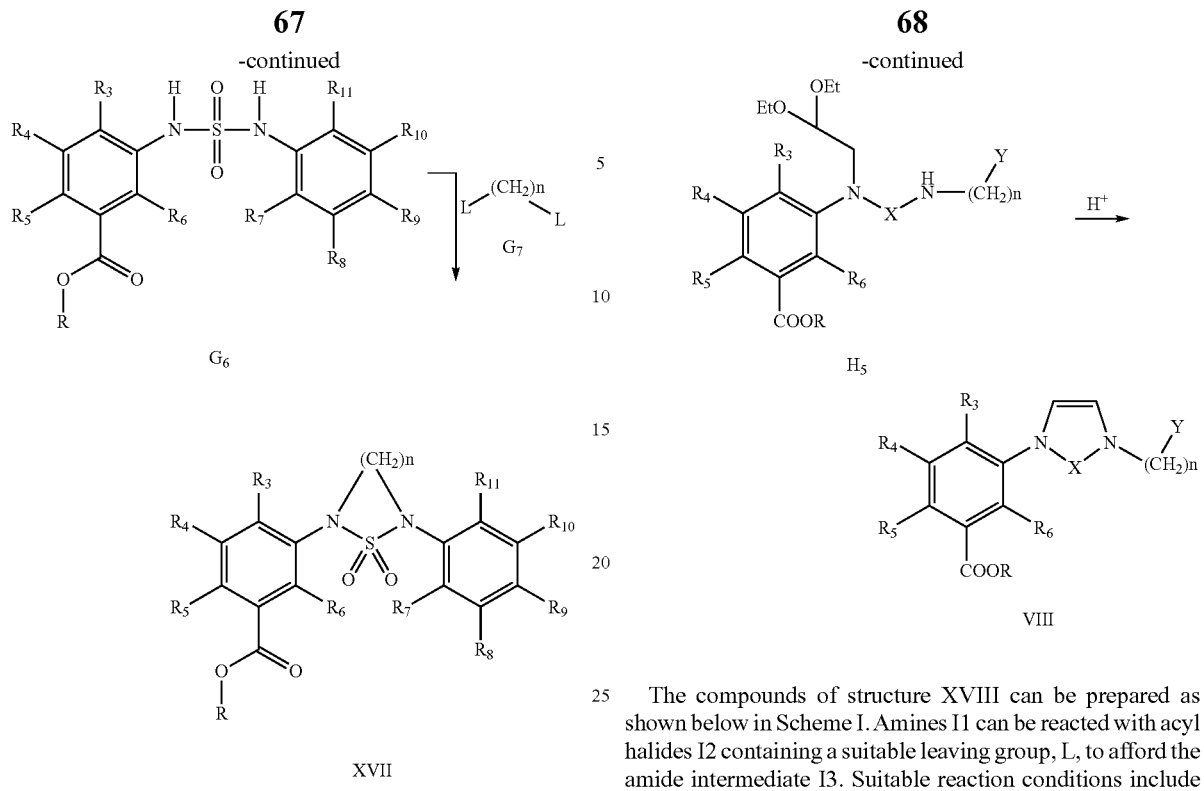

Compounds of structure VIII can be prepared as shown in Scheme H, below. Commercially available amines H1 can be treated with protected aldehydes H2 containing a suitable leaving group to give the substituted amines H3. The reaction may be performed in the presence of an inorganic base such as $K_2CO_3$ in a suitable organic solvent with heating. The amine can be further reacted with an isocyanate or isothiocyanate H4 (W=O or S) to give the urea or thiourea H5. Deprotection of the protected aldehyde and concomitant cyclization can be carried out in acid with or without an organic solvent as diluent to afford compounds of structure VIII.

The compounds of structure XVIII can be prepared as shown below in Scheme I. Amines I1 can be reacted with acyl halides I2 containing a suitable leaving group, L, to afford the amide intermediate I3. Suitable reaction conditions include the employment of an appropriate organic solvent and an inorganic or organic base to neutralize the acid formed in the reaction. The amino amide intermediate I5 is formed upon reaction of the amide I3 with an amine I4 in the presence of a polar organic solvent and an inorganic base such as $K_2CO_3$. Conversion of the amino amide I5 to the diamine I6 is accomplished by reaction of a reducing reagent such as borane-THF or borane dimethyl sulfide in a suitable solvent at ambient to elevated temperature. Cyclization of I6 with I7, where L' represents a leaving group such as halide, imidazole or triazole, in a suitable solvent affords the compounds of structure XVIII.

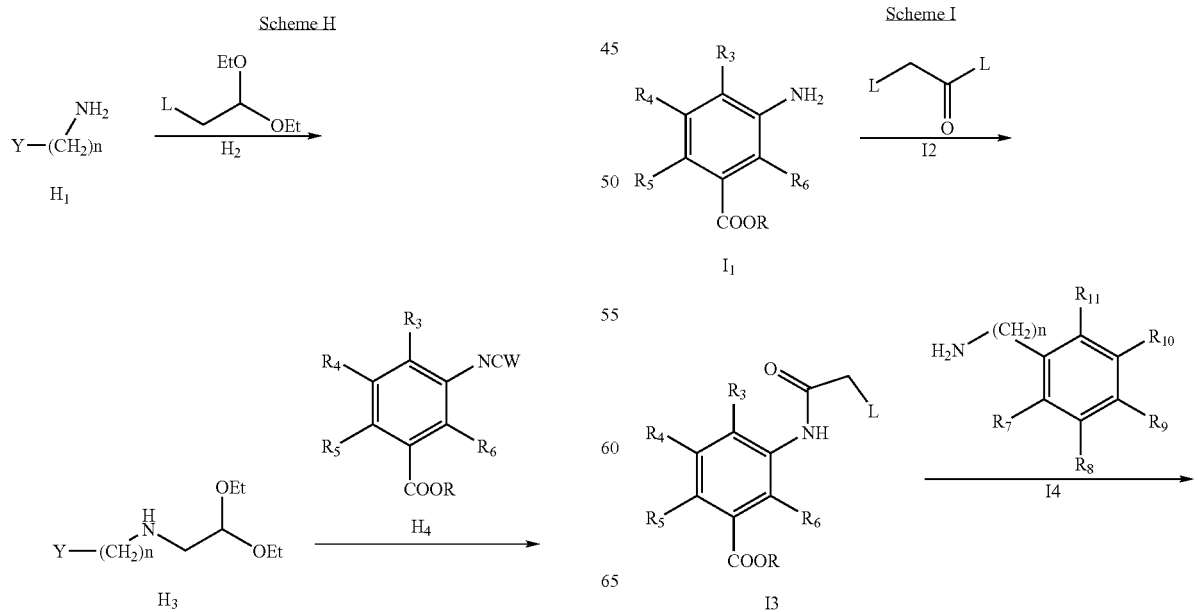

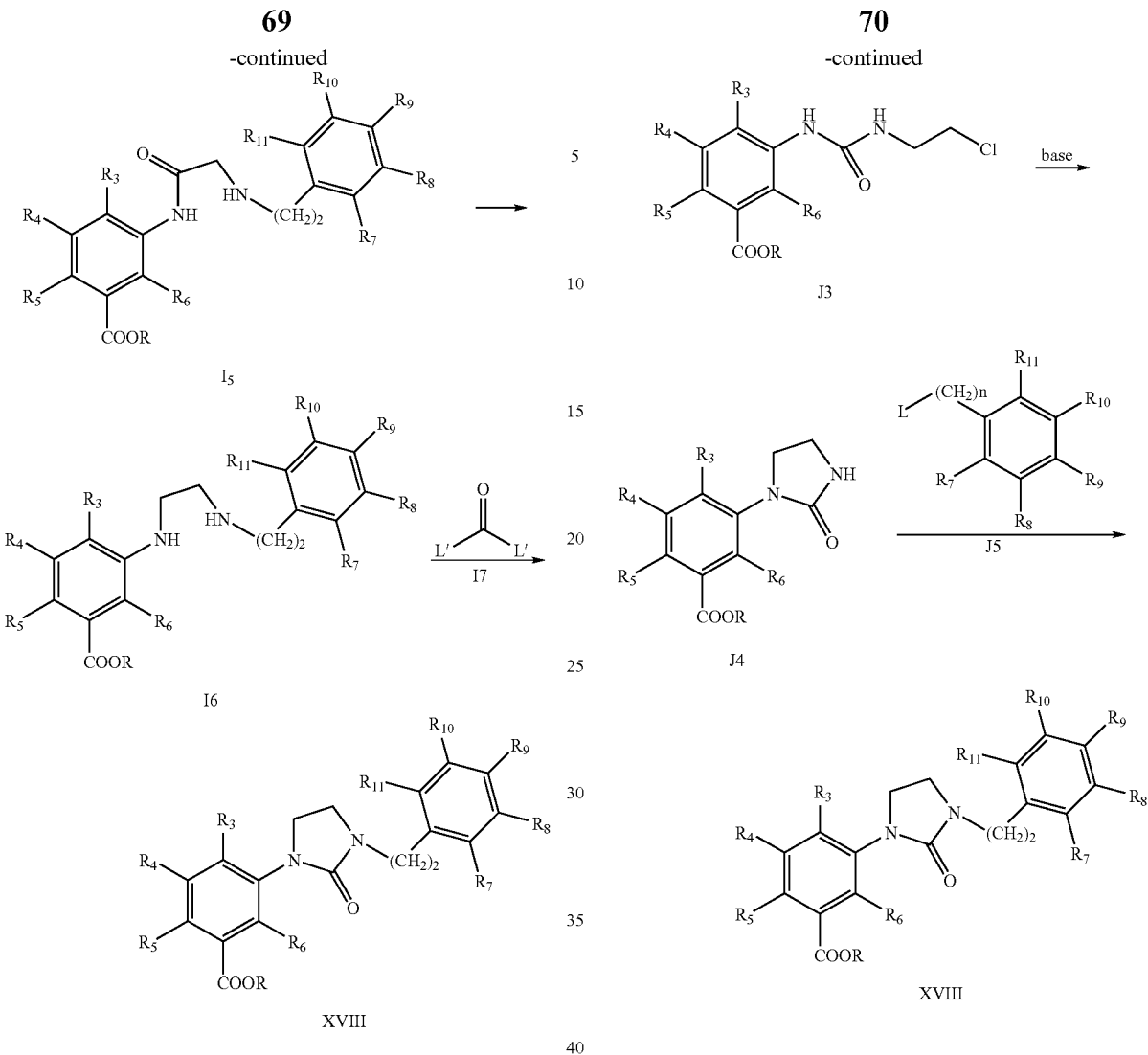

Compounds of structure XVIII can also be prepared as described in Scheme J below. Amines J1 can be reacted with 2-(chloroethyl)isocyanate J2 to afford the intermediate urea compounds J3. The reaction can be performed in a variety of solvents at room temperature or at elevated temperatures. The intermediate urea can then be cyclized in the presence of an inorganic or organic base in a suitable organic solvent to form the intermediate J4. Coupling between the amine J4 and compound J5 can be accomplished using an inorganic metalloid species such as a copper halide in the presence of a suitable amine ligand and an inorganic base to afford the compounds of structure XVIII.

Compounds of structure XVIII can also be prepared as shown below in Scheme K. Compounds of type K1 can be reacted with 2-(chloroethyl)isocyanate K2 to form urea compounds K3. The reaction can be performed in a variety of solvents at room temperature or at elevated temperatures. The intermediate urea can then be cyclized in the presence of an inorganic or organic base in a suitable organic solvent to form the intermediate K4. Coupling between the amine J4 and compound J5 can be accomplished using an inorganic metalloid species such as a copper halide in the presence of a suitable amine ligand and an inorganic base to afford the compounds of structure XVIII.

Scheme J

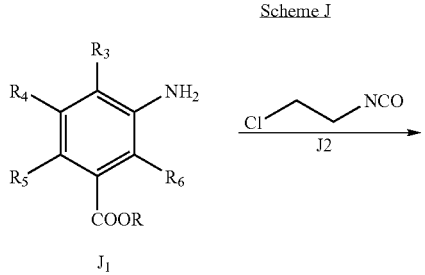

Scheme K

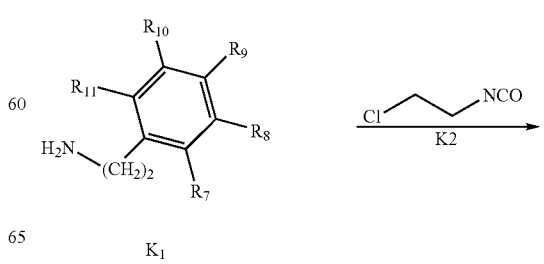

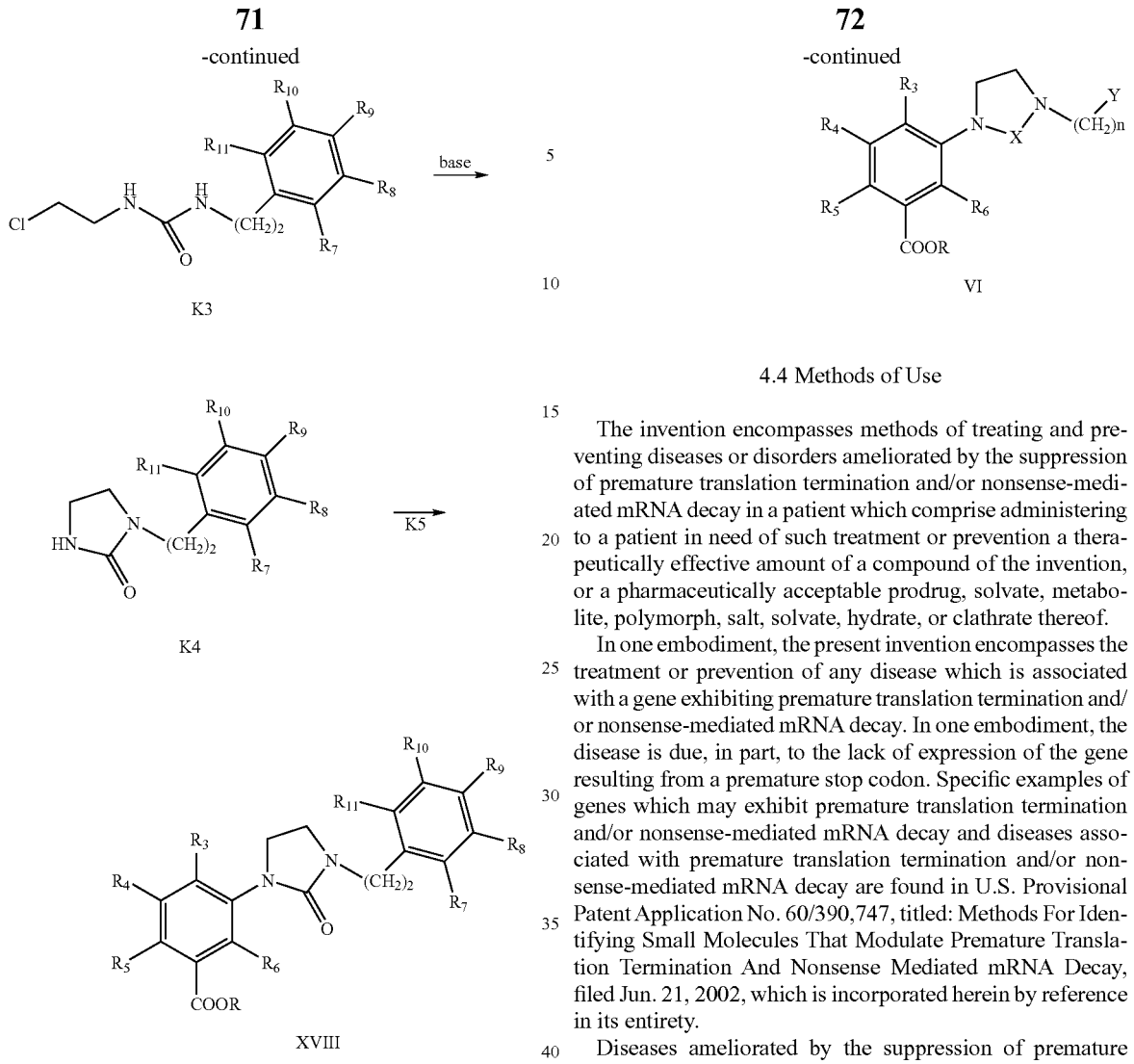

Compounds of structure VI can be prepared as shown below in Scheme L by reduction of structure VIII using known methodology. The reduction may be carried out using a variety of methods. For example, heterogeneous transition metal catalysts (e.g., palladium or platinum) in the presence of a reductant (e.g., hydrogen) and suitable polar or nonpolar organic solvent or mixtures can effectively convert structure VIII to Structure VI.

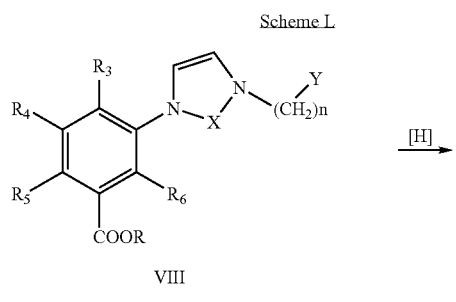

4.4 Methods of Use

The invention encompasses methods of treating and preventing diseases or disorders ameliorated by the suppression of premature translation termination and/or nonsense-mediated mRNA decay in a patient which comprise administering to a patient in need of such treatment or prevention a therapeutically effective amount of a compound of the invention, or a pharmaceutically acceptable prodrug, solvate, metabolite, polymorph, salt, solvate, hydrate, or clathrate thereof.

In one embodiment, the present invention encompasses the treatment or prevention of any disease which is associated with a gene exhibiting premature translation termination and/or nonsense-mediated mRNA decay. In one embodiment, the disease is due, in part, to the lack of expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Provisional Patent Application No. 60/390,747, titled: Methods For Identifying Small Molecules That Modulate Premature Translation Termination And Nonsense Mediated mRNA Decay, filed Jun. 21, 2002, which is incorporated herein by reference in its entirety.

Diseases ameliorated by the suppression of premature translation termination and/or nonsense-mediated mRNA decay include, but are not limited to: a genetic disease, cancer, an autoimmune disease, a blood disease, a collagen disease, diabetes, a neurodegenerative disease, a proliferative disease, a cardiovascular disease, a pulmonary disease, an inflammatory disease or central nervous system disease.

Specific genetic diseases within the scope of the methods of the invention include, but are not limited to, amyloidosis, hemophilia, Alzheimer's disease, Tay Sachs disease, Niemann Pick disease, atherosclerosis, giantism, dwarfism, hypothyroidism, hyperthyroidism, aging, obesity, Parkinson's disease, cystic fibrosis, muscular dystrophy, heart disease, kidney stones, ataxia-telangiectasia, familial hypercholesterolemia, retinitis pigmentosa, Duchenne muscular dystrophy, and Marfan syndrome. Both solid tumor and other cancers are included within the methods of the invention.

In another embodiment, the genetic disease is an autoimmune disease. In a preferred embodiment, the autoimmune disease is rheumatoid arthritis or graft versus host disease.

In another embodiment, the genetic disease is a blood disease. In a preferred embodiment, the blood disease is hemophilia, Von Willebrand disease, ataxia-telangiectasia, β-thalassemia or kidney stones.

In another embodiment, the genetic disease is a collagen disease. In a embodiment, the collagen disease is osteogenesis imperfecta or cirrhosis.

In another embodiment, the genetic disease is diabetes.

In another embodiment, the genetic disease is an inflammatory disease. In a preferred embodiment, the inflammatory disease is arthritis, rheumatoid arthritis or osteoarthritis.

In another embodiment, the genetic disease is a central nervous system disease. In one embodiment the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, late infantile neuronal ceroid lipofuscinosis (LINCL) or Parkinson's disease.

In another embodiment, the genetic disease is cancer. In a preferred embodiment, the cancer is of the head and neck, eye, skin, mouth, throat, esophagus, chest, bone, lung, colon, sigmoid, rectum, stomach, prostate, breast, ovaries, kidney, liver, pancreas, brain, intestine, heart or adrenals.

In another preferred embodiment, the cancer is associated with the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2):115-26; Radig et al., 1998, Hum Pathol. 29(11):1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100(1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8):1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties). Any disease associated with a p53 gene encoding a premature translation codon including, but not limited to, the nonsense mutations described in the references cited above, can be treated or prevented by compounds of formula I. Without be limited by theory, the compounds mediate premature translation termination and/or nonsense-mediated mRNA decay.

In other embodiments, diseases to be treated or prevented by administering to a patient in need thereof an effective amount of a compound of formula I include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. See e.g., *Harrison's Principles of Internal Medicine*, Eugene Braunwald et al., eds., pp. 491-762 (15$^{th}$ ed. 2001).

In a preferred embodiment, the invention encompasses a method of treating or preventing a disease ameliorated by modulation of premature translation termination and/or nonsense-mediated mRNA decay, or ameliorating one or more symptoms associated therewith comprising contacting a cell with an effective amount of a compound of formula I. Cells encompassed by the present methods include animal cells, mammalian cells, bacterial cells, plant cells and virally infected cells. In one embodiment, the nonsense codon was present in the progenitor DNA. In another embodiment, the nonsense codon resulted from mutagenesis.

In certain embodiments, a compound of formula I, or a pharmaceutically acceptable salt thereof, is administered to a patient, preferably a mammal, more preferably a human, as a preventative measure against a disease associated with premature translation termination and/or nonsense-mediated mRNA decay.

In a preferred embodiment, it is first determined that the patient is suffering from a disease associate with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subject to Southern Blot, polymerase chain reaction (PCR), use of the Short Tandem Repeat (STR), or polymorphic length restriction fragments (RFLP) analysis to determine if a nonsense mutation is present in the DNA of the patient. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of formula I can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell).

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; antiemetics; β-adrenergic blockers; anticonvulsants; antidepressants; $Ca^{2+}$-channel blockers; anticancer agent and mixtures thereof.

In certain embodiments, the compounds of formula I can be administered or formulated in combination with anticancer agents. Suitable anticancer agents include, but are not limited to, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan and taxol.

In certain embodiments, the compounds of formula I can be administered or formulated in combination with antibiotics. In certain embodiments, the antibiotic is a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®))). In a preferred embodiment, the antibiotic is active against *Pseudomonas aeruginosa*.

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent.

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 0.1 mg to about 2000 mg per day. In one embodiment, the compound of formula I is given as a single once-a-day dose. In another embodiment, the compound of formula I is given as divided doses throughout a day. More specifically, the daily dose is administered in a single dose or in equally divided doses. Preferably, a daily dose range should be from about 5 mg to about 500 mg per day, more preferably, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

4.5 Pharmaceutical Compositions

Pharmaceutical compositions and single unit dosage forms comprising a compound of the invention, or a pharmaceutically acceptable polymorph, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Pharmaceutical compositions and dosage forms of the invention comprise a compound of the invention, or a pharmaceutically acceptable prodrug, polymorph, salt, solvate, hydrate, or clathrate thereof. Pharmaceutical compositions and dosage forms of the invention typically also comprise one or more pharmaceutically acceptable excipients.

A particular pharmaceutical composition encompassed by this embodiment comprises a compound of the invention, or a pharmaceutically acceptable polymorph, prodrug, salt, solvate, hydrate, or clathrate thereof, and at least one additional therapeutic agent. Examples of additional therapeutic agents include, but are not limited to: anti-cancer drugs and anti-inflammation therapies including, but not limited to, those listed above in Section 4.3.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18$^{th}$ ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of the invention, or a pharmaceutically acceptable salt, solvate, clathrate, hydrate, polymorph or prodrug thereof lie within the range of from about 0.1 mg to about 2000 mg per day, given as a single once-a-day dose in the morning but preferably as divided doses throughout the day taken with food. More preferably, the daily dose is administered twice daily in equally divided doses. Preferably, a daily dose range should be from about 5 mg to about 500 mg per day, more preferably, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

4.5.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18$^{th}$ ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.5.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Parenteral dosage forms are preferred for the methods of preventing, treating or managing disease in a cancer patient.

4.5.4 Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., *Remington's Pharmaceutical Sciences*, 18$^{th}$ eds., Mack Publishing, Easton Pa. (1990); and *Introduction to Pharmaceutical Dosage Forms*, 4$^{th}$ ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 18$^{th}$ eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.5.5 Mucosal Dosage Forms and Lung Delivery

Mucosal dosage forms of the invention include, but are not limited to, ophthalmic solutions, sprays and aerosols, or other forms known to one of skill in the art. See, e.g., *Remington's Pharmaceutical Sciences*, 18$^{th}$ eds., Mack Publishing, Easton Pa. (1990); and *Introduction to Pharmaceutical Dosage Forms*, 4$^{th}$ ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of formula I can also be administered directly to the lung by inhalation (see e.g., Tong et al., PCT Application, WO 97/39745; Clark et al, PCT Application, WO 99/47196, which are herein incorporated by reference). For administration by inhalation, a compound of formula I can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound of formula I directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound of formula I to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of formula I to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a compound of formula I to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compound of formula I, delivered by nebulizer devices, is currently under investigation as a treatment for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In a particularly preferred embodiment, an electrohydrodynamic ("EHD") aerosol device is used to deliver a compound of formula I to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the compound of formula I formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of a compound of formula I will be known to the skilled artisan and are within the scope of the invention.

Liquid drug formulations suitable for use with nebulizers and liquid spray devices and EHD aerosol devices will typically include a compound of formula I with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of a compound of formula I. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference) A compound of formula I can also be formulated in rectal or vaginal compositions such as suppositories or retention enemas, e.g., containing conventional suppository bases such as cocoa butter or other glycerides.

In addition to the formulations described previously, a compound of formula I can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver a compound of formula I. Certain organic solvents such as dimethylsulfoxide can also be employed, although usually at the cost of greater toxicity. A compound of formula I can also be delivered in a controlled release system. In one embodiment, a pump can be oused (Sefton, CRC Crit. Ref Biomed Eng., 1987, 14, 201; Buchwald et al., Surgery, 1980, 88, 507; Saudek et al., N. Engl. J Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989, 25, 351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g. Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., *Remington's Pharmaceutical Sciences,* $18^{th}$ eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5. EXAMPLES

5.1 Example 1

SYNTHESIS OF 3-[3-(4-ISOPROPYL-PHENYL)-UREIDO]-BENZOIC ACID (COMPOUND 8)

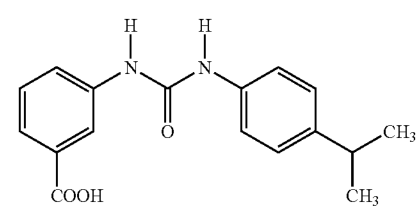

A solution of 3-aminobenzoic acid (0.46 g, 3.4 mmol) in dimethylformamide (20 mL) at 0° C. was treated with 4-isopropylphenyl isocyanate (0.59 mL, 3.7 mmol). After stirring for 20 h, the solution was poured into 200 mL water, and the resulting precipitate was collected by filtration, washed with water and tetrahydrofuran, and dried under vacuum to afford the title product (0.85 g, 2.9 mmol, 85%) as a powder (m.p. 295-300° C.). TLC Rf 0.20 (ethyl acetate). $^{1}H$ NMR (d6-DMSO, 300 MHz): δ 8.82 (1H, s), 8.57 (1H, s), 8.09 (1H, t, J=1.8 Hz), 7.58 (1H, dd, J=8.1, 1.1 Hz), 7.51 (1H, d, J=7.8

Hz), 7.36 (1H, t, J=8.0 Hz), 7.34 (2H, d, J=8.4 Hz), 7.12 (2H, d, J=8.4 Hz), 2.82 (1H, heptet, J=6.9 Hz), 1.17 (6H, d, J=6.9 Hz). MS (ES+): 299

5.2 Example 2

SYNTHESIS OF 3-[3-(4-TERT-BUTYLPHENYL)-UREIDO]-BENZOIC ACID (COMPOUND 33)

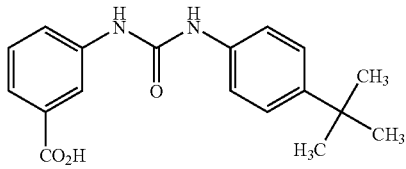

A solution of methyl 3-aminobenzoate (10.0 g, 66.1 mmol) and pyridine (6 mL) in dichloromethane (100 mL) was cooled to 0° C., and a solution of 4-nitrophenylchloroformate (13.4 g, 66.6 mmol) in dichloromethane (10 mL) was added dropwise of 30 min. The resulting solution was stirred for 20 h, then partitioned between water and dichloromethane (400 mL each). The organic layer was washed with 0.5 N aq. HCl and brine, and the aqueous phases were back-extracted in sequence with dichloromethane. The organic extracts were combined, dried over magnesium sulfate, filtered and evaporated. The resulting solid was triturated with ether, collected by filtration and dried under vacuum to afford the product, methyl-3-(N-(4-nitrophenoxycarbonyl)amino)benzoate (19.7 g, 62.3 mmol, 94%). m.p. 184-186° C. TLC RF 0.33 (30:70 ethyl acetate-hexane). $^1$H NMR (300 MHz, CDCl3): δ 9.38 (1H, s), 8.28 (H, d, J=9.1 Hz), 8.22 (1H, d, J=9.1 Hz), 8.12 (1H, d), 7.76 (1H, d, J=7 Hz), 7.71 (1H, d, J=7 Hz), 7.45 (1H, d, J=9 Hz), 7.35 (1H, t, J=7 Hz), 7.33 (1H, d, J=9 Hz), 3.85 (3H, s). MS (ESI): m/e 334 (21), 142 (100).

A solution of methyl-3-[N-(4-nitrophenoxycarbonyl) amino]benzoate (0.19 g, 0.60 mmol) and 4-tert-butylaniline (0.10 mL, 0.60 mmol) in pyridine (5 mL) was heated to reflux for 16 h. The solution was cooled and evaporated, and the residual material was taken up in ethyl acetate (100 mL). This was washed with 1 N aq. sodium hydroxide and brine, dried over magnesium sulfate, filtered and evaporated. The residual solid was triturated with ether, collected by filtration and dried under vacuum to afford the product, methyl-3-[3-(4-tert-butylphenyl)-ureido]-benzoate, as a solid (0.19 g, 0.58 mmol, 97%).

A solution of methyl-3-[3-(4-tert-butylphenyl)-ureido]-benzoate (0.19 g, 0.58 mmol) in pyridine (15 mL) was treated with anhydrous lithium iodide (0.78 g, 6.0 mmol), and the resulting solution was heated to reflux for 20 h. The solution was cooled and partially evaporated, and the residual material was partitioned between 1 N aq. HCl and ethyl acetate. The aqueous layer was extracted with more ethyl acetate, and the organic extracts were washed with brine, combined, dried over magnesium sulfate, filtered, and evaporated. The remaining powdery solid was triturated with ether, collected by filtration and dried under vacuum to afford the title compound (0.12 g, 0.39 mmol, 66%). m.p. 147-148° C. $^1$H NMR (d$_6$-DMSO, 300 MHz): d 8.58 (1H, s), 8.10 (1H, t, J=2 Hz), 7.72-7.62 (2H, m), 7.40-7.25 (5H,m), 6.53 (1H, s), 1.25 (9H, s).

5.3 Example 3

SYNTHESIS OF 3-[3-(4-ISOPROPYLPHENYL)-2, 5-DIOXO-IMIDAZOLIDIN-1-YL]-BENZOIC ACID SODIUM SALT (COMPOUND 1)

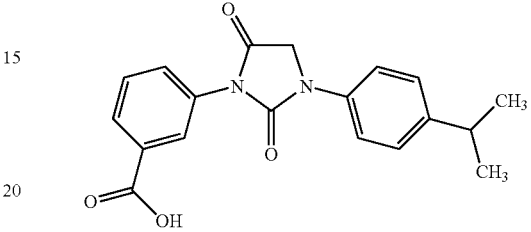

A solution of 4-isopropylaniline (5.05 g, 37.3 mmol), methyl bromoacetate (5.99 g, 39.2 mmol) and anhydrous sodium acetate (3.21 g) in absolute methanol (30 mL) was heated to reflux for 2 h. The solution was cooled and poured into 300 mL water. The resulting solid was collected by filtration and recrystallized from ethanol/water to afford pure product, methyl-2-(4-isopropylanilino)acetate, m.p. 35-36° C. (4.53 g, 55%). $^1$H NMR (CDCl$_3$, 300 MHz): δ 7.06 (2H, d, J=8.2 Hz), 6.57 (2H, d, J=8.2 Hz), 4.18 (1H, v br), 3.90 (2H, s), 3.78 (3H, s), 2.81 (1H, m, J=7.0 Hz), 1.20 (6H, d, J=7.0 Hz). Mass spectrum (ES+): m/z 209 (3), 208 (31), 148 (100).

A solution of methyl-2-(4-isopropylanilino)acetate (1.10 g, 5.31 mmol) in toluene (30 mL) was treated with methyl 3-isocyanatobenzoate (1.03 g), and the resulting solution was stirred at ambient temperature for 20 h. The reaction mixture was evaporated, and a portion (0.6 g) of the resulting solid material used directly in the next step. The compound was dissolved in methanol, and treated with sodium methoxide (0.84 mL of 0.5 M in methanol). The resulting solution was stirred for 1 h, then evaporated and partitioned between water and ethyl acetate (50 mL each). The organic extract was washed with brine, dried over magnesium sulfate, filtered and evaporated. The residual material was separated by preparative thin-layer chromatography (silica gel, 30:70 ethyl acetate-hexane) to afford pure product, methyl-3-[3-(4-isopropylphenyl)-2,5-DIOXO-imidazolidin-1-yl]-benzoate, as a waxy solid. $^1$H NMR (CDCl$_3$, 300 MHz): δ 8.16 (1H, t, J=1.8 Hz), 8.07 (1H, dt, J=7.6, 1.5 Hz), 7.67 (1H, ddd, J=8.0, 2.0, 1.1 Hz), 7.56 (1H, t, J=7.9 Hz), 7.51 (2H, d, J=8.8 Hz), 7.27 (2H, d, J=8.8 Hz), 4.47 (2H, s), 3.92 (3H, s), 2.91 (1H, m, J=7.0 Hz), 1.25 (6H, d, J=7.0 Hz). Mass spectrum (ES+): m/z 353 (36), 321 (100).

A solution of methyl-3-[3-(4-isopropylphenyl)-2,5-dioxo-imidazolidin-1-yl]-benzoate (0.69 g, 1.96 mmol) and lithium iodide (2.62 g) in pyridine (10 mL) was heated to reflux for 40 h. The solution was cooled and evaporated, and the residue was partitioned between ethyl acetate and 1 N aqueous HCl. The organic layer was washed with water and brine, then dried over magnesium sulfate, filtered and evaporated. The residual material was separated by column chromatography (silica gel, 50:50 ethyl acetate-hexane then ethyl acetate) to afford the product, 3-[3-(4-isopropylphenyl)-2,5-dioxo-imidazolidin-1-yl]-benzoic acid, as a powder (0.33 g, 0.98 mmol, 50%). m.p. 224-226° C. TLC Rf (20:80 CH3OH—CH2Cl2)

0.3. ¹H NMR (CDCl₃, 300 MHz): δ 8.24 (1H, t, J=2 Hz), 8.14 (1H, dt, J=8, 2 Hz), 7.73 (1H, dt, J=8, 2, 1 Hz), 7.61 (1H, t, J=7 Hz), 7.51 (2H, d, J=8 Hz), 7.28 (2H, d, J=8 Hz), 4.50 (2H, s), 2.92 (1H, m, J=7 Hz), 1.25 (6H, d, J=7 Hz). Mass spectrum (ES+): m/z 340 (21), 339 (100). Elemental analysis: calculated for $C_{19}H_{18}N_2O_4 \cdot 0.149 H_2O$ C 66.91, H 5.41, N 8.21; observed C 66.82, H 5.17, N 8.19.

5.4 Example 4

SYNTHESIS OF 3-[3-(4-ISOPROPYLPHENYL)-2,5-DIOXO-IMIDAZOLIDIN-1-YL]-BENZOIC ACID SODIUM SALT (SODIUM SALT OF COMPOUND 1)

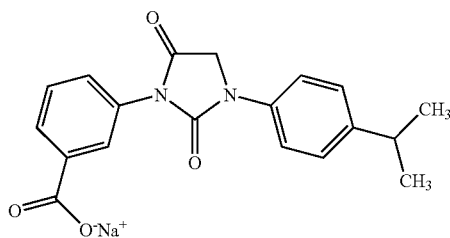

A portion of the 3-[3-(4-isopropylphenyl)-2,5-dioxo-imidazolidin-1-yl]-benzoic acid sodium hydride suspension (116 mg, 55% w/w) was washed free of mineral oil with hexane, the hexane decanted off, and the remaining solid taken up 5 mL THF. The resulting suspension was cooled in an ice bath while a solution of 3-[3-(4-isopropylphenyl)-2,5-dioxo-imidazolidin-1-yl]-benzoic acid (0.90 g, 2.66 mmol) in THF (10 mL) was slowly added. After hydrogen gas evolution was complete, the mixture was stirred for an additional 18 h, filtered free of excess sodium hydride, and evaporated. The resulting solid was triturated with acetone, collected by filtration, washed with hexane, and dried under vacuum to afford the title compound (0.51 g, 1.42 mmol, 53%). m.p. 281-284° C. Mass spectrum (ES+): m/z 340 (14), 339 (100). Elemental analysis: calculated for $C_{19}H_{17}N_2O_4Na \cdot 1.1 H_2O$ C 60.03, H 5.09, N 7.37; observed C 59.99, H 5.02, N 7.26.

5.5 Example 5

SYNTHESIS OF 3-[3-(4-TERT-BUTYLPHENYL)-2,5-DIOXO-IMIDAZOLIDIN-1-YL]-BENZOIC ACID (COMPOUND 28)

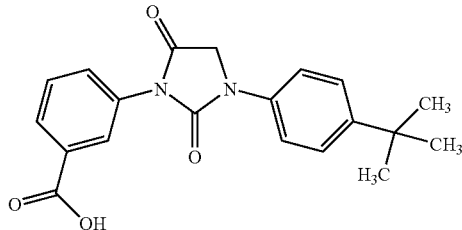

A solution of 4-tert-butylaniline (3.02 g, 20.2 mmol) and benzyl bromoacetate (4.70 g, 20.5 mmol) in anhydrous methanol (40 mL) was treated with sodium ethoxide (2.08 g) at ambient temperature with stirring for 6 h. The mixture was evaporated, and the residue was partitioned between ethyl acetate and water. The aqueous layer was extracted with more ethyl acetate, and the extracts were combined, dried over anhydrous sodium sulfate, filtered and evaporated to afford the product (3.85 g), benzyl-N-(4-tert-butylphenyl)glycine, as a brown-colored oil, sufficiently pure for the next step. ¹H NMR (CDCl₃, 300 MHz): δ 7.40-7.35 (5H, m), 7.23 (2H, d, J=8 Hz), 6.59 (2H, d, J=8 Hz), 5.22 (2H, s), 4.21 (1H, br s), 3.98 (2H, s), 1.29 (9H, s).

A solution of benzyl-N-(4-tert-butylphenyl)glycine (1.20 g, 4.04 mmol), 3-aminobenzoic acid (0.55 g, 4.01 mmol) and diphenylcarbonate (0.87 g, 4.06 mmol) in cresol (4 mL) was heated to reflux for 5 h. The mixture was cooled, poured into 20 mL diethyl ether, and filtered. The solid product as named in the title was dried under vacuum (1.10 g, 3.12 mmol, 78%). m.p. 256-258° C. ¹H NMR (d₆-DMSO, 300 MHz): δ 8.01 (1H, t, J=2 Hz), 7.98 (1H, dt, J=8, 2 Hz), 7.70-7.62 (2H, m), 7.60 (2H, d, J=8 Hz), 7.43 (2H, d, J=8 Hz), 4.60 (2H, s), 1.28 (9H, s). Mass spectrum (ES+): m/z 354 (23), 353 (100). Elemental analysis: calculated for $C_{20}H_{20}N_2O_4$ C 68.07, H 5.85, N 7.61; observed C 68.17, H 5.72, N 7.95.

5.6 Example 6

SYNTHESIS OF 3-[1-(4-ISOPROPYLPHENYL)-2,5-DIOXO-IMIDAZOLIDIN-3-YL]-BENZOIC ACID (COMPOUND 9)

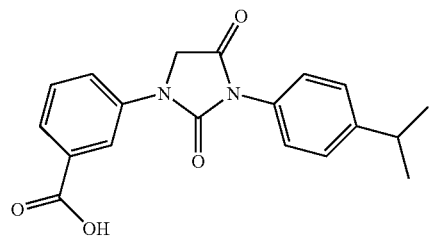

A solution of methyl 3-aminobenzoate (4.00 g, 26.5 mmol), methyl bromoacetate (4.05 g, 26.5 mmol) and sodium acetate (1.1 eq.) in methanol (30 mL) was stirred at ambient temperature for 48 h. The resulting white precipitate was collected by filtration, washed with a small amount of methanol, and dried under vacuum to afford methyl-N-(3-carbomethoxyphenyl)glycine (2.69 g, 12.1 mmol, 45%). ¹H NMR (CDCl₃, 300 MHz): δ 7.41 (1H, d, J=8 Hz), 7.28-7.20 (2H, m), 6.79 (1H, d, J=8 Hz), 4.43 (1H, br), 3.97 (2H, s), 3.90 (3H, s), 3.80 (3H, s).

A solution of methyl-N-(3-carbomethoxyphenyl)glycine (0.51 g, 2.28 mmol) and 4-isopropylphenyl isocyanate (0.40 g, 2.48 mmol) in xylene (5 mL) was heated to reflux for 20 h. The mixture was cooled, and 1 eq. triethylamine was added by syringe. The mixture was again heated to reflux for 24 h, then was partially evaporated. The crude condensation product thus obtained was taken directly into the next step.

The condensation product was treated with a methanolic solution of sodium methoxide (2 mL, 0.5 M), and the reaction mixture was stirred at ambient temperature for 20 h, then evaporated under high vacuum (to remove residual xylene from the first step). Methanol was added (ca. 2 mL), and the resulting solid (methyl 3-[1-(4-isopropylphenyl)-2,5-dioxo-imidazolidin-3-yl]-benzoate) was collected by filtration and dried under vacuum (0.30 g, 0.85 mmol, 30%). ¹H NMR (CDCl₃, 300 MHz): δ 8.09 (1H, t, J=2 Hz), 8.02 (1H, dt, J=8, 2 Hz), 7.84 (1H, dt, J=8, 2 Hz), 7.48 (1H, t, J=8 Hz), 7.33 (4H, s), 4.53 (2H, s), 3.92 (3H, s), 2.96 (1H, m, J=7 Hz), 1.25 (6H, d, J=7 Hz).

A solution of methyl 3-[1-(4-isopropylphenyl)-2,5-dioxo-imidazolidin-3-yl]-benzoate (0.30 g, 0.85 mmol) in pyridine (2 mL) was treated with anhydrous lithium iodide (1.5 g, 11.2 mmol), and the resulting mixture was heated to reflux for 4 h. The solution was cooled, evaporated and partitioned between ethyl acetate and 1N aq. HCl. The aqueous layer was extracted with more ethyl acetate, and the extracts were washed with satd. aq. brine, combined, dried over anhydrous magnesium sulfate, filtered and evaporated to afford the title product as a solid (0.21 g, 0.62 mmol, 73%), m.p. 249-252° C. $^1$H NMR (d$_6$-DMSO, 300 MHz): d 13.09 (1H, br), 8.29 (1H, t, J=2 Hz), 7.82 (1H, d, J=8 Hz), 7.72 (1H, d, J=8 Hz), 7.56 (1H, t, J=8 Hz), 7.38 (2H, d, J=8 Hz), 7.31 (2H, d, J=8 Hz), 4.62 (2H, s), 2.96 (1H, m, J=7 Hz), 1.22 (6H, d, J=7 Hz). Mass spectrum (ES+): m/z 340 (18), 339 (100). Elemental analysis: calculated for $C_{19}H_{18}N_2O_4$ C 67.45, H 5.32, N 8.28; observed C 67.26, H 5.10, N 8.12.

5.7 Example 7

SYNTHESIS OF 3-[3-HYDROXY CARBONYLMETHYL-3-(4-ISOPROPYLPHENYL)UREIDO-1-YL]BENZOIC ACID, DISODIUM SALT (COMPOUND 4)

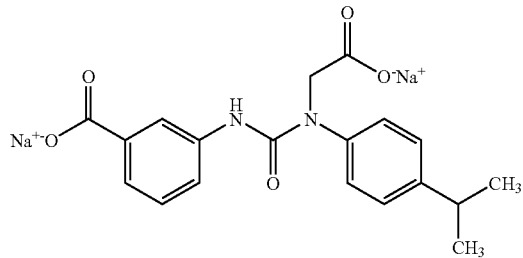

3-[3-(4-Isopropylphenyl)-2,5-dioxo-imidazolidin-1-y]-benzoic acid sodium salt (0.56 g) was dissolved in tetrahydrofuran (5 mL), and 5 N aq. sodium hydroxide was added. The mixture was stirred for 20 h, then was filtered. The solid was dissolved in acetone and filtered, and the filtrate was evaporated. The resulting residue was triturated with hexane, collected by filtration and dried under vacuum to afford the title product (0.23 g) as a white hydroscopic solid. Mass spectrum (ES+): m/z 357 (100) (the diacid). Elemental analysis: calculated for $C_{19}H_{18}N_2O_5Na_2 \cdot 2.2H_2O$ C 51.87, H 5.13, N 6.37; observed C 51.96, H 4.94, N 6.21.

5.8 Example 8

SYNTHESIS OF 3-[3-(3-METHOXY-PHENYL)-2,4-DIOXO-IMIDAZOLIDIN-1-YL]-BENZOIC ACID (COMPOUND 11)

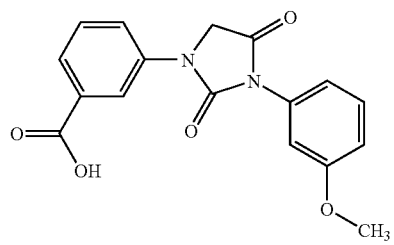

3.28 g of Rink Amide resin (4-(2',4'-dimethyoxyphenyl-Fmoc-aminomethyl)-phenoxy resin) was suspended in dry dimethylformamide (50 mL) for 10 min and the solvent was drained. To the resin was added 20% piperidine in dimethylformamide (50 mL) and agitated 30 min at room temperature. The solvents were drained and the resin was washed with dichloromethane (3×50 mL×1 min), dimethylformamide (3×50 mL×1 min), methanol (3×50 mL×1 min), and dichloromethane (3×50 mL×1 min). The resin was vacuum dried for 4 h.

Deprotected rink amide resin in dichloromethane (50 mL) was agitated for 10 min at room temperature, and then the solvent was drained. To a solution of bromoacetic acid (5.56 g) in 50% dimethylformamide/dichloromethane (50 mL) was added diisopropylcarbodiimide (4.91 mL) and stirred 5 min at room temperature. To the resin was added the reaction mixture and agitated 6 h at room temperature. The solvents were drained, and the resin was washed with dichloromethane (3×20 mL×10 min), dimethylformamide (3×20 mL×10 min), methanol (3×20 mL×10 min), and dichloromethane (3×20 mL×10 min). The resin was vacuum dried for 4 h. The desired product was analyzed by cleavage of a small amount of the reacted resin with triethylsilane/trifluoroacetic acid/dichloromethane(10/50/40). LC/MS (ESI) m/z 138 [M+H]+ and 95% purity.

To a suspension of bromoacetyl-rein (100 mg) in anhydrous dimethylformamide (1.5 mL) was added 3-aminobenzoic acid (150 mg). The reaction mixture was agitated overnight at room temperature. The solvents were drained, and the resin was washed with dichloromethane (3×10 mL×10 min), dimethylformamide (3×10 mL×10 min), methanol (3×10 mL×10 min), and dichloromethane (3×10 mL×10 min). The resin was vacuum dried for 4 h. The desired product was analyzed by cleavage of a small amount of the reacted resin with triethylsilane/trifluoroacetic acid/dichloromethane(10/50/40). LC/MS (ESI) m/z 195 [M+H]$^+$ and 95% purity.

To a suspension of 3-aminobenzoic acid substituted resin in anhydrous dichloromethane (1.5 mL) was added 3-methoxyphenylisocyanate (150 mg). The reaction mixture was agitated overnight at room temperature. The solvents were drained, and the resin was washed with dichloromethane (3×20 mL×10 min), dimethylformamide (3×20 mL×10 min), methanol (3×20 mL×10 min), and dichloromethane (3×20 mL×10 min). The resin was vacuum dried for 4 h. The desired product was analyzed by cleavage of a small amount of the reacted resin with trietylsilane/trifluoroacetic acid/dichloromethane(10/50/40). LC/MS (ESI) m/z 344 [M+H]$^+$ and 90% purity.

The resin was treated with triethylsilane/trifluoroacetic acid/dichloromethane(10/50/40) for 1 hour at room temperature and the solvents were drained and the resin washed with dichloromethane. The combined solvents were concentrated under reduced pressure, and the product was purified by preparative LC/MS eluting with acetonitrile-water gradient to afford the desired product as a white solid. LC/MS m/z 327 [M+H]$^+$.

5.9 Example 9

SYNTHESIS OF 3-[3-(2-CHLORO-BENZYL)-2,5-DIOXO-IMIDAZOLIDIN-1-YL]-BENZOIC ACID (COMPOUND 5)

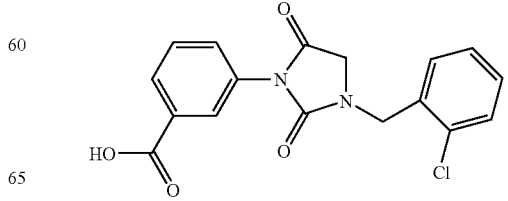

3.0 g of 2-chlorotrityl chloride resin in dichloromethane (50 mL) was agitated for 10 min at room temperature and the solvent was drained. To a solution of Fmoc-3-Aminobenzoic acid in anhydrous dichloromethane/dimethylformamide (30 mL) was added the resin and then a solution of diisopropylethylamine/dichloromethane (10 mL) at room temperature. The reaction mixture was agitated further 3 h at room temperature. The reaction was quenched with addition of 10 mL methanol, and the solvents were drained, and the resin was washed with dichloromethane (3×20 mL×10 min), dimethylformamide (3×20 mL×10 min), methanol (3×20 mL×10 min), and dichloromethane (3×20 mL×10 min). The resin was vacuum dried for 4 h. 10 mg of resin was treated with trifluoroacetic acid/dichloromethane/triethylsilane (20/70/10) for 10 min at room temperature and analyzed by LC/MS. LC/MS m/z 360 [M+H]$^+$.

Fmoc-3-aminobenzoic ester of 2-chlorotrityl resin (1 g) in dichloromethane (5 mL) was suspended for 10 min at room temperature and the solvent was drained. To the resin was added 20% piperidine in dimethylformamide (5 mL) and agitated 30 min at room temperature. The solvents were drained and the resin was re-suspended in 20% piperidine in dimethylformamide (5 mL) and agitated further 30 min at room temperature. The solvents were drained and the resin was washed with dichloromethane (3×50 mL×1 min), dimethylformamide (3×50 mL×1 min), methanol (3×50 mL×1 min), and dichloromethane (3×50 mL×1 min). 10 mg of resin was treated with trifluoroacetic acid/dichloromethane/triethylsilane (20/70/10) for 10 min at room temperature and analyzed by LC/MS. LC/MS m/z 138 [M+H]$^+$.

3.0 g of 3-aminobenzoic ester resin in dichloromethane (50 mL) was suspended for 10 min at room temperature and the solvent was drained. To a solution of bromoacetic acid (4.25 g) in anhydrous dichloromethane (30 mL) was added diisopropylcarbodiimide (3.76 mL) and stirred 5 min at room temperature. The diisopropylcarbodiimide activated acid was added to the resin and agitated for 18 h at room temperature. The solvents were drained, and the resin was washed with dichloromethane (3×20 mL×10 min), dimethylformamide (3×20 mL×10 min), methanol (3×20 mL×10 min), and dichloromethane (3×20 mL×10 min). 10 mg of resin was treated with trifluoroacetic acid/dichloromethane/triethylsilane(20/70/10) for 10 min at room temperature and analyzed by LC/MS. LC/MS m/z 258 [M+H]$^+$.

To a suspension of bromoacetyl-rein (100 mg) in anhydrous dimethylformamide (1.5 mL) was added 2-chlorobenzyl amine (150 mg). The reaction mixture was agitated overnight at room temperature. The solvents were drained, and the resin was washed with dichloromethane (3×5 mL×10 min), dimethylformamide (3×5 mL×10 min), methanol (3×5 mL×10 min), and dichloromethane (3×5 mL×10 min). The resin was dried under reduced pressure. 1 mg of resin was treated with trifluoroacetic acid/dichloromethane/triethylsilane(20/70/10) for 10 min at room temperature and analyzed by LC/MS. LC/MS m/z 319 [M+H]$^+$.

To a suspension of resin-bound urea intermediate (100 mg) in anhydrous dimethylformamide (1.5 mL) was added carbonyldiimidazole (52 mg). The reaction mixture was agitated overnight at room temperature. The solvents were drained, and the resin was washed with dichloromethane (3×5 mL×10 min), dimethylformamide (3×5 mL×10 min), methanol (3×5 mL×10 min), and dichloromethane (3×5 mL×10 min). The resin was dried under reduced pressure. The cyclized resin was treated with trifluoroacetic acid/dichloromethane/triethylsilane(20/70/10) for 60 min at room temperature and the product was purified by preparative LC/MS eluting with acetonitrile-water gradient to afford the desired product as a white solid. LC/MS m/z 345 [M+H]$^+$.

5.10 Example 10

SYNTHESIS OF 3-[5-(4-ISOPROPYL-PHENYL)-1,1-DIOXO-1L$^6$-[1,2,5]THIADIAZOLIDIN-2-YL]-BENZOIC ACID (COMPOUND 15)

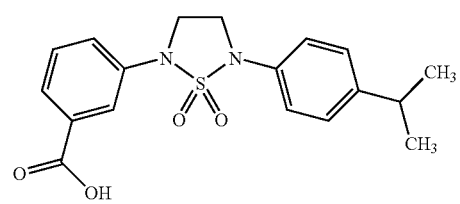

A solution of ethyl 3-aminobenzoate (5.00 g, 30.3 mmol) in chloroform (30.0 mL) was stirred at 0° C. as chlorosulfonic acid (1.00 mL, 15.0 mmol) was added over 15 minutes with stirring. After addition the reaction mixture was stirred at ambient temperature for 17 hours. The reaction mixture was extracted with 5% aqueous Na$_2$CO$_3$. The combined basic aqueous extract was washed with ether (4×20 mL) and concentrated to give a colorless solid. The solid was suspended in absolute ethanol (250 mL), heated at reflux for 10 minutes and filtered while hot. The filtrate was concentrated to give the product 3-sulfoamino-benzoic acid ethyl ester sodium salt as a colorless solid (1.73 g, 42% yield). m.p. 265(dec.)° C. $^1$H NMR (DMSO-d$_6$, 300 MHz): δ 8.18 (1H, m), 7.67 (1H, m), 7.21 (3H, m), 4.26 (2H, q, J=6.9 Hz), 1.29 (3H, t, J=6.9 Hz).

A suspension of the 3-sulfoamino-benzoic acid ethyl ester sodium salt (1.70 g, 6.36 mmol) in toluene (22 mL) was stirred at ambient temperature as phosphorous pentachloride (1.59 g, 7.64 mmol) was added. The mixture was heated at reflux for 24 h. The reaction mixture was filtered, concentrated and heated with stirring under high vacuum to 110° C., then cooled to ambient temperature to give 1.48 g of 3-sulfamoylchloride benzoic acid ethyl ester as a tan solid (88% yield). $^1$H NMR (CDCl$_3$, 300 MHz): δ 9.04 (1H, br s), 8.17 (1H, s), 7.99 (1H, dd, J=1.2, 7.8 Hz), 7.75 (1H, dd, J=2.1, 8.1 Hz), 7.53 (1H, t, J=8.1 Hz), 4.47 (2H, q, J=7.2 Hz), 1.44 (3H, t, J=7.2 Hz).

A solution of 3-sulfamoylchloride benzoic acid ethyl ester (0.529 g, 2.01 mmol) in anhydrous chloroform (10 mL) was stirred at ambient temperature as 4-isopropylaniline (0.301 g, 2.23 mmol) was added over 2 minutes. After addition, triethylamine (0.420 mL, 3.01 mmol) was added and the reaction mixture was stirred at ambient temperature for 17 hours. The reaction mixture was washed with 10% aqueous hydrochloric acid (2×4 mL), water (4 mL), dried over sodium sulfate and concentrated to give 0.74 g of the diphenylsulfamide as a tan solid. The product was purified by silica gel chromatography (24 g column, eluting with 1-3% ethyl acetate/methylene chloride) to give the product (0.355 g, 49% yield). m.p. 146-147° C. TLC R$_f$(30% ethyl acetate/hexanes) 0.46. $^1$H NMR (DMSO-d$_6$, 300 MHz): δ 10.36 (1H, s), 10.16 (1H, s), 7.69 (1H, s), 7.53 (1H, m), 7.38 (2H, m), 7.09 (2H, d, J=8.7 Hz), 6.99 (2H, d, J=8.7 Hz), 4.26 (2H, q, J=7.2 Hz), 2.74 (1H, m, J=6.9 Hz), 1.28 (3H, t, J=7.2 Hz), 1.12 (6H, d, J=6.9 Hz). Mass spectrum (ES+): m/z 363 (40), 299 (100).

A solution of 3-(((4-isopropyl)amino)sulfonyl)aminobenzoic acid ethyl ester (0.0943 g, 0.260 mmol) in anhydrous acetonitrile (5.2 mL) was stirred at ambient temperature as potassium carbonate (0.143 g, 1.04 mmol) and 1,2-dibromo-ethane (0.069 mL, 0.80 mmol) were added. The reaction mixture was heated at reflux for 17 h. The mixture was cooled to ambient temperature and the solid was filtered, washed with acetonitrile and discarded. The filtrate was concentrated to give the crude product which was purified by silica gel chromatography (3 g column, elated with 20% ethyl acetate/hexane) to give the product (0.084 g, 83% yield). m.p. 114-115° C. $^1$H NMR (CDCl$_3$, 300 MHz): δ 7.84 (2H, m), 7.64 (1H, m), 7.46 (1H, t, J=8.1 Hz), 7.28 (4H, m), 4.38 (2H, q, J=7.0 Hz), 4.03 (4H, m), 2.91 (1H, m, J=6.9 Hz), 1.40 (3H, t, J=7.2 Hz), 1.25 (6H, d, J=6.9 Hz). Mass spectrum (ES+): m/z 148(100), 389 (48).

A suspension of the cyclic sulfamide product prepared above (0.0740 g, 0.190 mmol) in absolute methyl alcohol (2 mL) and water (0.5 mL) was stirred at ambient temperature as potassium hydroxide (0.099 g, 1.76 mmol) was added. The mixture was stirred at ambient temperature for 17 h. The mixture was acidified with 10% aqueous hydrochloric acid to a pH of 2. The mixture was concentrated to give a solid which was suspended in water, filtered, washed with water and dried to give the product (0.0639 g, 93% yield). m.p. 255-256° C. $^1$H NMR (DMSO-d$_6$, 300 MHz): δ 7.85 (1H, br s), 7.75 (1H, d, J=7.5 Hz), 7.57 (2H, m), 7.29 (H, m), 4.05 (4H, dd, J=5.1, 12.6 Hz), 2.89 (1H, m, J=6.9 Hz), 1.20 (6H, d, J=6.9 Hz). Mass spectrum (ES+): m/z 148(100), 361 (35).

5.11 Example 11

SYNTHESIS OF 3-[6-(4-ISOPROPYL-PHENYL)-1,1-DIOXO-1L$^6$-[1,2,6]THIADIAZINAN-2-YL]-BENZOIC ACID (COMPOUND 7)

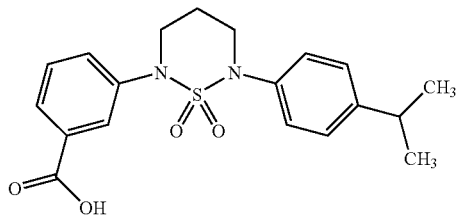

A solution of 3-sulfamide benzoic acid ethyl ester (0.066 g, 0.18 mmol) in anhydrous acetonitrile (3.8 mL) was stirred at ambient temperature as potassium carbonate (0.100 g, 0.724 mmol) and 1,3-diiodopropane (0.0563 g, 0.190 mmol) were added. The reaction mixture was heated at reflux for 3 h. The mixture was cooled to ambient temperature and the solid was filtered, washed with acetonitrile and discarded. The filtrate was concentrated to give the crude product which was purified by silica gel chromatography (4 g column, elated with 15% ethyl acetate/hexane) to give the product (0.064 g, 87% yield) as an amber oil. $^1$H NMR (CDCl$_3$, 300 MHz): δ 8.21 (1H, m), 7.95 (1H, m), 7.71 (1H, m), 7.354 (3H, m), 7.23 (2H, m), 4.38 (2H, q, J=7.2 Hz), 3.98 (4H, m), 2.91 (1H, m, J=6.9 Hz), 2.05 (2H, m), 1.41 (3H, t, J=7.2 Hz), 1.24 (6H, d, J=6.9 Hz). Mass spectrum (ES+); m/z 403(100).

A suspension of the cyclic sulfamide product prepared above (0.0450 g, 0.112 mmol) in absolute methyl alcohol (2 mL) and water (0.5 mL) was stirred at ambient temperature as potassium hydroxide (0.067 g, 1.02 mmol) was added. The mixture was stirred at ambient temperature for 48 h. The mixture was acidified with 10% aqueous hydrochloric acid to a pH of 2. The mixture was concentrated to give a solid which was suspended in water, filtered, washed with water and dried to give the product (0.0352 g, 84% yield). m.p. 199-200° C. $^1$H NMR (DMSO-d$_6$, 300 MHz): δ 13.19 (1H, br s), 8.07 (1H, s), 7.87 (1H, d, J=7.8 Hz), 7.71 (1H, m), 7.56 (1H, t, J=7.8 Hz), 7.42 (2H, d, J=8.1 Hz), 7.30 (2H, d, J=8.1 Hz), 3.90 (4H, m), 2.91 (1H, m, J=6.9 Hz), 1.97 (2H, m), 1.21 (6H, d, J=6.9 Hz). Mass spectrum (ES+): m/z 375(100).

5.12 Example 12

SYNTHESIS OF 3-[3-(4-ISOPROPYLPHENYL)-2-OXO-2,3-DIHYDROIMIDAZOL-1-YL]BENZOIC ACID (COMPOUND 35)

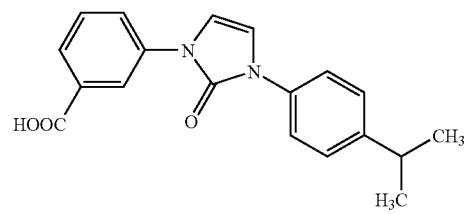

To a mixture of 4-isopropylaniline (4.05 g, 30.0 mmol) and potassium carbonate (6.21 g, 45 mmol) in DMF (100 mL) at room temperature was added 2-bromo-1,1-diethoxyethane (6.50 g, 33.0 mmol). The mixture was then stirred at 80-90° C. until all of the 4-isopropylaniline was consumed (24 h). The solvent was removed in vacuo and the residue was treated with dichloromethane (150 mL), washed with water and brine, dried over anhydrous MgSO$_4$, and then concentrated. Chromatography (silica gel, hexanes:ethyl acetate, 9:1) of the crude product, furnished the pure intermediate, N-(4-isopropylphenyl)-2,2-diethoxyethylamine, as a colorless oil (5.71 g, 75.8%). $^1$H NMR (CDCl$_3$, 300 MHz) δ (ppm) 1.18-1.32(m, 12H), 2.75-2.91 (m, 1H), 3.24 (d, 2H), 3.52-3.62 (m, 2H), 3.67-3.79 (m, 2H), 3.87 (s, br, 1H), 4.70 (t, 1H), 6.60 (d, 2H), 7.05 (d, 2H).

A solution of N-(4-isopropylphenyl)-2,2-diethoxyethylamine (0.50 g, 2.0 mmol) prepared above and 3-carbomethoxyphenyl isocyanate (0.36 g, 2.05 mmol) in dry dichloromethane (10 mL) was stirred at room temperature overnight. The solution was then chromatographed (silica gel, hexanes:ethyl acetate, 8:2) to give the pure urea, 3-[3-(2,2-diethoxyethyl)-3-(4-isopropylphenyl)ureido]benzoic acid methyl ester as a colorless oil (0.73 g, 85.3%). MS (ES−) m/z: 427. This was then stirred with HCl (0.5 M, 50 mL) at 80° C. for 4 h. After cooling to room temperature, the white precipitate formed was collected and purified by chromatography (silica gel, dichloromethane:ethyl acetate, 9:1) to give pure methyl 3-[3-(4-isopropylphenyl)-2-oxo-2,3-dihydroimidazol-1-yl]benzoate as white solid [0.42 g, 73.7%, MS (ES+) m/z: 337]. The solid was then treated with boron tribromide in dichloromethane (1.0 M, 4.0 mL) at room temperature overnight. The volatiles were removed in vacuum and the residue was suspended in water and stirred for 30 min. The solid was collected by filtration and washed with water to furnish 3-[3-(4-isopropylphenyl)-2-oxo-2,3-dihydroimidazol-1-yl]benzoic acid (0.40 g, 100%). m.p. 283-285° C. $^1$H NMR (CDCl$_3$, 300 MHz) δ (ppm) 1.24 (d, 6H), 2.84-3.00 (m, 1H), 6.69 (d, 1H), 6.74 (d, 1H), 7.26 (d, 2H), 7.45-7.54 (m, 3H), 7.91 (d, 1H), 8.02 (d, 1H), 8.12 (s, 1H). MS (ES−) m/z: 321.

Compound 37 shown in Table 1 above was prepared in the same fashion as described above, by using 3-carbomethoxyphenyl thioisocyanate instead of 3-carbomethoxyphenyl isocyanate for thiourea formation.

5.13 Example 13

3-[3-(3-ISOPROPYLPHENYL)-2-OXO-IMIDAZO-LIDIN-1-YL]BENZOIC ACID (COMPOUND 36)

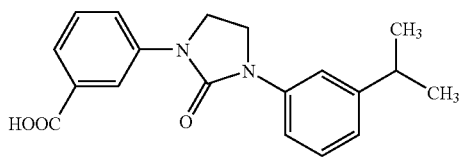

To a solution of methyl 3-aminobenzoate (4.53 g, 30.0 mmol) and triethylamine (3.54 g, 4.88 mL, 35.0 mmol) in dichloromethane (100 mL), at 0° C. while stirring, was added bromoacetyl bromide (6.66 g, 2.9 mL, 33.0 mmol) dropwise. After the addition, the mixture was stirred at room temperature overnight and passed through a short silica pad. The crude product, 3-(2-bromoacetylamino)benzoic acid methyl ester (8.09 g, 99.1%), obtained after the removal of the solvent (>99% by LC/MS, MS (ES+) m/z: 272, 274) was used without further purification.

3-(2-Bromoacetylamino)benzoic acid methyl ester (8.09 g, 29.7 mmol) prepare above was mixed with potassium carbonate (4.93 g, 35.7 mmol) and 4-isopropylaniline (4.41 g, 32.7 mmol) in DMF (100 mL), and the mixture was stirred at room temperature overnight. The solvent was then removed in vacuum and the residue was suspended in dichloromethane. The solid was filtered off and the filtrate was concentrated to give crude product, which was chromatographed (silica gel, hexanes:ethyl acetate, 8:2) to give 3-[2-(3-isopropylphenylamino)acetylamino]benzoic acid methyl ester as a pale yellow oil (8.18 g, 84.5%). MS (ES+) m/z: 327.

3-[2-(3-Isopropylphenylamino)acetylamino]benzoic acid methyl ester (3.26 g, 10.0 mmol) prepared above was treated with $BH_3 \cdot THF$ (1.0 M, 40.0 mL, 40.0 mmol) at room temperature for 24 h. The excess borane was destroyed by the addition of HCl (6 M, 10 mL). THF was removed in vacuum and the residue was diluted with water and basified. The organics were separated and the aqueous phase was extracted with dichloromethane. The organics were combined and washed with water and brine, dried over anhydrous $Na_2SO_4$ and concentrated. The crude product obtained after the removal of the solvent in vacuum was chromatographed (silica gel, dichloromethane:ethyl acetate, 9.5:0.5) to furnish 3-[2-(3-isopropylphenylamino)ethylamino]benzoic acid methyl ester as a colorless oil (2.28 g, 73.1%). MS (ES+) m/z: 313.

To the solution of 3-[2-(3-isopropylphenylamino)ethylamino]benzoic acid methyl ester (0.83 g, 2.7 mmol) prepared above in dry 1,2-dichloroethane (5.0 mL) was added, under nitrogen, 1,1'-carbonyldiimidazole (0.65 g, 4.0 mmol). The mixture was then heated at 90° C. for 24 h. After cooling to room temperature, the mixture was washed with water, diluted HCl, water and brine, then dried over anhydrous $Na_2SO_4$ and concentrated. The crude product was obtained after the removal of the solvent and further purified by column chromatography (silica gel, hexanes:ethyl acetate, 9:1) to give methyl 3-[3-(3-isopropylphenyl)-2-oxo-imidazolidin-1-yl]benzoate as colorless needles (0.78 g, 85.7%). MS (ES+) m/z: 339.

Methyl 3-[3-(3-isopropylphenyl)-2-oxo-imidazolidin-1-yl]benzoate obtained above (0.34 g, 1.0 mmol) was heated with NaOH (1.25 M, 2.0 mL, 2.5 mmol) in THF (5 mL) to reflux and stirred for 7 h. After cooling, THF was removed in vacuum and the residue was diluted with water (10 mL), followed by acidification. The precipitate was collected by filtration and washed with water, dried in air to furnish desire product 3-[3-(3-Isopropylphenyl)-2-oxo-imidazolidin-1-yl]-benzoic acid (0.32 g, 100%). m.p. 189-190° C. $^1H$ NMR ($CDCl_3$, 300 MHz) δ (ppm) 1.19 (d, 6H), 2.78-2.90 (m, 1H), 3.93 (s, 4H), 6.89 (d, 1H), 7.16-7.27 (m, 2H), 7.34 (t, 1H), 7.45 (s, 1H), 7.68 (d, 1H), 7.86 (s, 1H), 8.04 (d, 1H). MS (ES−) m/z: 323.

Compounds 34, 38, 40-43 and 60 were prepared in the same fashion as described above using either 1,1'-carbonyldiimidazole or 1,1'-thiocarbonyldiimidazole in the ring closure step.

5.14 Example 14

3-[2-OXO-3-(4-PYRROLIDIN-1-YL-PHENYL)-IMIDAZOLIDIN-1-YL]-BENZOIC ACID (COMPOUND 44)

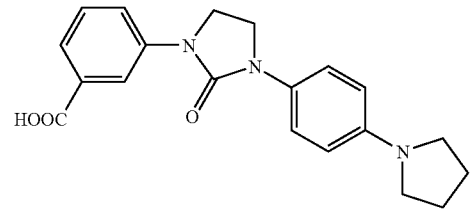

The methyl ester of 3-[3-(4-iodophenyl)-2-oxo-imidazolidin-1-yl]benzoic acid (0.42 g, 1.0 mmol) prepared as in Example 13 was mixed with 2-pyrolidinone (0.10 g, 0.09 mL, 1.2 mmol), CuI (0.02 g, 0.10 mmol), $Cs_2CO_3$ (0.65 g, 2.0 mmol), trans-1,2-hexanediamine (0.01 g, 0.01 mL, 0.1 mmol) and dioxane (5 mL). The mixture was heated at 110° C. with stirring for 12 h under nitrogen. After cooling to room temperature, the mixture was diluted with water (10 mL) and extracted with dichloromethane (10 mL×3) and the combined extracts were washed with water, brine and dried over anhydrous $Na_2SO_4$, and then concentrated. The crude product obtained after the removal of the solvent was chromatographed (silica, dichloromethane:ethyl acetate, 9:1) to provide pure product, 3-{2-oxo-3-[4-(2-oxo-pyrrolidin-1-yl)phenyl]imidazolidin-1-yl}benzoic acid methyl ester, as white solid (0.34 g, 89.5%). MS (ES+) m/z: 380.

3-{2-Oxo-3-[4-(2-oxo-pyrrolidin-1-yl)phenyl]imidazolidin-1-yl}benzoic acid methyl ester obtained above (0.061 g, 0.16 mmol) in THF (3.0 mL) was treated with $BH_3 \cdot THF$ (1.0 M, 0.32 mL, 0.32 mmol) at room temperature for 24 h. The excess borane was destroyed by the addition of HCl (6 M, 1.0 mL). THF was removed in vacuo and the residue was diluted with water and basified. The organics were separated and the aqueous phase was extracted with dichloromethane. The organics layers were combined and washed with water and brine, dried over anhydrous $Na_2SO_4$, which was later discarded. The crude product, 3-[2-oxo-3-(4-pyrrolidin-1-ylphenyl)imidazolidin-1-yl]benzoic acid methyl ester, obtained after the removal of the solvent in vacuo was analyzed by LC/MS and revealed to be >99% pure[MS (ES+) m/z: 366], and was used without further purification.

The above ester was heated with NaOH (1.25 M, 0.26 mL, 0.32 mmol) in THF (3 mL) to reflux and stirred for 7 h. After cooling, THF was removed in vacuo and the residue was diluted with water (5 mL), followed by neutralization to pH 6. The precipitate was collected by filtration and washed with water, dried in air to furnish desire product 3-[2-Oxo-3-(4-pyrrolidin-1-yl-phenyl)imidazolidin-1-yl]benzoic acid (0.056 g, 100%). m.p. 276-278 (decomp.). $^1$H NMR (CDCl$_3$/DMSO-d$_6$, 300 MHz) δ (ppm) 1.72 (t, 4H), 2.95 (t, 4H), 3.68 (s, 4H), 6.45 (d, 2H), 7.20-7.37 (m, 3H), 7.60 (d, 1H), 7.90-8.00 (m, 2H). MS (ES−) m/z: 350.

5.15 Example 15

3-[2-OXO-3-(4-PIPERIDIN-1-YL-PHENYL)IMI-DAZOLIDIN-1-YL]-BENZOIC ACID (COMPOUND 59)

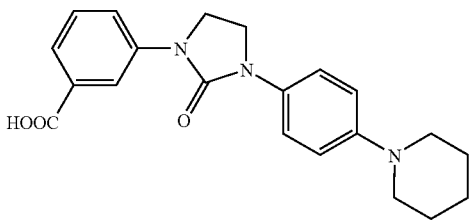

To a solution of methyl 3-aminobenzoate (4.53 g, 30.0 mmol) in dry toluene (50 mL) was added 2-chloroethylisocyante (3.48 g, 2.81 mL, 33.0 mmol). The mixture was stirred at 40° C. for 12 h. After cooling to room temperature, the solid was collected by filtration and washed with toluene, water and dried in air to provide urea, 3-[3-(2-chloro-ethyl)ureido] benzoic acid methyl ester [7.41 g, 96.2%, >95% pure by LC/MS, MS (ES+) m/z: 257, 259]. The urea (2.56 g, 10.0 mmol) was then stirred in DMF (50.0 mL) with K$_2$CO$_3$ (1.65 g, 11.98 mmol) at room temperature for 12 h. The solid was filtered off and the solvent was removed in vacuum. The crude product was dissolved in dichloromethane and passed through a silica column (50 g) and eluted with dichloromethane:ethyl acetate, 7:3 to give pure cyclic urea intermediate, 3-(2-oxo-imidazolidin-1-yl)benzoic acid methyl ester, as white crystalline material (5.36 g, 81.5%). MS (ES+) m/z: 221.

3-(2-Oxo-imidazolidin-1-yl)benzoic acid methyl ester (0.128 g, 0.58 mmol) prepared above was mixed with 4-piperidin-1-yl iodobenzene (0.201 g, 0.70 mmol), CuI (0.011 g, 0.06 mmol), K$_3$PO$_4$ (0.246 g, 1.16 mmol), N,N'-dimethyl ethylenediamine (0.005 g, 0.006 mL, 0.06 mmol) and dioxane (3 mL). The mixture was heated at 110° C. with stirring for 12 h, and the solvent was then removed in vacuum. The residue was suspended in dichloromethane and passed through a short silica pad, the product, methyl ester of 3-[2-Oxo-3-(4-piperidin-1-ylphenyl)imidazolidin-1-yl]benzoic acid, was eluted with dichloromethane:methanol, 9.5:0.5 (0.210 g, 95.5%). MS (ES+) m/z: 380.

The methyl ester of 3-[2-Oxo-3-(4-piperidin-1-ylphenyl) imidazolidin-1-yl]benzoic acid obtained above (0.20 g, 0.53 mmol) was heated with NaOH (1.25 M, 1.0 mL, 1.25 mmol) in THF (3 mL) to reflux and stirred for 7 h. After cooling, THF was removed in vacuum and the residue was diluted with water (10 mL), followed by neutralization to pH 6. The precipitate was collected by filtration and washed with water, dried in air to furnish desire product 3-[2-oxo-3-(4-piperidin-1-ylphenyl)imidazolidin-1-yl]benzoic acid (0.178 g, 92.2%). m.p. 284-286 (decomp.). $^1$H NMR (CDCl$_3$, 300 MHz) δ (ppm) 1.38-1.80 (m, 6H), 2.90-3.15 (t, 4H), 3.88 (s, 4H), 6.82 (s, br, 2H), 7.19-7.42 (m, 3H), 7.63 (d, 1H), 7.84 (s, 1H), 8.02 (d, 1H). MS (ES−) m/z: 364.

Compounds 39, 45-51, 56, 61, 63-79 and 81 can be prepared in the same fashion as described above.

5.16 Example 16

2-FLUORO-5-[2-OXO-3-(4-TRIFLUOROM-ETHYL-PHENYL)-IMIDAZOLIDIN-1-YL]-BENZOIC ACID (COMPOUND 53)

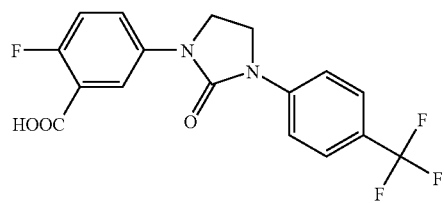

To a solution of methyl 4-trifluoromethylaniline (3.47 g, 21.6 mmol) in dry toluene (50 mL) was added 2-chloroethylisocyante (2.50 g, 2.02 mL, 23.7 mmol). The mixture was stirred at 40° C. for 12 h. After cooling to room temperature, the solid was collected by filtration and washed with toluene, water and dried in air to provide 1-(2-chloro-ethyl)-3-(4-trifluoromethylphenyl)urea [5.28 g, 92.0%, >95% pure by LC/MS MS (ES+) m/z: 267, 269]. The urea (5.27 g, 23.7 mmol) was then stirred in DMF (50.0 mL) with K$_2$CO$_3$ (3.27 g, 11.98 mmol) at room temperature for 12 h. The solid was filtered off and the solvent was removed in vacuum. The crude product was dissolved in dichloromethane and passed through a silica column (50 g) and eluted with dichloromethane:ethyl acetate, 8:2 to give pure cyclic urea intermediate, 1-(4-trifluoromethylphenyl)imidazolidin-2-one, as white crystalline material (3.85 g, 84.7%). MS (ES+) m/z: 231.

1-(4-Trifluoromethylphenyl)imidazolidin-2-one (0.115 g, 0.50 mmol) prepared above was mixed with methyl 2-fluoro-5-iodobenzoate (0.168 g, 0.60 mmol), CuI (0.006 g, 0.03 mmol), K$_3$PO$_4$ (0.254 g, 1.20 mmol), N,N'-dimethyl ethylenediamine (0.004 g, 0.005 mL, 0.05 mmol) and dioxane (3 mL). The mixture was heated at 110° C. with stirring for 12 h, and the solvent was then removed in vacuum. The residue was suspended in dichloromethane and passed through a short silica pad, the product, methyl ester of 2-fluoro-5-[2-oxo-3-(4-trifluoromethylphenyl)imidazolidin-1-yl]benzoic acid, was eluted with dichloromethane:ethyl acetate (9.5:0.5) (0.188 g, 98.4%). MS (ES+) m/z: 383.

The methyl ester obtained above (0.180 g, 0.47 mmol) was heated with NaOH (1.25 M, 0.65 mL, 0.94 mmol) in THF (3 mL) to reflux and stirred for 7 h. After cooling, THF was removed in vacuum and the residue was diluted with water (10 mL), followed by acidification. The precipitate was collected by filtration and washed with water, dried in air to furnish desire product 2-fluoro-5-[2-oxo-3-(4-trifluoromethylphenyl)imidazolidin-1-yl]benzoic acid (0.170 g, 98.3%). m.p. 241-242. $^1$H NMR (CDCl$_3$, 300 MHz) δ (ppm) 3.97 (s, 4H), 7.09 (t, 1H), 7.53 (d, 2H), 7.65 (d, 2H), 7.74-7.82 (m, 1H), 7.95-8.03 (m, 1H). MS (ES−) m/z: 367.

Compounds 52, 54, 55, 57 and 80 can be prepared in the same fashion as described above.

5.17 Example 17

Identification and Characterization of Compounds that Promote Nonsense Suppression and/or Modulate Translation Termination

5.17.1 Increase in vitro Nonsense Suppression at UBA Codon

Compounds of the invention are characterized further with the in vitro luciferase nonsense suppression assay. To ensure that the observed nonsense suppression activity of the selected compounds is not limited to the rabbit reticulocyte assay system, HeLa cell extract is prepared and optimized (Lie & Macdonald, 1999, Development 126(22):4989-4996 and Lie & Macdonald, 2000, Biochem. Biophys. Res. Commun. 270(2):473-481). The nonsense suppression activity of compounds of the invention, with respect to the UBA codon, are compared to gentamicin in the HeLa cell translation extracts.

5.17.2 Characterization of Compounds that Increase Nonsense Suppression and Produce Functional Protein A stable cell line harboring the UBA nonsense-containing luciferase gene is treated with a test compound. Cells are grown in standard medium supplemented with 1% penicillin-streptomycin (P/S) and 10% fetal bovine serum (FBS) to 70% confluency and split 1:1 the day before treatment. The next day, cells are trypsinized and 40,000 cells are added to each well of a 96-well tissue culture dish. Serial dilutions of each compound are prepared to generate a six-point dose response curve spanning 2 logs (30*M to 0.3*M). The final concentration of the DMSO solvent remains constant at 1% in each well. Cells treated with 1% DMSO serve as the background standard, and cells treated with gentamicin serve as a positive control.

5.17.3 Alteration of the Accessibility of Chemical Modifying Agents to Specific Nucleotides in the 28S rRNA Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, *E. coli* numbering) of the rRNA at nucleotides 1406, 1407, 1494, and 1496 (Moazed & Noller, 1987, Nature 327(6121):389-394; Woodcock et al., 1991, EMBO J. 10(10):3099-3103; and Schroeder et al., 2000, EMBO J. 19:1-9.

Ribosomes prepared from HeLa cells are incubated with the small molecules (at a concentration of 100 mM), followed by treatment with chemical modifying agents (dimethyl sulfate [DMS] and kethoxal [KE]). Following chemical modification, rRNA is phenol-chloroform extracted, ethanol precipitated, analyzed in primer extension reactions using end-labeled oligonucleotides hybridizing to different regions of the three rRNAs and resolved on 6% polyacrylamide gels. The probes used for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

5.17.4 Readthrough of Premature Termination Codon in Cell-Based Disease Models To address the effects of the nonsense-suppressing compounds on mRNAs altered in specific inherited diseases, a bronchial epithelial cell line harboring a nonsense codon at amino acid 1282 (W1282X) is treated with a compound of formula I and CFTR function is monitored as a cAMP-activated chloride channel using the SPQ assay (Yang et al., 1993, Hum Mol Genet. 2(8):1253-1261 and Howard et al., 1996, Nat Med. 2(4):467-469). The increase in SPQ fluorescence in cells treated with a compound of formula I is compared to those treated with cAMP and untreated cells. An increase in SPQ fluorescence in cells is consistent with stimulation of CFTR-mediated halide efflux and an increase in readthrough of the nonsense codon. Full-length CFTR expression from this nonsense-containing allele following treatment with a compound of formula I demonstrates that cystic fibrosis cell lines increase chloride channel activity when treated with a compound of formula I.

5.17.5 Expression of Full Length Dystrophin Protein in the Nonsense Mutation-Containing MDX Mouse Cell by Treatment The mutation in the mdx mouse that premature termination of the 427 kDa dystrophin polypeptide has been shown to be a C to T transition at position 3185 in exon 23 (Sicinski et al., 1989, Science. 244(4912):1578-1580). Mouse primary skeletal muscle cultures derived from 1-day old mdx mice are prepared as described previously (Barton-Davis et al., 1999, J Clin Invest. 104(4):375-381). Cells are cultured for 10 days in the presence of a compound of formula I. Culture medium is replaced every four days and the presence of dystrophin in myoblast cultures is detected by immunostaining as described previously (Barton-Davis et al., 1999, J Clin Invest. 104(4):375-381). A primary monoclonal antibody to the C-terminus of the dystrophin protein (F19A12) is used undiluted and rhodamine conjugated anti-mouse IgG was used as the secondary antibody. The F19A12 antibody detects the full-length protein produced by suppression of the nonsense codon. Staining is viewed using a Leica DMR microscope, digital camera, and associated imaging software at the University of Pennsylvania.

5.17.6 Readthrough of Premature Termination Codon in the MDX

As previously described (Barton-Davis et al., 1999, J Clin Invest. 104(4):375-381), compound is delivered by Alzet osmotic pumps implanted under the skin of anesthetized mice. Two doses of a compound of formula I are administered. Gentamicin serves as a positive control and pumps filled with solvent only serve as the negative control. Pumps are loaded with appropriate compound such that the calculated doses to which tissue is exposed are 10 mM and 20 mM. The gentamicin concentration is calculated to achieve tissue exposure of approximately 200 mM. In the initial experiment, mice are treated for 14 days, after which animals are anesthetized with ketamine and exsanguinated. The tibialis anterior (TA) muscle of the experimental animals is then excised, frozen, and used for immunofluorescence analysis of dystrophin incorporation into striated muscle. The presence of dystrophin in TA muscles is detected by immunostaining, as described previously (Barton-Davis et al., 1999, J Clin Invest. 104(4):375-381).

5.18 Example 18

100 mg Oral Dosage Form

Table 2 illustrates a batch formulation and a single dose unit formulation containing 100 mg of 3-(3-(4-isopropyl-phenyl)-2,5-dioxo-imidazolidin-1-yl)-benzoic acid sodium salt.

TABLE 2

Formulation for 100 mg tablet

| Material | Percent by Weight | Quantity (mg/tablet) | Quantity (kg/batch) |
|---|---|---|---|
| 3-(3-(4-isopropyl-phenyl)-2,5-dioxo-imidazolidin-1-yl)-benzoic acid sodium salt | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and 3-(3-(4-isopropyl-phenyl)-2,5-dioxo-imidazolidin-1-yl)-benzoic acid sodium salt components are passed through a #30 mesh screen (about 430µ to about 655µ). The Pluronic F-68® (manufactured by JRH Biosciences, Inc. of Lenexa, Kans.) surfactant is passed through a #20 mesh screen (about 457µ to about 1041µ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

5.19 Example 19

Aerosol Dosage Form

A concentrate is prepared by combining 3-[3-(4-isopropyl-phenyl)-ureido]-benzoic acid, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| ipratropium bromide, | 0.0021 g |
| (3-[3-(4-isopropyl-phenyl)-ureido]-benzoic acid) | 0.0120 g |
| trichloromonofluoromethane | 1.6939 g |
| dichlorodifluoromethane | 3.7028 g |
| dichlorotetrafluoroethane | 1.5766 g |
| total | 7.0000 g |

5.20 Intravenous Dosage Form

The intravenous formulation is prepared by reconstituting a compound of the invention with an appropriate liquid medium, such as water for injection (WFI) or a 5% dextrose solution. A desired concentration of the intravenous formulation can be obtained by reconstituting an appropriate amount of a compound of the invention with an appropriate volume of liquid medium. A desired concentration of the intravenous formulation provides a therapeutically effective amount of a compound of the invention to the patient, preferably a mammal, more preferably a human, in need of the intravenous pharmaceutical formulation and maintains a therapeutically effective level of a compound of the invention in the patient. The dose which is therapeutically effective will depend on the rate at which the intravenous formulation is delivered to the patient and the concentration of the intravenous formulation. For example, two vials containing a composition (e.g., 500 mg of a compound of the invention per vial) are reconstituted with a 5% dextrose solution (14 ml of 5% dextrose solution per vial) yielding a total of 28 mL of solution. The reconstituted solution is incorporated into a dextrose solution in an infusion bag and q.s. to 166 mL, resulting in a solution containing 6 mg/ml of a compound of the invention suitable for intravenous infusion administration. The preferred concentration of a compound of the invention in the liquid medium, in the infusion bag, is about 3 to about 10 mg/ml, preferably about 5 to about 6 mg/ml.

While the invention has been described with respect to the particular embodiments, it will be apparent to those skilled in the art that various changes and modifications can be made without departing from the spirit and scope of the invention as defined in the claims. Such modifications are also intended to fall within the scope of the appended claims.

What is claimed is:
1. A compound having the structure:

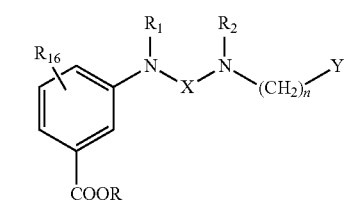

or a pharmaceutically acceptable salt or stereoisomer thereof, wherein:
X is C(=O), S, S(=O) or S(O)$_2$;

Y is:

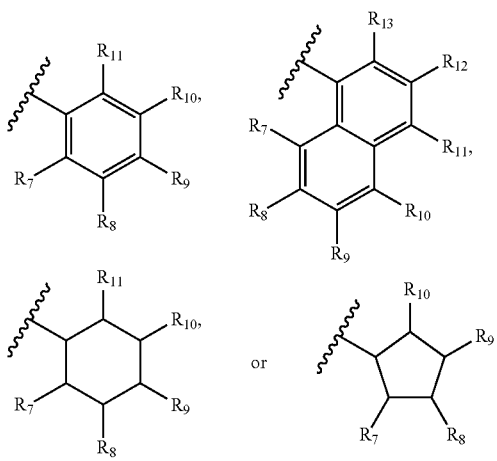

R is hydrogen, substituted or unsubstituted alkyl, substituted or unsubstituted cycloalkyl or substituted or unsubstituted aryl;

n is an integer ranging from 0-4;

$R_1$ and $R_2$ together form:

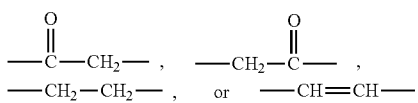

$R_7$ is hydrogen, halogen, substituted or unsubstituted alkyl, substituted or unsubstituted alkenyl, substituted or unsubstituted alkynyl, substituted or unsubstituted cycloalkyl, carbonyl, alkylcarbonyl, substituted or unsubstituted aryl, alkylaryl, cyano, nitro, haloalkoxy, alkylamino, alkoxycarbonyl, aryloxy, arylalkyloxy, arylalkyl, cycloalkylalkyloxy, cycloalkyloxy, alkoxyalkyl, alkoxyalkoxy, or aminoalkoxy;

$R_8$ is hydrogen, substituted or unsubstituted alkyl, substituted or unsubstituted alkenyl, substituted or unsubstituted alkynyl, substituted or unsubstituted cycloalkyl, alkylcarboxy, carbonyl, alkylcarbonyl, substituted or unsubstituted aryl, alkylaryl, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy;

$R_9$ is hydrogen, hydroxy, substituted or unsubstituted alkyl, substituted or unsubstituted alkenyl, substituted or unsubstituted alkynyl, substituted or unsubstituted cycloalkyl, carboxy, alkylcarboxy, carbonyl, alkylcarbonyl, substituted or unsubstituted aryl, alkylaryl, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy;

$R_{10}$ is hydrogen, substituted or unsubstituted alkyl, substituted or unsubstituted alkenyl, substituted or unsubstituted alkynyl, substituted or unsubstituted cycloalkyl, alkylcarboxy, carbonyl, alkylcarbonyl, substituted or unsubstituted aryl, alkylaryl, substituted or unsubstituted heterocyclo, cyano, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy;

$R_{11}$ is hydrogen, halogen, substituted or unsubstituted alkyl, substituted or unsubstituted alkenyl, substituted or unsubstituted alkynyl, substituted or unsubstituted cycloalkyl, carbonyl, alkylcarbonyl, substituted or unsubstituted aryl, alkylaryl, substituted or unsubstituted heterocyclo, substituted or unsubstituted heteroaryl, cyano, nitro, haloalkoxy, alkylamino, alkoxycarbonyl, aryloxy, arylalkyloxy, arylalkyl, cycloalkylalkyloxy, cycloalkyloxy, alkoxyalkyl, alkoxyalkoxy, or aminoalkoxy; and $R_{12}$, $R_{13}$ and $R_{16}$ are independently hydrogen, halogen, hydroxy, substituted or unsubstituted alkyl, substituted or unsubstituted alkenyl, substituted or unsubstituted alkynyl, substituted or unsubstituted cycloalkyl, carboxy, alkylcarboxy, carbonyl, alkylcarbonyl, substituted or unsubstituted aryl, alkylaryl, substituted or unsubstituted heterocyclo, substituted or unsubstituted heteroaryl, cyano, nitro, sulfonyl, alkoxy, haloalkoxy, alkylthio, alkylamino, alkoxycarbonyl, aryloxy, arylalkyloxy, arylalkyl, cycloalkylalkyloxy, cycloalkyloxy, alkoxyalkyl, alkoxyalkoxy, alkylamino or aminoalkoxy.

2. A compound of claim 1, wherein the compound is a substantially pure enantiomer.

3. A compound of claim 1, wherein $R_1$ and $R_2$ together form:

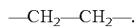

4. A compound of claim 1, wherein X is S or S(=O).

5. A compound of claim 1, wherein Y is:

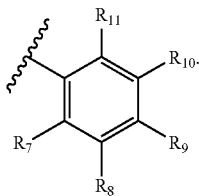

6. A compound of claim 1, wherein $R_1$ and $R_2$ together form —$CH_2$—$CH_2$—, X is C(=O) and Y is:

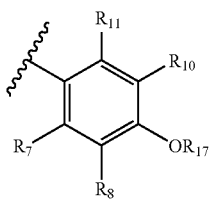

wherein $R_{17}$ is substituted alkyl.

7. A compound of claim 6, wherein $R_{17}$ is substituted with fluorine.

8. A compound of claim 1, wherein $R_1$ and $R_2$ together form —$CH_2$—$CH_2$—, X is C(=O) and Y is:

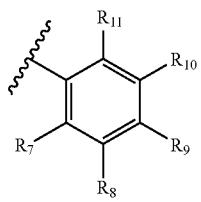

wherein $R_7$ and $R_{11}$ are hydrogen.

9. A compound of claim 1, wherein one of $R_8$-$R_{10}$ is halogen.

10. A compound of claim 1, wherein two of $R_8$-$R_{10}$ are halogen.

11. A compound of claim 1, wherein $R_1$ and $R_2$ together form —CH$_2$—CH$_2$— and Y is:

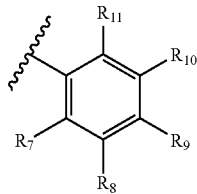

wherein one of $R_8$-$R_{10}$ is other than hydrogen.

12. A compound of claim 1, wherein $R_1$ and $R_2$ taken together form —C(=O)CH$_2$— and Y is:

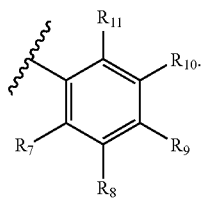

13. A compound of claim 1 having the structure:

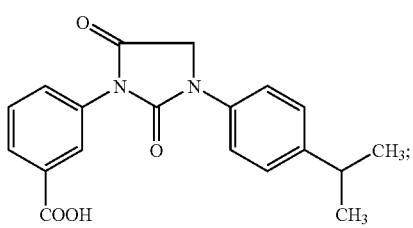

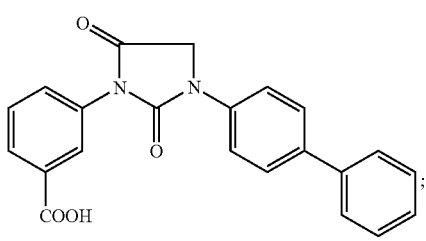

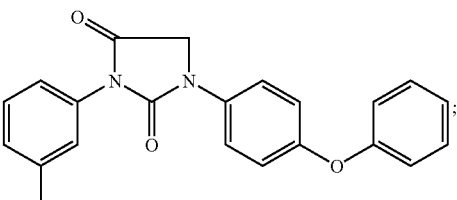

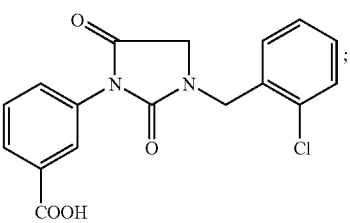

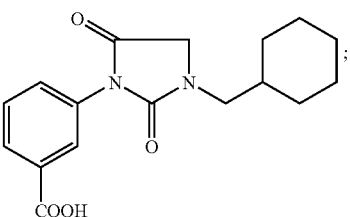

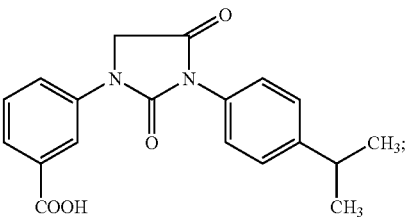

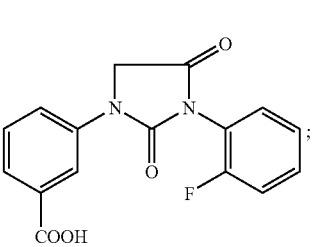

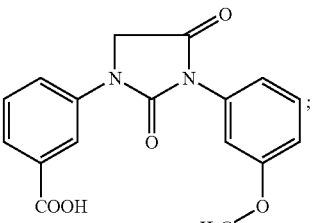

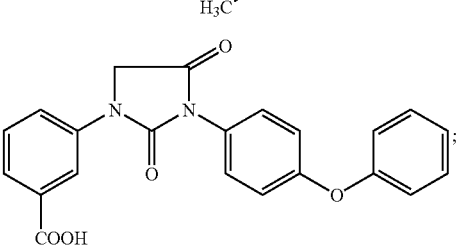

107
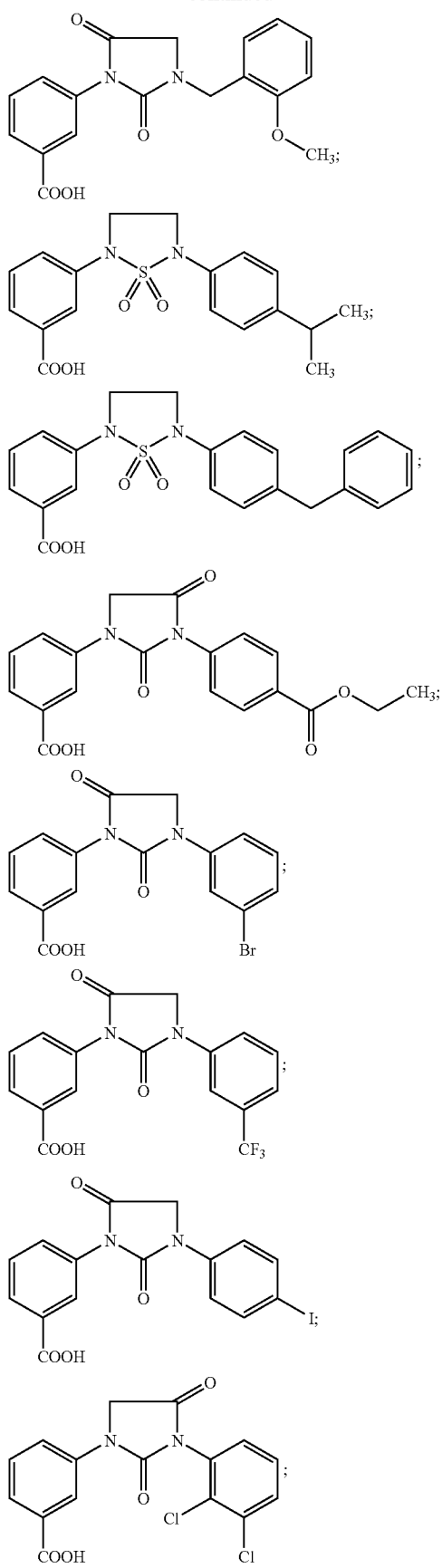
108
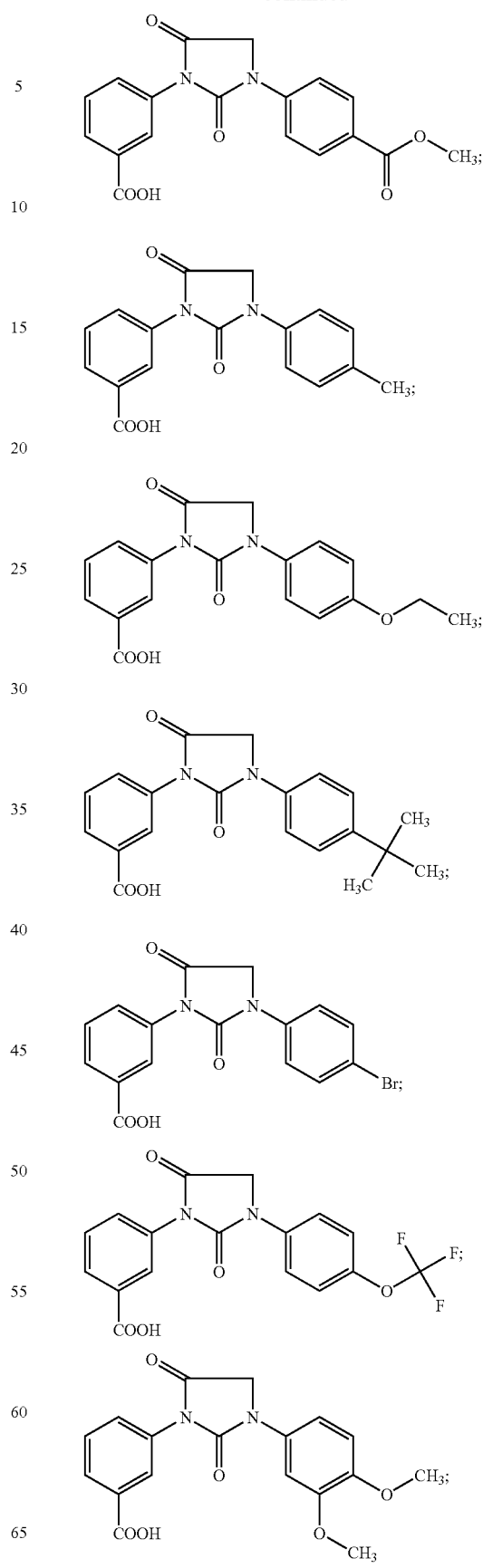

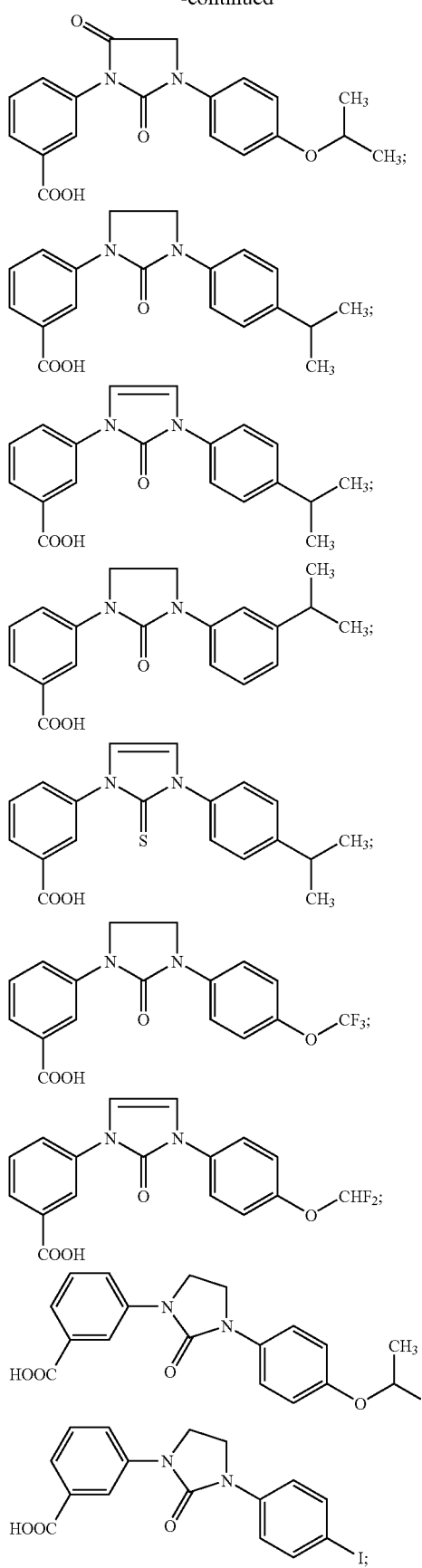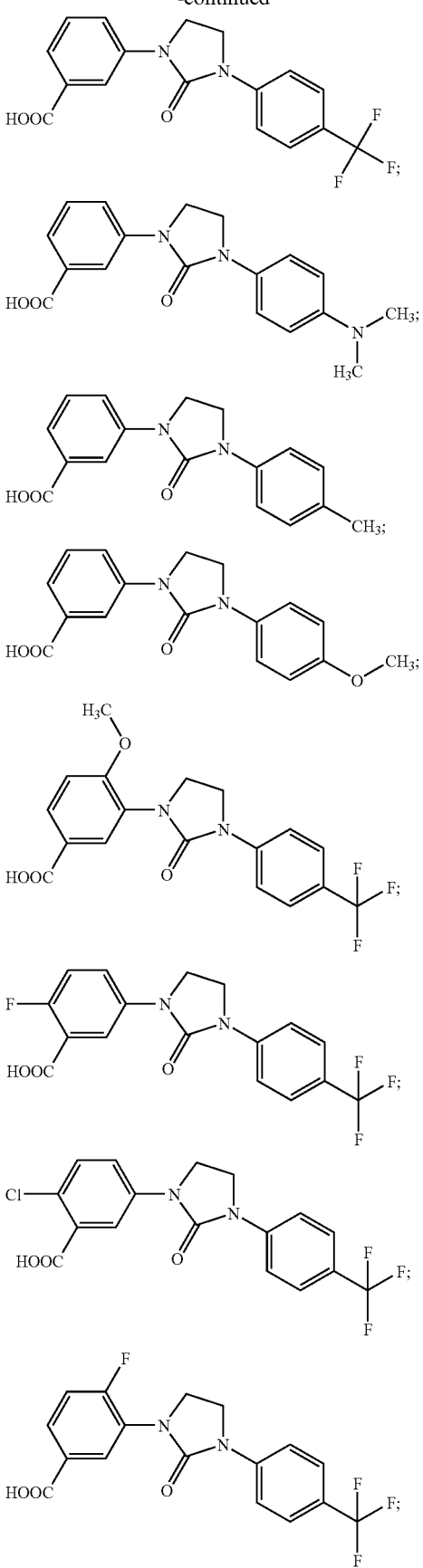

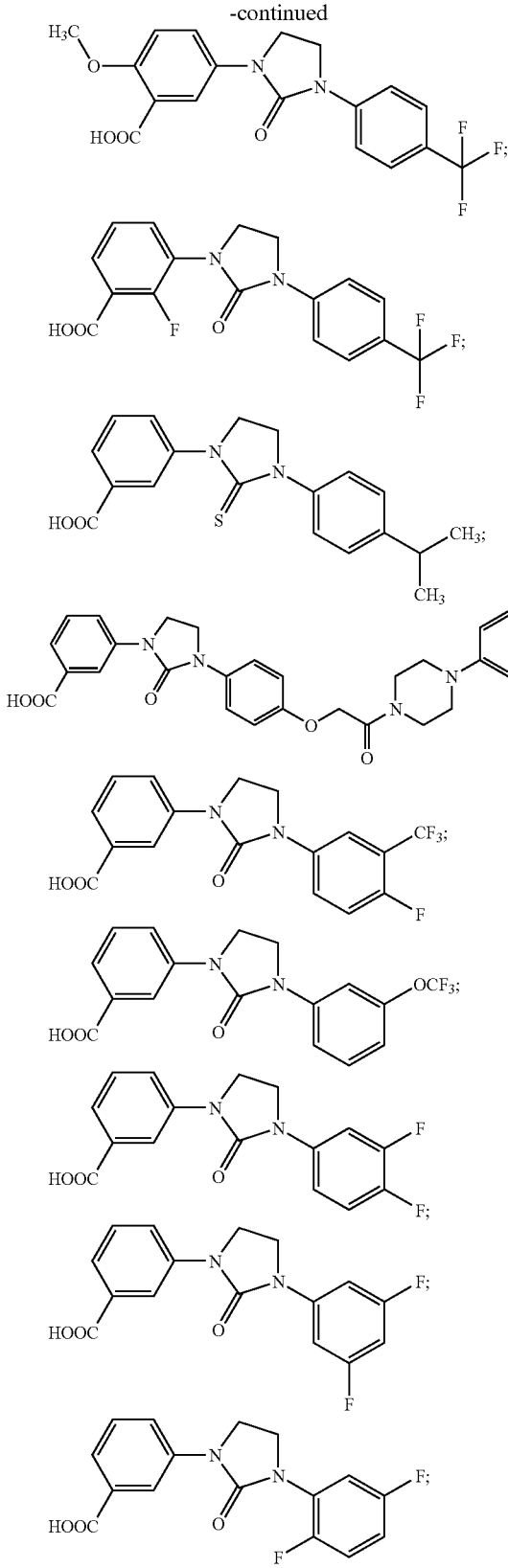
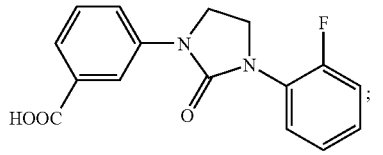
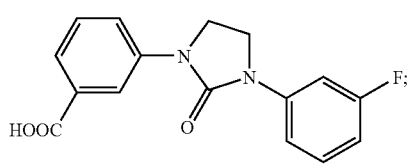
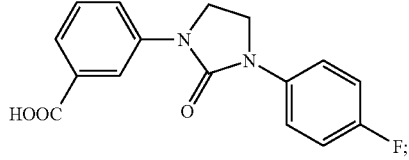
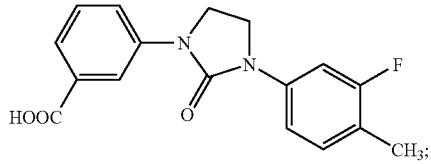
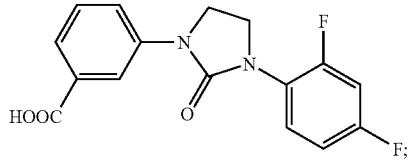
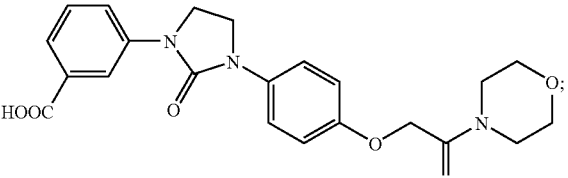
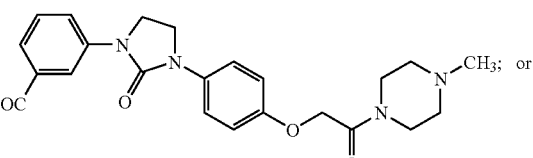
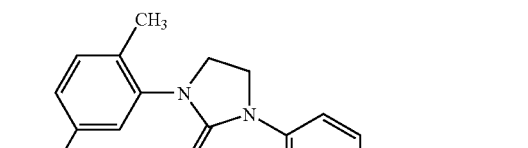
or a pharmaceutically acceptable salt, or stereoisomer thereof.
* * * * *